(12) United States Patent
Presta et al.

(10) Patent No.: US 11,299,551 B2
(45) Date of Patent: Apr. 12, 2022

(54) COMPOSITE BINDING MOLECULES TARGETING IMMUNOSUPPRESSIVE B CELLS

(71) Applicant: Biograph 55, Inc., San Francisco, CA (US)

(72) Inventors: Leonard Presta, San Francisco, CA (US); Paul Tumeh, San Francisco, CA (US); Nils Lonberg, Woodside, CA (US); Omar Duramad, Berkeley, CA (US)

(73) Assignee: Biograph 55, Inc., San Francisco, CA (US)

( * ) Notice: Subject to any disclaimer, the term of this patent is extended or adjusted under 35 U.S.C. 154(b) by 0 days.

(21) Appl. No.: 17/229,751

(22) Filed: Apr. 13, 2021

(65) Prior Publication Data

US 2021/0269545 A1 Sep. 2, 2021

Related U.S. Application Data

(63) Continuation of application No. PCT/US2021/019685, filed on Feb. 25, 2021.

(60) Provisional application No. 63/094,838, filed on Oct. 21, 2020, provisional application No. 62/990,330, filed on Mar. 16, 2020, provisional application No. 62/981,990, filed on Feb. 26, 2020.

(51) Int. Cl.
*C07K 16/28* (2006.01)
*A61K 39/00* (2006.01)

(52) U.S. Cl.
CPC ...... *C07K 16/2896* (2013.01); *C07K 16/2803* (2013.01); *A61K 2039/507* (2013.01); *C07K 2317/31* (2013.01); *C07K 2317/55* (2013.01); *C07K 2317/565* (2013.01); *C07K 2317/622* (2013.01)

(58) Field of Classification Search
CPC .......... C07K 2317/565; C07K 16/2896; A61K 2039/507
USPC ..................................................... 424/133.1
See application file for complete search history.

(56) References Cited

U.S. PATENT DOCUMENTS

| | | | |
|---|---|---|---|
| 7,943,743 B2 | 5/2011 | Korman et al. | |
| 8,008,449 B2 | 8/2011 | Korman et al. | |
| 8,097,703 B2 | 1/2012 | Rao-Naik et al. | |
| 8,258,268 B2 | 9/2012 | Wu et al. | |
| 8,263,746 B2 | 9/2012 | Tesar et al. | |
| 8,354,509 B2 | 1/2013 | Carven et al. | |
| 8,409,577 B2 | 4/2013 | Thompson et al. | |
| 9,040,050 B2 | 5/2015 | Van De Winkel et al. | |
| 9,056,917 B2 | 6/2015 | Hansen et al. | |
| 9,200,061 B2 | 12/2015 | Tesar et al. | |
| 9,249,226 B2 | 2/2016 | De Weers et al. | |
| 9,603,927 B2 | 3/2017 | Doshi | |
| 9,758,590 B2 | 9/2017 | Tesar et al. | |
| 9,932,412 B2 | 4/2018 | Kim et al. | |
| 9,944,711 B2 | 4/2018 | De Weers et al. | |
| 10,266,608 B2 | 4/2019 | Wu | |
| 10,519,251 B2 | 12/2019 | Wu | |
| 2009/0055944 A1 | 2/2009 | Korman et al. | |
| 2009/0123950 A1 | 5/2009 | Tesar | |
| 2009/0217401 A1 | 8/2009 | Korman et al. | |
| 2010/0203056 A1 | 8/2010 | Irving et al. | |
| 2011/0008369 A1 | 1/2011 | Finnefrock et al. | |
| 2011/0117085 A1 | 5/2011 | Rotem-Yehudar et al. | |
| 2011/0223188 A1 | 9/2011 | Langermann | |
| 2012/0039906 A1 | 2/2012 | Olive | |
| 2013/0017199 A1 | 1/2013 | Langermann | |
| 2014/0099254 A1 | 4/2014 | Chang et al. | |
| 2016/0096901 A1 | 4/2016 | Tesar et al. | |
| 2017/0174780 A1 | 6/2017 | Doshi | |
| 2017/0320967 A1 | 11/2017 | Yang et al. | |
| 2018/0194861 A1 | 7/2018 | Dong et al. | |
| 2019/0038671 A1* | 2/2019 | Fan .................. C07K 16/00 |
| 2019/0177439 A1 | 6/2019 | Wu | |

FOREIGN PATENT DOCUMENTS

| | | |
|---|---|---|
| WO | WO-2007002223 A2 | 1/2007 |
| WO | WO-2009054863 A2 | 4/2009 |
| WO | WO-2009089004 A1 | 7/2009 |
| WO | WO-2014191113 A1 | 12/2014 |
| WO | WO-2019195535 A1 | 10/2019 |
| WO | WO-2019197979 A1 | 10/2019 |
| WO | WO-2020180398 A1 | 9/2020 |
| WO | WO-2021146464 A1 | 7/2021 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44:1075-1084).*
Chen et al. (J. Mol. Bio. (1999) 293, 865-881).*
Wu et al. (J. Mol. Biol. (1999) 294, 151-162).*
ATCC Raji cell data sheet (pp. 1-10 (2021)).*
Mihara et al. (Journal of Hematology & Oncology (2017) 10:116).*
USPTO , TC1600 , BCPM Kolker "Antibodies and the written description requirement of 35 U.S.C.112(a)" pp. 1-36 (Sep. 17, 2020).*
Chang, Lung-Ji, Combination CAR-T Cell Therapy Targeting Hematological Malignancies. Clinical Trials NCT03125577; https://clinicaltrials.gov/ct2/show/NCT03125577 (2017).
Krishnamurthy et al., Bispecific antibodies for cancer therapy: a review. Pharmacol Ther. 185:122-134 (2018).
PCT/US2021/019685 International Search Report and Written Opinion dated Jun. 14, 2021.

(Continued)

*Primary Examiner* — Lynn A Bristol
(74) *Attorney, Agent, or Firm* — Wilson Sonsini Goodrich & Rosati

(57) ABSTRACT

Provided are anti-CD19 and anti-CD38 common light chain bispecific antibodies. The anti-CD19 and anti-CD38 bispecific antibodies described herein are useful in methods for treating a cancer or a tumor.

17 Claims, 30 Drawing Sheets

Specification includes a Sequence Listing.

(56) References Cited

OTHER PUBLICATIONS

Suurs et al., A review of bispecific antibodies and antibody constructs in oncology and clinical challenges. Pharmacol Ther. 201:103-119 (2019).
Timmers et al., Chimeric antigen receptor-modified T cell therapy in multiple myeloma: beyond B cell maturation antigen. Front Immunol. 10:1613. doi: 10.3389/fimmu.2019.01613 (2019).
Altschul et al.: Gapped BLAST and PSI-BLAST: anew generation of protein database search programs. Nucleic acids research vol. 25,17 (1997): 3389-402. doi:10.1093/nar/25.17.3389 .
Deyoung. Development of pancreatic enzyme microsphere technology and US findings with Pancrease in the treatment of chronic pancreatitis. Int J Pancreatol 5 Suppl:31-36 (1989).
Eissler et al.: Abstract 3812: A best in class anti-CD38 antibody with antitumor and immune-modulatory properties. DOI: 10.1158/1538-7445.AM2018-3812 Published Jul. 2018 (htttps://cancerres.aacrjournals.org/content/78/13_Supplement/3812).
Karlin et al.: Applications and statistics formultiple high-scoring segments in molecular sequences. Proceedings of theNational Academy of Sciences Jun. 1993, 90 (12) 5873-5877. DOI:10.1073/pnas.90.12.5873.
Klein et al.: Progress in overcoming the chain association issue in bispecific heterodimeric IgG antibodies. mAbs. 4(6):653-663 (2012).
Miller et al. Design, Construction, and In Vitro Analyses of Multivalent Antibodies. The Journal of Immunology 170:4854-4861 (2003).
Ridgway et al.: 'Knobs-into-holes' engineering of antibody CH3 domains for heavy chain heterodimerization.Protein Engineering. 9(7):617-621 (1996).
Santos et al.: Development of More Efficacious Antibodies for Medical Therapy and Diagnosis. 60:169-194 (1998).

\* cited by examiner

Common Light Chain Bispecific IgG

Fab-Fc:scFv-Fc Bispecific IgG

Fab-Fc-Fab:Fc Bispecific IgG

Fab-Fc-scFv:Fab-Fc-scFv Bispecific IgG

Fab-Fc-scFv:Fc Bispecific IgG

Fab-Fc-Fab:Fab-Fc Bispecific IgG scFv-Fab-Fc:scFv-Fab-Fc Bispecific IgG

Fab-Fab-Fc:Fab-Fab-Fc Bispecific IgG

Fab-Fc-Fab:Fab-Fc-Fab Bispecific IgG

Fab-Fc-scFv:Fab-Fc Bispecific IgG scFv-Fab-Fc:Fc Bispecific IgG

SEQUENCE LISTING

<160> NUMBER OF SEQ ID NOS: 230

<210> SEQ ID NO 1
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser
        115                 120

<210> SEQ ID NO 2
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Arg Tyr Pro Tyr
                 85                  90                  95

Thr Phe Gly Gln Gly Thr Lys Leu Glu Ile Lys
           100                 105

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ser
 1               5                  10                  15

Ser Val Lys Val Ser Cys Lys Ala Ser Gly Thr Phe Ser Ser Tyr
             20                  25                  30

Ala Phe Ser Trp Val Arg Gln Ala Pro Gly Gln Gly Leu Glu Trp Met
             35                  40                  45

Gly Arg Val Ile Pro Phe Leu Gly Ile Ala Asn Ser Ala Gln Lys Phe
         50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Asp Ile Ala Ala Leu Gly Pro Phe Asp Tyr Trp Gly Gln
                100                 105                 110

Gly Thr Leu Val Thr Val Ser Ser
            115                 120

<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95
```

```
Thr Phe Gly Gln Gly Thr Lys Val Glu Ile Lys
            100                 105
```

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120
```

<210> SEQ ID NO 6
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Leu Val Thr Val Ser Ser
        115                 120
```

<210> SEQ ID NO 7
<211> LENGTH: 123
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gly Gly Thr Leu Val Thr Val Ser Ser
            115                 120

```
<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11
```

Gly Gly Thr Phe Ser Ser Tyr Thr
1               5

```
<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12
```

```
Ser Tyr Thr Ile Asn
1               5

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Thr Phe Ser Ser Tyr
1               5

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Ser Tyr Thr Ile Asn
1               5

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Thr Phe Ser Ser Tyr Thr Ile Asn
1               5                   10

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
```

```
<400> SEQUENCE: 20

000

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Ile Pro Ile Phe Gly Ile Pro
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Ile Pro Ile Phe Gly Ile Pro Asn Tyr Ala Gln Lys Phe Gln
1               5                   10                  15

Gly

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Pro Ile Phe Gly
1

<210> SEQ ID NO 24
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Trp Met Gly Gly Ile Ile Pro Ile Phe Gly Ile Pro Asn
1               5                   10

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25
```

Gly Ile Ile Pro Ile Phe Gly Ile Pro Asn
1               5                   10

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Arg Ala Ser Gly Gly Ser Ala Asp Tyr Ser Tyr Gly Met Asp Val
1               5                   10                  15

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ala Ser Gly Gly Ser Ala Asp Tyr Ser Tyr Gly Met Asp Val
1               5                   10

<210> SEQ ID NO 33
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

```
Ser Gly Gly Ser Ala Asp Tyr Ser Tyr Gly Met Asp
1               5                   10
```

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

```
Ala Arg Ala Ser Gly Gly Ser Ala Asp Tyr Ser Tyr Gly Met Asp
1               5                   10                  15
```

<210> SEQ ID NO 35
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

```
Ala Ser Gly Gly Ser Ala Asp Tyr Ser Tyr Gly Met Asp Val
1               5                   10
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 41

Gln Gly Ile Ser Ser Trp Leu Ala
1               5

<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg Ala Ser Gln Gly Ile Ser Ser Trp Leu Ala
1               5                   10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Gln Gly Ile Ser Ser Trp
1               5

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ser Ser Trp Leu Ala Trp Tyr
1               5

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ala Ser Gln Gly Ile Ser Ser Trp Leu Ala
1               5                   10

<210> SEQ ID NO 46

<400> SEQUENCE: 46

000

<210> SEQ ID NO 47

<400> SEQUENCE: 47

000
```

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ala Ala Ser
1

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Ala Ser Ser Leu Gln Ser
1               5

<210> SEQ ID NO 53
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ala Ala Ser
1

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Leu Ile Tyr Ala Ala Ser Ser Leu Gln

```
<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ala Ala Ser Ser Leu Gln Ser
1               5

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Gln Tyr Lys Arg Tyr Pro Tyr Thr
1               5

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62
```

```
Gln Gln Tyr Lys Arg Tyr Pro Tyr Thr
1               5
```

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

```
Tyr Lys Arg Tyr Pro Tyr
1               5
```

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

```
Gln Gln Tyr Lys Arg Tyr Pro Tyr
1               5
```

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

```
Gln Gln Tyr Lys Arg Tyr Pro Tyr Thr
1               5
```

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

```
<400> SEQUENCE: 70

000

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Gly Thr Phe Ser Ser Tyr Ala
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ser Tyr Ala Phe Ser
1               5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Gly Thr Phe Ser Ser Tyr
1               5

<210> SEQ ID NO 74
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ser Ser Tyr Ala Phe Ser
1               5

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Gly Thr Phe Ser Ser Tyr Ala Phe Ser
1               5                   10
```

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Val Ile Pro Phe Leu Gly Ile Ala
1               5

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Arg Val Ile Pro Phe Leu Gly Ile Ala Asn Ser Ala Gln Lys Phe Gln
1               5                   10                  15

Gly

<210> SEQ ID NO 83
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Pro Phe Leu Gly
1

<210> SEQ ID NO 84
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Trp Met Gly Arg Val Ile Pro Phe Leu Gly Ile Ala Asn
1               5                   10

<210> SEQ ID NO 85
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Arg Val Ile Pro Phe Leu Gly Ile Ala Asn
1               5                   10

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ala Arg Asp Asp Ile Ala Ala Leu Gly Pro Phe Asp Tyr
1               5                   10

<210> SEQ ID NO 92
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asp Asp Ile Ala Ala Leu Gly Pro Phe Asp Tyr
1               5                   10

<210> SEQ ID NO 93
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Asp Ile Ala Ala Leu Gly Pro Phe Asp
1               5

<210> SEQ ID NO 94
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ala Arg Asp Asp Ile Ala Ala Leu Gly Pro Phe Asp
1               5                   10

<210> SEQ ID NO 95
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asp Asp Ile Ala Ala Leu Gly Pro Phe Asp Tyr
1               5                   10

<210> SEQ ID NO 96

<400> SEQUENCE: 96

000

<210> SEQ ID NO 97

<400> SEQUENCE: 97

000

```
<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Gly Ile Ser Ser Trp Leu Ala
1               5

<210> SEQ ID NO 102
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg Ala Ser Gln Gly Ile Ser Ser Trp Leu Ala
1               5                   10

<210> SEQ ID NO 103
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ser Gln Gly Ile Ser Ser Trp
1               5

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ser Ser Trp Leu Ala Trp Tyr
1               5
```

```
<210> SEQ ID NO 105
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Arg Ala Ser Gln Gly Ile Ser Ser Trp Leu Ala
1               5                   10

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Ala Ala Ser
1

<210> SEQ ID NO 112
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Ala Ala Ser Ser Leu Gln Ser
```

<210> SEQ ID NO 113
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Ala Ala Ser
1

<210> SEQ ID NO 114
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ser Leu Ile Tyr Ala Ala Ser Ser Leu Gln
1               5                   10

<210> SEQ ID NO 115
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ala Ala Ser Ser Leu Gln Ser
1               5

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Gln Gln Tyr Asn Ser Tyr Pro Arg Thr
1               5

<210> SEQ ID NO 122
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Gln Gln Tyr Asn Ser Tyr Pro Arg Thr
1               5

<210> SEQ ID NO 123
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Tyr Asn Ser Tyr Pro Arg
1               5

<210> SEQ ID NO 124
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gln Gln Tyr Asn Ser Tyr Pro Arg
1               5

<210> SEQ ID NO 125
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gln Gln Tyr Asn Ser Tyr Pro Arg Thr
1               5

```
<210> SEQ ID NO 126
<400> SEQUENCE: 126
000

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
```

```
<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148
```

000

<210> SEQ ID NO 149

<400> SEQUENCE: 149

000

<210> SEQ ID NO 150
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 150

Pro Xaa Leu Gly Xaa Ala
1               5

<210> SEQ ID NO 151
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Pro Phe Leu Gly Thr Ala
1               5

<210> SEQ ID NO 152
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Pro His Leu Gly Ile Ala
1               5

<210> SEQ ID NO 153
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Pro His Leu Gly Thr Ala
1               5

<210> SEQ ID NO 154

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Pro Gln Leu Gly Ile Ala
1               5

<210> SEQ ID NO 155
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Pro Gln Leu Gly Thr Ala
1               5

<210> SEQ ID NO 156
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Q" or "T" or "N" or "S" or "G" or "A"
      or "R" or "K" or "D" or "E"
<220> FEATURE:
<221> NAME/KEY: VARIANT
<222> LOCATION: (5)..(5)
<223> OTHER INFORMATION: /replace="Q" or "T" or "N" or "S" or "G" or "A"
      or "R" or "K" or "D" or "E"
<220> FEATURE:
<221> NAME/KEY: SITE
<222> LOCATION: (1)..(6)
<223> OTHER INFORMATION: /note="Variant residues given in the sequence
      have no preference with respect to those in the annotations
      for variant positions"

<400> SEQUENCE: 156

Pro His Leu Gly His Ala
1               5

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000
```

-continued

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

```
<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179
<400> SEQUENCE: 179
000

<210> SEQ ID NO 180
<400> SEQUENCE: 180
000

<210> SEQ ID NO 181
<400> SEQUENCE: 181
000

<210> SEQ ID NO 182
```

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 201

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
```

85                  90                  95
Ala Arg Ala Ser Gly Gly Ser Ala Asp Tyr Ser Tyr Gly Met Asp Val
              100                 105                 110

Trp Gly Gln Gly Thr Ala Val Thr Val Ser Ser Ala Ser Thr Lys Gly
              115                 120                 125

Pro Ser Val Phe Pro Leu Ala Pro Ser Ser Lys Ser Thr Ser Gly Gly
              130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
              165                 170                 175

Pro Ala Val Leu Gln Ser Ser Gly Leu Tyr Ser Leu Ser Ser Val Val
              180                 185                 190

Thr Val Pro Ser Ser Ser Leu Gly Thr Gln Thr Tyr Ile Cys Asn Val
              195                 200                 205

Asn His Lys Pro Ser Asn Thr Lys Val Asp Lys Lys Val Glu Pro Lys
              210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
              245                 250                 255

Leu Met Ile Ser Arg Thr Pro Glu Val Thr Cys Val Val Val Asp Val
              260                 265                 270

Ser His Glu Asp Pro Glu Val Lys Phe Asn Trp Tyr Val Asp Gly Val
              275                 280                 285

Glu Val His Asn Ala Lys Thr Lys Pro Arg Glu Glu Gln Tyr Asn Ser
              290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
              325                 330                 335

Pro Ile Glu Lys Thr Ile Ser Lys Ala Lys Gly Gln Pro Arg Glu Pro
              340                 345                 350

Gln Val Tyr Thr Leu Pro Pro Ser Arg Asp Glu Leu Thr Lys Asn Gln
              355                 360                 365

Val Ser Leu Ser Cys Ala Val Lys Gly Phe Tyr Pro Ser Asp Ile Ala
              370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
              405                 410                 415

Thr Val Asp Lys Ser Arg Trp Gln Gln Gly Asn Val Phe Ser Cys Ser
              420                 425                 430

Val Met His Glu Ala Leu His Asn His Tyr Thr Gln Lys Ser Leu Ser
              435                 440                 445

Leu Ser Pro Gly Lys
         450

<210> SEQ ID NO 202
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 202

| | | | | | | | | | | | | | | |
|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ser|
|1| | | |5| | | | |10| | | | |15| |
|Ser|Val|Lys|Val|Ser|Cys|Lys|Ala|Ser|Gly|Gly|Thr|Phe|Ser|Ser|Tyr|
| | | |20| | | | |25| | | | |30| | |
|Ala|Phe|Ser|Trp|Val|Arg|Gln|Ala|Pro|Gly|Gln|Gly|Leu|Glu|Trp|Met|
| | |35| | | | |40| | | | |45| | | |
|Gly|Arg|Val|Ile|Pro|Phe|Leu|Gly|Ile|Ala|Asn|Ser|Ala|Gln|Lys|Phe|
| |50| | | | |55| | | | |60| | | | |
|Gln|Gly|Arg|Val|Thr|Ile|Thr|Ala|Asp|Lys|Ser|Thr|Ser|Thr|Ala|Tyr|
|65| | | | |70| | | | |75| | | | |80|
|Met|Asp|Leu|Ser|Ser|Leu|Arg|Ser|Glu|Asp|Thr|Ala|Val|Tyr|Tyr|Cys|
| | | | |85| | | | |90| | | | |95| |
|Ala|Arg|Asp|Asp|Ile|Ala|Ala|Leu|Gly|Pro|Phe|Asp|Tyr|Trp|Gly|Gln|
| | | |100| | | | |105| | | | |110| | |
|Gly|Thr|Leu|Val|Thr|Val|Ser|Ser|Ala|Ser|Thr|Lys|Gly|Pro|Ser|Val|
| | |115| | | | |120| | | | |125| | | |
|Phe|Pro|Leu|Ala|Pro|Ser|Ser|Lys|Ser|Thr|Ser|Gly|Gly|Thr|Ala|Ala|
| |130| | | | |135| | | | |140| | | | |
|Leu|Gly|Cys|Leu|Val|Lys|Asp|Tyr|Phe|Pro|Glu|Pro|Val|Thr|Val|Ser|
|145| | | | |150| | | | |155| | | | |160|
|Trp|Asn|Ser|Gly|Ala|Leu|Thr|Ser|Gly|Val|His|Thr|Phe|Pro|Ala|Val|
| | | | |165| | | | |170| | | | |175| |
|Leu|Gln|Ser|Ser|Gly|Leu|Tyr|Ser|Leu|Ser|Ser|Val|Val|Thr|Val|Pro|
| | | |180| | | | |185| | | | |190| | |
|Ser|Ser|Ser|Leu|Gly|Thr|Gln|Thr|Tyr|Ile|Cys|Asn|Val|Asn|His|Lys|
| | |195| | | | |200| | | | |205| | | |
|Pro|Ser|Asn|Thr|Lys|Val|Asp|Lys|Lys|Val|Glu|Pro|Lys|Ser|Cys|Asp|
| |210| | | | |215| | | | |220| | | | |
|Lys|Thr|His|Thr|Cys|Pro|Pro|Cys|Pro|Ala|Pro|Glu|Leu|Leu|Gly|Gly|
|225| | | | |230| | | | |235| | | | |240|
|Pro|Ser|Val|Phe|Leu|Phe|Pro|Pro|Lys|Pro|Lys|Asp|Thr|Leu|Met|Ile|
| | | | |245| | | | |250| | | | |255| |
|Ser|Arg|Thr|Pro|Glu|Val|Thr|Cys|Val|Val|Val|Asp|Val|Ser|His|Glu|
| | | |260| | | | |265| | | | |270| | |
|Asp|Pro|Glu|Val|Lys|Phe|Asn|Trp|Tyr|Val|Asp|Gly|Val|Glu|Val|His|
| | |275| | | | |280| | | | |285| | | |
|Asn|Ala|Lys|Thr|Lys|Pro|Arg|Glu|Glu|Gln|Tyr|Asn|Ser|Thr|Tyr|Arg|
| |290| | | | |295| | | | |300| | | | |
|Val|Val|Ser|Val|Leu|Thr|Val|Leu|His|Gln|Asp|Trp|Leu|Asn|Gly|Lys|
|305| | | | |310| | | | |315| | | | |320|
|Glu|Tyr|Lys|Cys|Lys|Val|Ser|Asn|Lys|Ala|Leu|Pro|Ala|Pro|Ile|Glu|
| | | | |325| | | | |330| | | | |335| |
|Lys|Thr|Ile|Ser|Lys|Ala|Lys|Gly|Gln|Pro|Arg|Glu|Pro|Gln|Val|Tyr|
| | | |340| | | | |345| | | | |350| | |
|Thr|Leu|Pro|Pro|Ser|Arg|Asp|Glu|Leu|Thr|Lys|Asn|Gln|Val|Ser|Leu|
| | |355| | | | |360| | | | |365| | | |
|Trp|Cys|Leu|Val|Lys|Gly|Phe|Tyr|Pro|Ser|Asp|Ile|Ala|Val|Glu|Trp|
| |370| | | | |375| | | | |380| | | | |
|Glu|Ser|Asn|Gly|Gln|Pro|Glu|Asn|Asn|Tyr|Lys|Thr|Thr|Pro|Pro|Val|
|385| | | | |390| | | | |395| | | | |400|

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly Lys
    450

<210> SEQ ID NO 203
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Glu Lys Ala Pro Lys Ser Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Lys Arg Tyr Pro Tyr Thr Phe Gly Gln Gly Thr
225                 230                 235                 240

Lys Leu Glu Ile Lys Ala Ala Glu Pro Lys Ser Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu

```
            290                 295                 300
Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 204
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175
```

```
Lys Pro Glu Lys Ala Pro Lys Ser Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Lys Arg Tyr Pro Tyr Thr Phe Gly Gln Gly Thr
225                 230                 235                 240

Lys Leu Glu Ile Lys Gly Gly Gly Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
                340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Ser Cys Ala Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Val Ser Lys Leu Thr Val Asp Lys Ser Arg Trp Gln Gln
    435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 205
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45
```

```
Gly Arg Val Ile Pro Phe Leu Gly Ile Ala Asn Ser Ala Gln Lys Phe
 50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Asp Ile Ala Ala Leu Gly Pro Phe Asp Tyr Trp Gly Gln
            100                 105                 110

Gly Thr Leu Val Thr Val Ser Gly Gly Gly Ser Gly Gly Gly
            115                 120                 125

Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Gly Ile Ser Ser Trp Leu Ala Trp Tyr Gln Lys Pro Glu
                165                 170                 175

Lys Ala Pro Lys Ser Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
210                 215                 220

Gln Tyr Asn Ser Tyr Pro Arg Thr Phe Gly Gln Gly Thr Lys Val Glu
225                 230                 235                 240

Ile Lys Ala Ala Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
            370                 375                 380

Asp Glu Leu Thr Lys Asn Gln Val Ser Leu Trp Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
```

<210> SEQ ID NO 206
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 206

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Gly Ile Ser Ser Trp Leu Ala Trp Tyr Gln Gln Lys Pro Glu
                165                 170                 175

Lys Ala Pro Lys Ser Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Tyr Asn Ser Tyr Pro Arg Thr Phe Gly Gln Gly Thr Lys Val Glu
225                 230                 235                 240

Ile Lys Gly Gly Gly Gly Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

```
Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
    370                 375                 380

Thr Lys Asn Gln Val Ser Leu Trp Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470
```

<210> SEQ ID NO 207
<211> LENGTH: 687
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 207

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
            35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220
```

-continued

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Gly Gly Gly Ser Gly Gly Gly Ser Gln Val Gln Leu
450                 455                 460

Val Gln Ser Gly Ala Glu Val Lys Lys Pro Gly Ser Ser Val Lys Val
465                 470                 475                 480

Ser Cys Lys Ala Ser Gly Gly Thr Phe Ser Ser Tyr Ala Phe Ser Trp
                485                 490                 495

Val Arg Gln Ala Pro Gly Gln Gly Leu Glu Trp Met Gly Arg Val Ile
            500                 505                 510

Pro Phe Leu Gly Ile Ala Asn Ser Ala Gln Lys Phe Gln Gly Arg Val
            515                 520                 525

Thr Ile Thr Ala Asp Lys Ser Thr Ser Thr Ala Tyr Met Asp Leu Ser
530                 535                 540

Ser Leu Arg Ser Glu Asp Thr Ala Val Tyr Tyr Cys Ala Arg Asp Asp
545                 550                 555                 560

Ile Ala Ala Leu Gly Pro Phe Asp Tyr Trp Gly Gln Gly Thr Leu Val
                565                 570                 575

Thr Val Ser Ser Ala Ser Thr Lys Gly Pro Ser Val Phe Pro Leu Ala
            580                 585                 590

Pro Ser Ser Lys Ser Thr Ser Gly Gly Thr Ala Ala Leu Gly Cys Leu
            595                 600                 605

Val Lys Asp Tyr Phe Pro Glu Pro Val Thr Val Ser Trp Asn Ser Gly
            610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
```

645                 650                 655

Gly Thr Gln Thr Tyr Ile Cys Asn Val Asn His Lys Pro Ser Asn Thr
            660                 665                 670

Lys Val Asp Lys Lys Val Glu Pro Lys Ser Cys Asp Lys Thr His
        675                 680                 685

<210> SEQ ID NO 208
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 209
<211> LENGTH: 702
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Gln Val Gln Leu Val Gln Ser Gly Ala Glu Val Lys Lys Pro Gly Ser
1               5                   10                  15

-continued

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
            35                  40                  45

Gly Arg Val Ile Pro Phe Leu Gly Ile Ala Asn Ser Ala Gln Lys Phe
 50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
            85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Gly Gly Gly Ser Gly Gly Ser Gln Val Gln Leu Val Gln Ser
        450                 455                 460

Gly Ala Glu Val Lys Lys Pro Gly Ser Ser Val Lys Val Ser Cys Lys
465                 470                 475                 480

Ala Ser Gly Gly Thr Phe Ser Ser Tyr Thr Ile Asn Trp Val Arg Gln
                485                 490                 495

Ala Pro Gly Gln Gly Leu Glu Trp Met Gly Gly Ile Ile Pro Ile Phe
            500                 505                 510

Gly Ile Pro Asn Tyr Ala Gln Lys Phe Gln Gly Arg Val Thr Ile Thr
        515                 520                 525

Ala Asp Glu Ser Thr Asn Thr Ala Tyr Met Glu Leu Ser Ser Leu Arg
    530                 535                 540

Ala Glu Asp Thr Ala Val Tyr Tyr Cys Ala Arg Ala Ser Gly Gly Ser
545                 550                 555                 560

Ala Asp Tyr Ser Tyr Gly Met Asp Val Trp Gly Gln Gly Thr Ala Val
                565                 570                 575

Thr Val Ser Ser Gly Gly Gly Gly Ser Gly Gly Gly Ser Gly Gly
            580                 585                 590

Gly Gly Ser Asp Ile Gln Met Thr Gln Ser Pro Ser Ser Leu Ser Ala
        595                 600                 605

Ser Val Gly Asp Arg Val Thr Ile Thr Cys Arg Ala Ser Gln Gly Ile
    610                 615                 620

Ser Ser Trp Leu Ala Trp Tyr Gln Gln Lys Pro Glu Lys Ala Pro Lys
625                 630                 635                 640

Ser Leu Ile Tyr Ala Ala Ser Ser Leu Gln Ser Gly Val Pro Ser Arg
                645                 650                 655

Phe Ser Gly Ser Gly Ser Gly Thr Asp Phe Thr Leu Thr Ile Ser Ser
            660                 665                 670

Leu Gln Pro Glu Asp Phe Ala Thr Tyr Tyr Cys Gln Gln Tyr Lys Arg
        675                 680                 685

Tyr Pro Tyr Thr Phe Gly Gln Gly Thr Lys Leu Glu Ile Lys
    690                 695                 700

<210> SEQ ID NO 210
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Arg Tyr Pro Tyr

```
                    85                  90                  95
Thr Phe Gly Gln Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 211
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 211

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Arg
                85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 212
<211> LENGTH: 703
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 212

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Glu Lys Ala Pro Lys Ser Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Lys Arg Tyr Pro Tyr Thr Phe Gly Gln Gly Thr
225                 230                 235                 240

Lys Leu Glu Ile Lys Gly Gly Gly Gly Gln Val Gln Leu Val Gln
                245                 250                 255

Ser Gly Ala Glu Val Lys Lys Pro Gly Ser Ser Val Lys Val Ser Cys
            260                 265                 270

Lys Ala Ser Gly Gly Thr Phe Ser Ser Tyr Thr Ile Asn Trp Val Arg
        275                 280                 285

Gln Ala Pro Gly Gln Gly Leu Glu Trp Met Gly Gly Ile Ile Pro Ile
    290                 295                 300

Phe Gly Ile Pro Asn Tyr Ala Gln Lys Phe Gln Gly Arg Val Thr Ile
305                 310                 315                 320

Thr Ala Asp Glu Ser Thr Asn Thr Ala Tyr Met Glu Leu Ser Ser Leu
                325                 330                 335

Arg Ala Glu Asp Thr Ala Val Tyr Tyr Cys Ala Arg Ala Ser Gly Gly
            340                 345                 350
```

```
Ser Ala Asp Tyr Ser Tyr Gly Met Asp Val Trp Gly Gln Gly Thr Ala
        355                 360                 365
Val Thr Val Ser Ser Ala Ser Thr Lys Gly Pro Ser Val Phe Pro Leu
370                 375                 380
Ala Pro Ser Ser Lys Ser Thr Ser Gly Gly Thr Ala Ala Leu Gly Cys
385                 390                 395                 400
Leu Val Lys Asp Tyr Phe Pro Glu Pro Val Thr Val Ser Trp Asn Ser
                405                 410                 415
Gly Ala Leu Thr Ser Gly Val His Thr Phe Pro Ala Val Leu Gln Ser
            420                 425                 430
Ser Gly Leu Tyr Ser Leu Ser Ser Val Val Thr Val Pro Ser Ser Ser
        435                 440                 445
Leu Gly Thr Gln Thr Tyr Ile Cys Asn Val Asn His Lys Pro Ser Asn
    450                 455                 460
Thr Lys Val Asp Lys Lys Val Glu Pro Lys Ser Cys Asp Lys Thr His
465                 470                 475                 480
Thr Cys Pro Pro Cys Pro Ala Pro Glu Leu Leu Gly Gly Pro Ser Val
                485                 490                 495
Phe Leu Phe Pro Pro Lys Pro Lys Asp Thr Leu Met Ile Ser Arg Thr
            500                 505                 510
Pro Glu Val Thr Cys Val Val Val Asp Val Ser His Glu Asp Pro Glu
        515                 520                 525
Val Lys Phe Asn Trp Tyr Val Asp Gly Val Glu Val His Asn Ala Lys
    530                 535                 540
Thr Lys Pro Arg Glu Glu Gln Tyr Asn Ser Thr Tyr Arg Val Val Ser
545                 550                 555                 560
Val Leu Thr Val Leu His Gln Asp Trp Leu Asn Gly Lys Glu Tyr Lys
                565                 570                 575
Cys Lys Val Ser Asn Lys Ala Leu Pro Ala Pro Ile Glu Lys Thr Ile
            580                 585                 590
Ser Lys Ala Lys Gly Gln Pro Arg Glu Pro Gln Val Tyr Thr Leu Pro
        595                 600                 605
Pro Ser Arg Asp Glu Leu Thr Lys Asn Gln Val Ser Leu Trp Cys Leu
    610                 615                 620
Val Lys Gly Phe Tyr Pro Ser Asp Ile Ala Val Glu Trp Glu Ser Asn
625                 630                 635                 640
Gly Gln Pro Glu Asn Asn Tyr Lys Thr Thr Pro Pro Val Leu Asp Ser
                645                 650                 655
Asp Gly Ser Phe Phe Leu Tyr Ser Lys Leu Thr Val Asp Lys Ser Arg
            660                 665                 670
Trp Gln Gln Gly Asn Val Phe Ser Cys Ser Val Met His Glu Ala Leu
        675                 680                 685
His Asn His Tyr Thr Gln Lys Ser Leu Ser Leu Ser Pro Gly Lys
    690                 695                 700

<210> SEQ ID NO 213
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Asp Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Gly Ile Ser Ser Trp
                20                  25                 30

Leu Ala Trp Tyr Gln Gln Lys Pro Glu Lys Ala Pro Lys Ser Leu Ile
            35                  40                 45

Tyr Ala Ala Ser Ser Leu Gln Ser Gly Val Pro Ser Arg Phe Ser Gly
            50                  55                 60

Ser Gly Ser Gly Thr Asp Phe Thr Leu Thr Ile Ser Ser Leu Gln Pro
65                  70                  75                 80

Glu Asp Phe Ala Thr Tyr Tyr Cys Gln Gln Tyr Asn Ser Tyr Pro Arg
                85                  90                 95

Thr Phe Gly Gln Gly Thr Lys Val Glu Ile Lys Arg Thr Val Ala Ala
                100                 105                110

Pro Ser Val Phe Ile Phe Pro Pro Ser Asp Glu Gln Leu Lys Ser Gly
                115                 120                125

Thr Ala Ser Val Val Cys Leu Leu Asn Asn Phe Tyr Pro Arg Glu Ala
            130                 135                140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
            180                 185                190

Ala Cys Glu Val Thr His Gln Gly Leu Ser Ser Pro Val Thr Lys Ser
                195                 200                205

Phe Asn Arg Gly Glu Cys
            210

<210> SEQ ID NO 214
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Asp Lys Thr His Thr Cys Pro Pro Cys Pro Ala Pro Glu Leu Leu Gly
1               5                   10                 15

Gly Pro Ser Val Phe Leu Phe Pro Pro Lys Pro Lys Asp Thr Leu Met
            20                  25                 30

Ile Ser Arg Thr Pro Glu Val Thr Cys Val Val Val Asp Val Ser His
            35                  40                 45

Glu Asp Pro Glu Val Lys Phe Asn Trp Tyr Val Asp Gly Val Glu Val
        50                  55                 60

His Asn Ala Lys Thr Lys Pro Arg Glu Glu Gln Tyr Asn Ser Thr Tyr
65                  70                  75                 80

Arg Val Val Ser Val Leu Thr Val Leu His Gln Asp Trp Leu Asn Gly
                85                  90                 95

Lys Glu Tyr Lys Cys Lys Val Ser Asn Lys Ala Leu Pro Ala Pro Ile
                100                 105                110

Glu Lys Thr Ile Ser Lys Ala Lys Gly Gln Pro Arg Glu Pro Gln Val
            115                 120                125

Tyr Thr Leu Pro Pro Ser Arg Asp Glu Leu Thr Lys Asn Gln Val Ser
            130                 135                140
```

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 215
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 216
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
```

```
                145                 150                 155                 160
        Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                        180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Val Glu Pro Lys
                        210                 215                 220

Ser Cys Asp Lys Thr His Thr Cys Pro Pro Cys Pro Ala Pro Glu Leu
        225                 230                 235                 240

Leu Gly Gly Pro Ser Val Phe Leu Phe Pro Pro Lys Pro Lys Asp Thr
                        245                 250                 255

Leu Met Ile Ser Arg Thr Pro Glu Val Thr Cys Val Val Val Asp Val
                        260                 265                 270

Ser His Glu Asp Pro Glu Val Lys Phe Asn Trp Tyr Val Asp Gly Val
                        275                 280                 285

Glu Val His Asn Ala Lys Thr Lys Pro Arg Glu Glu Gln Tyr Asn Ser
                        290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                        325                 330                 335

Pro Ile Glu Lys Thr Ile Ser Lys Ala Lys Gly Gln Pro Arg Glu Pro
                        340                 345                 350

Gln Val Tyr Thr Leu Pro Pro Ser Arg Asp Glu Leu Thr Lys Asn Gln
                        355                 360                 365

Val Ser Leu Ser Cys Ala Val Lys Gly Phe Tyr Pro Ser Asp Ile Ala
                        370                 375                 380

Val Glu Trp Glu Ser Asn Gly Gln Pro Glu Asn Asn Tyr Lys Thr Thr
        385                 390                 395                 400

Pro Pro Val Leu Asp Ser Asp Gly Ser Phe Phe Leu Val Ser Lys Leu
                        405                 410                 415

Thr Val Asp Lys Ser Arg Trp Gln Gln Gly Asn Val Phe Ser Cys Ser
                        420                 425                 430

Val Met His Glu Ala Leu His Asn His Tyr Thr Gln Lys Ser Leu Ser
                        435                 440                 445

Leu Ser Pro Gly Lys
            450

<210> SEQ ID NO 217
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Ser Tyr
                        20                  25                  30

Thr Ile Asn Trp Val Arg Gln Ala Pro Gly Gln Gly Leu Glu Trp Met
                        35                  40                  45
```

```
Gly Gly Ile Ile Pro Ile Phe Gly Ile Pro Asn Tyr Ala Gln Lys Phe
    50              55                  60

Gln Gly Arg Val Thr Ile Thr Ala Asp Glu Ser Thr Asn Thr Ala Tyr
65              70                  75                  80

Met Glu Leu Ser Ser Leu Arg Ser Glu Asp Thr Ala Val Tyr Tyr Cys
            85                  90                  95

Ala Arg Ala Ser Gly Gly Ser Ala Asp Tyr Ser Tyr Gly Met Asp Val
                100                 105                 110

Trp Gly Gly Gly Thr Leu Val Thr Val Ser Ser Gly Gly Gly Gly Ser
    115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Glu Lys Ala Pro Lys Ser Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Lys Arg Tyr Pro Tyr Thr Phe Gly Gln Gly Thr
225                 230                 235                 240

Lys Leu Glu Ile Lys Ala Ala Glu Pro Lys Ser Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Lys Leu Thr Val Asp Lys Ser Arg
        435                 440                 445

Trp Gln Gln Gly Asn Val Phe Ser Cys Ser Val Met His Glu Ala Leu
    450                 455                 460
```

-continued

His Asn His Tyr Thr Gln Lys Ser Leu Ser Leu Ser Pro Gly Lys
465                 470                 475

<210> SEQ ID NO 218
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Thr Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120

<210> SEQ ID NO 219
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro His Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120

<210> SEQ ID NO 220
<211> LENGTH: 120
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 220

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Phe Ser Trp Val Arg Gln Ala Pro Gly Gln Gly Leu Glu Trp Met
        35                  40                  45
Gly Arg Val Ile Pro His Leu Gly Thr Ala Asn Ser Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Asp Ile Ala Ala Leu Gly Pro Phe Asp Tyr Trp Gly Gln
            100                 105                 110
Gly Thr Leu Val Thr Val Ser Ser
        115                 120

<210> SEQ ID NO 221
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 221

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Phe Ser Trp Val Arg Gln Ala Pro Gly Gln Gly Leu Glu Trp Met
        35                  40                  45
Gly Arg Val Ile Pro Gln Leu Gly Ile Ala Asn Ser Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Asp Ile Ala Ala Leu Gly Pro Phe Asp Tyr Trp Gly Gln
            100                 105                 110
Gly Thr Leu Val Thr Val Ser Ser
        115                 120

<210> SEQ ID NO 222
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 222

```
Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
            35                  40                  45

Gly Arg Val Ile Pro Gln Leu Gly Thr Ala Asn Ser Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120
```

<210> SEQ ID NO 223
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 223

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser His
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105
```

<210> SEQ ID NO 224
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 224

```
Gly Ser Gly Gly Ser
1               5
```

<210> SEQ ID NO 225
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 225

Gly Gly Gly Gly Ser
1               5

<210> SEQ ID NO 226
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Gly Gly Ser
1

<210> SEQ ID NO 227
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Ala Ala Glu Pro Lys Ser Ser
1               5

<210> SEQ ID NO 228
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ala Ala Glu Pro Lys Ser Ser Asp Lys Thr His Thr Cys Pro Pro Cys
1               5                   10                  15

Pro

<210> SEQ ID NO 229
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Gly Gly Gly Gly
1
```

```
<210> SEQ ID NO 230
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gly Gly Gly Gly Asp Lys Thr His Thr Cys Pro Pro Cys Pro
1               5                   10
```

COMPOSITE BINDING MOLECULES TARGETING IMMUNOSUPPRESSIVE B CELLS

CROSS-REFERENCE

This application is a Continuation of International Application No. PCT/US2021/019685, filed on Feb. 25, 2021, which claims the benefit of U.S. Provisional Application No. 62/981,990 filed on Feb. 26, 2020, U.S. Provisional Application No. 62/990,330 filed on Mar. 16, 2020, and U.S. Provisional Application No. 63/094,838 filed on Oct. 21, 2020, which applications are incorporated herein by reference.

SEQUENCE LISTING

The instant application contains a Sequence Listing which has been submitted electronically in ASCII format and is hereby incorporated by reference in its entirety. Said ASCII copy, created on Mar. 5, 2021, is named 51527-712_301_SL.txt and is 104,266 bytes in size.

BACKGROUND

Antibody therapeutics have been used successfully to treat a variety of diseases; however, their application can be limited with respect to clinical efficacy in complex diseases such as cancer. Engineering antibody-based therapeutics to alter target-binding affinities and valences provides a potential pathway towards achieving increased efficacy and improving treatment outcomes. Bispecific or multivalent antibodies thus offer a potential approach to resolving challenges tied to the multifactorial nature of complex diseases. By binding two different antigenic molecules or different epitopes of the same antigen, bispecific antibodies offer greater functionality and offer a wide variety of applications as targeting agents for the treatment of a number of diseases.

SUMMARY

The dynamic relationship between cancer biology and the immune system is a factor associated with clinical outcomes. The immune response plays a significant role in regulating the tumor microenvironment during cancer development. Immune cells such as T cells and B cells thus act as modulators and effectors of cancer progression or metastasis. Notably, immunosuppressive cells play an important role in the anti-tumor immune response wherein immunosuppression is generally associated with tumor growth and invasion, and correlates with negative outcomes. Although B cells are known to positively modulate the immune response, populations of immunosuppressive B cells function to suppress the anti-tumor immune response thus facilitating tumor growth.

Provided herein are certain binding molecules that target immunosuppressive B-cell populations with bispecific or multivalent targeting molecules. Targeting immune suppressive B-cell populations presents a pathway for therapeutic intervention in cancer that effectively modulates the anti-tumor immune response to improve treatment outcomes (e.g. in contrast to selective depletion of an epithelial cancer cell population). The binding molecules provided herein can comprise a bispecific antibody that binds to a B-cell lineage surface marker (e.g., CD19, CD138, IgA, and/or CD20) and a surface marker of immunosuppressive B cells (e.g., IgD, CD1, CD5, CD21, CD24, CD38, HM13, SLAMF7, AQP3, and/or latent TGF-beta (e.g., TGF-beta LAP)). In a certain specific embodiment, the bispecific antibody binds to CD19 and CD38, thus possessing selectivity for a specific immunosuppressive B-cell population.

As provided and described herein, the bispecific antibodies that bind to CD19 and CD38 provide advantages in the selective binding of cells expressing CD19 and CD38 (e.g. immunosuppressive B-cell populations). Furthermore, the bispecific antibodies, disclosed herein, that bind to CD19 and CD38 demonstrate advantages in that they do not promote hemolysis or hemagglutination, especially when compared to mono-specific CD19 or CD38 antibodies. Thus, overcoming severe side-effects seen with monospecific CD19 or CD38 antibodies (e.g., SARCLISA® (isatuximab-irfc)), such as anemia. Bispecific antibodies that bind to CD19 and CD38 also demonstrate advantages in that they effectively promote advantageous target cell apoptosis of cells expressing CD19 and CD38, especially when compared to mono-specific controls. Furthermore, the bispecific antibodies that bind to CD19 and CD38 further provide advantages over the mere use of two independent monoclonal antibodies independently targeting CD38 and CD19, in that they more effectively target specific immunosuppressive B-cell populations, leading to greater effectiveness and potentially lower side effects seen with other B cell targeting monoclonal antibodies (e.g., Rituximab), such as or lymphopenia.

Described herein is a composite binding molecule comprising a first binding component configured to bind a first target and a second binding component configured to bind a second target, wherein the first target comprises a B-cell lineage surface marker, and wherein the second target comprises an immunosuppressive B-cell surface marker, wherein the first target and the second target are not identical. In some embodiments, the first or the second binding component comprises a polypeptide. In some embodiments, the first or the second binding component consists of a polypeptide. In some embodiments, the first and the second binding component comprise a polypeptide. In some embodiments, the first and the second binding component consist of a polypeptide. In some embodiments, the polypeptide of the first or second binding component comprises an amino acid sequence at least 100 amino acid residues in length. In some embodiments, the polypeptide of the first and second binding component comprise an amino acid sequence at least 100 amino acid residues in length.

In some embodiments, the B-cell lineage surface marker comprises CD19, CD138, IgA, or CD45. In some embodiments, the B-cell lineage surface marker comprises CD19. In some embodiments, the B-cell lineage surface marker consists of CD19. In some embodiments, the immunosuppressive B-cell surface marker comprises IgD, CD1, CD5, CD21, CD24, CD38, HM13, SLAMF7, AQP3, or latent TGF-beta (e.g., TGF-beta LAP). In some embodiments, the immunosuppressive B-cell surface marker comprises CD38. In some embodiments, the immunosuppressive B-cell surface marker consists of CD38.

In some embodiments, the first or second binding component comprise an immunoglobulin heavy and light chain pair, an scFv, a F(ab), a F(ab')2, a single domain antibody, a variable region fragment from an immunoglobulin new antigen receptor ($V_{NAR}$), or a variable region derived from a heavy chain antibody ($V_HH$). In some embodiments, the first and second binding component comprise an immunoglobulin heavy and light chain pair, an scFv, a F(ab), a F(ab')2, a single domain antibody, a variable region fragment from an immunoglobulin new antigen receptor ($V_{NAR}$), or a variable region derived from a heavy chain antibody ($V_HH$).

In some embodiments, the first or second binding component comprises an immunoglobulin heavy and light chain pair. In some embodiments, the first and second binding component comprise an immunoglobulin heavy and light chain pair. In some embodiments, the composite binding molecule comprises an immunoglobulin heavy chain and an immunoglobulin light chain, wherein the immunoglobulin heavy chain comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and an immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In some embodiments, the immunoglobulin heavy chain comprises an amino acid sequence having at least about 90%, 95%, 97%, 99% identity to SEQ ID NO: 3; and the immunoglobulin light chain having at least about 90%, 95%, 97%, 99% identity to SEQ ID NO: 2. In some embodiments, the immunoglobulin heavy chain comprises an amino acid sequence identical to that set forth in SEQ ID NO: 3; and the immunoglobulin light chain comprises an amino acid sequence identical to that set forth in SEQ ID NO: 2. In some embodiments, composite binding molecule is a common light chain bispecific IgG.

In some embodiments, the first or second binding component comprises an scFv. In some embodiments, the first and second binding component comprise an scFv. In some embodiments, the composite binding molecule is a bispecific antibody or dual-antigen binding fragment thereof.

In some embodiments, the bispecific antibody is selected from one of the following formats: a common light chain bispecific IgG, a Fab-Fc:scFv-Fc bispecific IgG, a Fab-Fc-Fab:Fc bispecific IgG, a Fab-Fc-scFv:Fab-Fc-scFv bispecific IgG, a Fab-Fc-scFv:Fc bispecific IgG, a Fab-Fc-Fab:Fab-Fc bispecific IgG, an scFv-Fab-Fc:scFv-Fab-Fc bispecific IgG, a Fab-Fab-Fc:Fab-Fab-Fc bispecific IgG, a Fab-Fc-Fab:Fab-Fc-Fab bispecific IgG, scFv-Fab-Fc:Fc bispecific IgG, and a Fab-Fc-scFv:Fab-Fc bispecific IgG. In some embodiments, the bispecific antibody is a Fab-Fc:scFv-Fc bispecific IgG. In some embodiments, the bispecific antibody is a Fab-Fc-scFv:Fab-Fc-scFv bispecific IgG. In some embodiments, the bispecific antibody is an scFv-Fab-Fc:Fc bispecific IgG. In some embodiments, the composite binding molecule comprises an Fc region comprising a native carbohydrate or an afucosylated carbohydrate modified amino acid residue. In some embodiments, the native carbohydrate or the afucosylated carbohydrate modified amino acid residue corresponds to Asparagine 297 according to EU numbering.

In some embodiments, the first binding component comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35, an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65.

In some embodiments, the first binding component comprises an amino acid sequence comprising at least about 90%, 95%, 97%, 99% identity to, or is 100% identical to the amino acid sequences set forth in any one of SEQ ID NOs: SEQ ID NO: 1 and SEQ ID NO: 2.

In some embodiments, the first binding component comprises an amino acid sequence identical to the amino acid sequences set forth in SEQ ID NO: 1 and SEQ ID NO: 2.

In some embodiments, the second binding component comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95, an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125.

In some embodiments, the second binding component comprises an amino acid sequence comprising at least about 90%, 95%, 97%, 99% identity to, or is 100% identical to the amino acid sequences set forth in any one of SEQ ID NO: 3 and SEQ ID NO: 4. In some embodiments, the second binding component comprises an amino acid sequence identical to the amino acid sequences set forth in SEQ ID NO: SEQ ID NO: 3 and SEQ ID NO: 4.

In some embodiments, the composite binding molecule binds to CD19+, CD38+ B cells.

Disclosed is a cell comprising the nucleic acid encoding a composite binding molecule. In some embodiments, the polynucleotide sequence encoding the composite binding molecule is operatively coupled to a eukaryotic regulatory sequence. In some embodiments, the cell comprises a prokaryotic cell. In some embodiments, the prokaryotic cell is an *Escherichia coli* cell. In some embodiments, the cell comprises a eukaryotic cell. In some embodiments, the eukaryotic cell is a Chinese Hamster Ovary (CHO) cell, an NS0 murine myeloma cell, or a human PER.C6 cell.

Disclosed is a composition comprising a composite binding molecule and a pharmaceutically acceptable diluent, carrier, or excipient. In some embodiments, the composition is formulated for intravenous administration. In some embodiments, the composition is formulated for subcutaneous administration.

Provided are composite binding molecules for use in methods of treating a tumor or a cancer in an individual. In some embodiments, the cancer or the tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

In some embodiments, the cancer or the tumor is a solid-tissue cancer. In some embodiments, the cancer comprises breast cancer, prostate cancer, pancreatic cancer, lung cancer, kidney cancer, stomach cancer, esophageal cancer, skin cancer, colorectal cancer, brain cancer, or head and neck cancer. In some embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma.

Provided are composite binding molecules for use in a method of reducing immunosuppressive B cells in, adjacent to, or surrounding a tumor of an individual or immunosuppressive B cells affecting an anti-tumor immune response of an individual that are distant from the tumor site. Provided are composite binding molecules for use in a method of reducing immunosuppressive B cells in, adjacent to, or surrounding a tumor of an individual. In some embodiments, the tumor infiltrating B cells or the immunosuppressive B cells comprise CD19+CD38+ B cells. Further provided are composite binding molecules for use in a method of reducing or inhibiting the function of immunosuppressive B cells in, adjacent to, or surrounding a tumor of an individual and/or immunosuppressive B cells affecting an anti-tumor immune response of an individual that are distant from a tumor site. In some embodiments, the function of immunosuppressive B cells comprises the release of anti-inflammatory or immunosuppressive cytokines such as IL-10, IL 35, TGF-beta, or a combination thereof Disclosed are methods of treating an individual afflicted with a cancer or a tumor comprising administering to the individual afflicted with the cancer or the tumor the composite binding molecule, thereby treating the cancer or tumor. In some embodiments, the cancer or tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

n some embodiments, the cancer or tumor is a solid-tissue cancer. In some embodiments, the cancer comprises breast cancer, prostate cancer, pancreatic cancer, lung cancer, kidney cancer, stomach cancer, esophageal cancer, skin cancer, colorectal cancer, or head and neck cancer. In some embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma.

Disclosed are methods of reducing immunosuppressing B cells affecting anti-tumor immune responses against a tumor of an individual afflicted with a tumor or cancer comprising administering to the individual afflicted with the tumor or the cancer the composite binding molecule, thereby reducing immunosuppressing B cells affecting the anti-tumor immune responses. Further disclosed are methods of reducing immunosuppressive B cells in, adjacent to, or surrounding a tumor of an individual afflicted with a tumor or cancer comprising administering to the individual afflicted with the tumor or the cancer the composite binding molecule, thereby reducing immunosuppressive B cells in, adjacent to, or surrounding the tumor. In some embodiments, the tumor infiltrating B cells or the immunosuppressive B cells comprise CD19+, CD38+ B cells.

Further disclosed are methods of preparing a cancer treatment for an individual comprising admixing the composite binding molecule with a pharmaceutically acceptable diluent, carrier, or excipient.

Disclosed are also methods of making the composite binding molecule comprising incubating a cell comprising an expression vector that comprises a nucleic acid sequence encoding the composite binding molecule in a cell culture medium under conditions sufficient to allow expression, assembly and secretion of the composite binding molecule into the cell culture medium. In some embodiments, the methods comprise isolating and purifying the molecule from the cell culture medium. Such isolating and purifying can involve a step comprising contacting the cell culture medium or a cell culture medium that has been subjected to one or more purification steps with a resin or column comprising Protein, Protein G, Protein L, Protein A/G, or any combination thereof, and optionally washing the resin or column to remove one or more non-composite binding molecules from the cell culture medium or the cell culture medium that has been subjected to one or more purification steps.

Provided herein are composite binding molecules comprising a CD19 binding component configured to bind CD19 and a CD38 binding component configured to bind CD38, wherein the CD19 binding component comprises an antibody or antigen binding fragment thereof and the CD38 binding component comprises an antibody or antigen binding fragment thereof. In some embodiments, provided is a composite binding molecule of any of the preceding embodiments, wherein the CD19 and/or CD38 binding component comprise an immunoglobulin heavy and light chain pair, an scFv, a F(ab), a F(ab')2, a single domain antibody, a variable region fragment from an immunoglobulin new antigen receptor ($V_{NAR}$), or a variable region derived from a heavy chain antibody ($V_HH$). In some embodiments, provided is a composite binding molecule of any of the preceding embodiments, wherein the CD19 or CD38 binding component comprises an immunoglobulin heavy and light chain pair. In some embodiments, provided is a composite binding molecule of any of the preceding embodiments, wherein the CD19 and CD38 binding component comprise an immunoglobulin heavy and light chain pair.

In some embodiments, provided is a composite binding molecule of any of the preceding embodiments, wherein the CD38 binding component comprises an immunoglobulin heavy chain and an immunoglobulin light chain, wherein the immunoglobulin heavy chain comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125; and wherein the CD19 binding component comprises an immunoglobulin heavy chain and an immunoglobulin light chain, wherein the immunoglobulin heavy chain comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125. In some embodiments, provided is a composite binding molecule of any of the preceding embodiments, wherein the CD 38 binding component comprises an immunoglobulin heavy chain comprising an amino acid sequence having at least about 90%, 95%, 97%, 99% identity to SEQ ID NO: 3; and the immunoglobulin light chain having at least about 90%, 95%, 97%, 99% identity to SEQ ID NO: 4; and/or wherein the CD19 binding component comprises an immunoglobulin heavy chain comprising an amino acid sequence having at least about 90%, 95%, 97%, 99% identity to SEQ ID NO: 1; and an immunoglobulin light chain having at least about 90%, 95%, 97%, 99% identity to SEQ ID NO: 4. In some embodiments, provided is a composite binding molecule of any of the preceding embodiments, wherein the immunoglobulin heavy chain comprises an amino acid sequence identical to that set forth in SEQ ID NO: 3 or 5; and the immunoglobulin light chain comprises an amino acid sequence identical to that set forth in SEQ ID NO: 4; and/or wherein the immunoglobulin heavy chain comprises an amino acid sequence identical to that set forth in SEQ ID NO: 1 or 6; and the immunoglobulin light chain comprises an amino acid sequence identical to that set forth in SEQ ID NO: 4.

In some embodiments, provided is a composite binding molecule of any of the preceding embodiments, wherein the composite binding molecule is a common light chain bispecific IgG. In some embodiments, provided is a composite binding molecule of any of the preceding embodiments, wherein the CD 38 binding component comprises an immunoglobulin heavy chain comprising an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125; and wherein the CD 19 binding component comprises an immunoglobulin heavy chain comprising an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In some embodiments, provided is a composite binding molecule of any of the preceding embodiments, wherein the immunoglobulin heavy chain comprises an amino acid sequence having at least about 90%, 95%, 97%, 99% identity to SEQ ID NO: 3 or 5; and the immunoglobulin light chain having at least about 90%, 95%, 97%, 99% identity to SEQ ID NO: 4; and/or wherein the immunoglobulin heavy chain comprises an amino acid sequence having at least about 90%, 95%, 97%, 99% identity to SEQ ID NO: 1 or 7; and the immunoglobulin light chain having at least about 90%, 95%, 97%, 99% identity to SEQ ID NO: 2.

In some embodiments, provided is a composite binding molecule of any of the preceding embodiments, wherein the immunoglobulin heavy chain comprises an amino acid sequence identical to that set forth in SEQ ID NO: 3 or 5; and the immunoglobulin light chain comprises an amino acid sequence identical to that set forth in SEQ ID NO: 4; and wherein the immunoglobulin heavy chain comprises an amino acid sequence identical to that set forth in SEQ ID NO: 1 or 7; and the immunoglobulin light chain comprises an amino acid sequence identical to that set forth in SEQ ID NO: 2. In some embodiments, provided is a composite binding molecule of any of the preceding embodiments, wherein the CD19 binding component or CD38 binding component comprise an scFv. In some embodiments, provided is a composite binding molecule of any of the preceding embodiments, wherein the CD19 binding component comprises an scFv. In some embodiments, provided is a composite binding molecule of any of the preceding embodiments, wherein the CD38 binding component comprises an scFv. In some embodiments, provided is a composite binding molecule of any of the preceding embodiments, wherein the CD19 binding component or CD38 binding component comprise an immunoglobulin heavy-chain/light chain pair. In some embodiments, provided is a composite binding molecule of any of the preceding embodiments, wherein the CD19 binding component comprises an immunoglobulin heavy-chain/light chain pair. In some embodiments, provided is a composite binding molecule of any of the preceding embodiments, wherein the CD38 binding component comprises an immunoglobulin heavy-chain/light chain pair.

Further provided are composite binding molecules, wherein the composite binding molecule comprises a CD38 antigen binding component that binds CD38 comprising an anti-CD38 immunoglobulin heavy chain variable region paired with an anti-CD38 immunoglobulin light chain variable region and a CD19 antigen binding component that binds CD19 comprising an anti-CD19 immunoglobulin heavy chain variable region paired with an anti-CD38 immunoglobulin light chain variable region, wherein the CD38 antigen binding component comprises: a) a heavy chain complementarity determining region 1 (HCDR1) comprising an amino acid sequence set forth in any one of SEQ ID NOs: 71-75; b) a heavy chain complementarity determining region 2 (HCDR2) comprising an amino acid sequence set forth in any one of SEQ ID NOs: 81-85, or 150-155, c) a heavy chain complementarity determining region 3 (HCDR3) comprising an amino acid sequence set forth in any one of SEQ ID NOs: 91-95; d) a light chain complementarity determining region 1 (LCDR1) comprising an amino acid sequence set forth in any one of SEQ ID NOs: 101-105; e) a light chain complementarity determining region 2 (LCDR2) comprising an amino acid sequence set forth in any one of SEQ ID NOs: 111-115; and/or f) a light chain complementarity determining region 3 (LCDR3) comprising an amino acid sequence set forth in any one of SEQ ID NOs: 121-125.

In some embodiments, provided is a composite binding molecule of any of the preceding embodiments, wherein the CD19 antigen binding component comprises: g) a heavy chain complementarity determining region 1 (HCDR1) comprising an amino acid sequence set forth in any one of SEQ ID NOs: 11-15, h) a heavy chain complementarity determining region 2 (HCDR2) comprising an amino acid sequence set forth in any one of SEQ ID NOs: 21-25, i) a heavy chain complementarity determining region 3 (HCDR3) comprising an amino acid sequence set forth in any one of SEQ ID NOs: 31-35; j) a light chain complementarity determining region 1 (LCDR1) comprising an amino acid sequence set forth in any one of SEQ ID NOs: 101-105; k) a light chain complementarity determining region 2 (LCDR2) comprising an amino acid sequence set forth in any one of SEQ ID NOs: 111-115; and/or 1) a light chain complementarity determining region 3 (LCDR3) comprising an amino acid sequence set forth in any one of SEQ ID NOs: 121-125.

In some embodiments, provided is a composite binding molecule of any of the preceding embodiments, wherein the CD38 antigen binding component comprises an immunoglobulin heavy chain variable region comprising an amino acid sequence having at least about 90%, 95%, 97%, 99% identity to SEQ ID NO: 3 or 5; and an immunoglobulin light chain variable region comprising an amino acid sequence having at least about 90%, 95%, 97%, 99% identity to SEQ ID NO: 4. In some embodiments, provided is a composite binding molecule of any of the preceding embodiments, wherein the CD38 antigen binding component comprises an immunoglobulin heavy chain variable region comprising an amino acid sequence identical to SEQ ID NO: 3 or 5; and an immunoglobulin light chain variable region comprises an amino acid sequence identical to SEQ ID NO: 4. In some embodiments, provided is a composite binding molecule of any of the preceding embodiments, wherein the CD19 antigen binding component comprises an anti-CD19 immunoglobulin heavy chain variable region comprising an amino acid sequence having at least about 90%, 95%, 97%, 99% identity to SEQ ID NO: 1 or 6; and an immunoglobulin light chain variable region comprising an amino acid sequence having at least about 90%, 95%, 97%, 99% identity to SEQ ID NO: 4.

In some embodiments, provided is a composite binding molecule of any of the preceding embodiments, wherein the anti-CD19 antigen binding component comprises an immunoglobulin heavy chain variable region comprising an amino acid sequence identical to SEQ ID NO: 1 or 6; and an immunoglobulin light chain variable region comprises an amino acid sequence identical to SEQ ID NO: 4. In some embodiments, provided is a composite binding molecule of any of the preceding embodiments, wherein the anti-CD38 immunoglobulin heavy chain variable region further comprises a first immunoglobulin heavy chain constant region. In some embodiments, provided is a composite binding molecule of any of the preceding embodiments, wherein the anti-CD38 immunoglobulin light chain variable region further comprises an immunoglobulin light chain constant region. In some embodiments, provided is a composite binding molecule of any of the preceding embodiments, wherein the anti-CD19 immunoglobulin heavy chain variable region further comprises a second immunoglobulin heavy chain constant region. In some embodiments, provided is a composite binding molecule of any of the preceding embodiments, wherein the first immunoglobulin heavy chain constant region and/or the second immunoglobulin heavy chain constant region comprises one or more amino acid substitutions that disfavors homodimerization of the anti-CD38 immunoglobulin heavy chain constant region and/or promotes heterodimerization of the first heavy chain constant region and the second heavy chain constant region. In some embodiments, provided is a composite binding molecule of any of the preceding embodiments, wherein the one of the first or second immunoglobulin heavy chain constant regions comprises a T366W substitution (EU numbering), and the other of the first or second immunoglobulin heavy chain constant regions comprises a T366S/L368A/Y407V substitution (EU numbering), such that the heterodimerization of the first and second immunoglobulin heavy chain constant regions is favored compared to homodimerization of the first or second immunoglobulin heavy chain constant regions. In some embodiments, provided is a composite binding molecule of any of the preceding embodiments, wherein a single bispecific binding molecule is formed from the CD38 antigen binding component and the CD19 antigen binding component.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A shows cell surface expression of CD19 and CD38. FIGS. 12B and 12C show binding profiles of CD19 and CD38 antibodies. FIGS. 12D and 12E shows binding of CD19 and CD38 controls.

DETAILED DESCRIPTION

Figure 1:
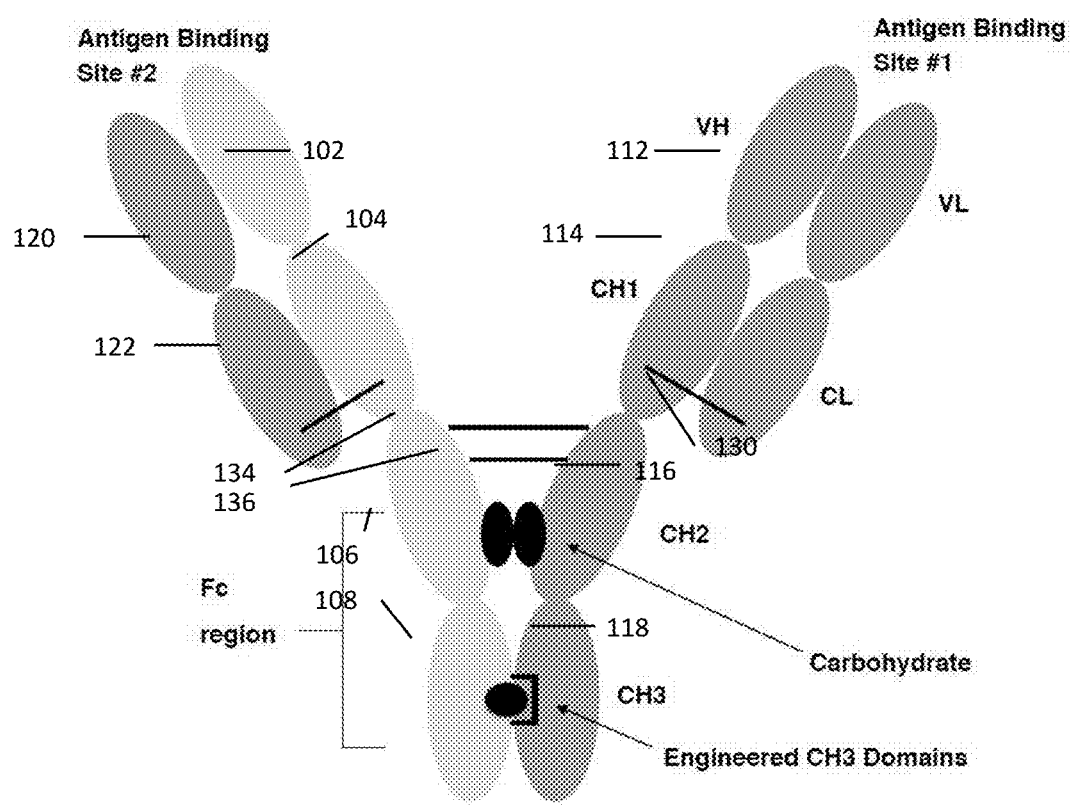
FIG. 1 illustrates the structure of a common light chain bispecific IgG.

Immunosuppressive B-cell populations that suppress the anti-tumor immune response can be generally defined by the presence of more than one cell surface biomarker. Therapeutics that effectively and specifically target immunosuppressive B cells can therefore be used to prevent immunosuppression and/or remove immunosuppression in, adjacent to, or surrounding a tumor or within a tumor environment. Provided herein are composite binding molecules that target immunosuppressive B cells. Furthermore, provided are composite binding molecules comprising a first binding component configured to bind a first target and a second binding component configured to bind a second target, wherein the first target comprises a B-cell lineage surface marker, and wherein the second target comprises a suppressive B-cell surface marker. Disclosed herein are multivalent antibodies that specifically bind to B-cell populations associated with negative modulation or immunosuppression of an anti-tumor response. Immunosuppressive B cells can comprise or be defined by cell surface biomarkers CD19 and CD38. The bispecific antibodies provided herein can target both CD19 and CD38 to inhibit the function of immune suppressive B cells. In certain instances, the function of immunosuppressive B cells comprises the release of IL10, IL 35, TGF-beta, or a combination thereof. Multivalent or bispecific antibodies targeting CD19 and CD38 can also be used for treating tumorigenic conditions and/or cancers associated with immunosuppressive B cells and/or immune dysfunction.

The term "immunosuppression" or "immunodepression" or "negative immune modulation", as used herein, refers to the reduction or suppression of the immune system function, i.e. immunosuppression generally denotes a state when immune system function is reduced or absent. In certain instances, immunosuppression generally denotes a state when immune system function against a tumor or within, surrounding, or adjacent to the tumor microenvironment is reduced or absent. The whole immune response may be depressed, the immune response within a local or specific region may be reduced, or a particular population of immunologically active lymphocytes may be selectively affected. Antigen-specific immunosuppression may be the result of deletion or suppression of a particular population of antigen-specific cells, or the result of enhanced regulation of the immune response by antigen-specific suppressor cells. References to immunosuppressive B cells refer to B cells or B-cell populations that exert negative modulation on the immune response and can be identified by specific surface markers associated with such populations, such as CD38. In certain instances, immunosuppression can be identified by the presence or release of IL-10, IL-35, TGF-beta, or a combination thereof. In certain instances, immunosuppression can be identified by the presence or release by B cells of IL-10, IL-35, TGF-beta, or a combination thereof.

As used herein, the term "cancer" can refer to or describe the physiological condition in mammals that is typically characterized by unregulated cell growth. Cancer can also include, but is not limited to, hematological tumors and/or solid tumors. Cancer can refer to diseases of the blood, bones, organs, skin tissues and vascular system, including but not limited to bladder, blood, bones, brain, breast, cervix, chest, colon, endometrium, esophagus, eyes, head kidneys, kidneys, liver, lungs, lymph nodes, mouth, neck, ovaries, pancreas, prostate, rectum, kidney, skin, stomach, testes, throat and uterus. Specific cancers include, but are not limited to, leukemia (acute lymphocytic leukemia (ALL), acute myelogenous leukemia (AML), chronic lymphocytic leukemia (CLL), chronic bone marrow Chronic myelogenous leukemia (CML), hairy cell leukemia, mature B-cell tumor (small lymphocytic lymphoma, B-cell pro-lymphocytic leukemia, lymphoplasmacytic lymphoma (such as Waldenstrom's giant ball) Proteinemia or indolent lymphoma), spleen marginal zone lymphoma, plasma cell myeloma, plasma cell leukemia, plasmacytoma, pen-implant immunoglobulin deposition, heavy chain disease, extranodal marginal zone B-cell lymphoma MALT lymphoma), nodal marginal zone B cell lymphoma (NMZL), gastrointestinal tumor (e.g., gastrointestinal stromal tumor (GIST)), follicular lymphoma, mantle cell lymphoma/leukemia, Diffuse B-cell lymphoma, mediastinal (thymus) large B-cell lymphoma, intravascular large B-cell lymphoma, primary exudative lymphoma, and Burkitt's lymphoma (Burkitt lymphoma), mature T cells and natural killer cell (NK) tumors (pre-lymphocytic leukemia, T-cell large lymphocytic leukemia, invasive NK cell leukemia, adult T-cell leukemia/lymphoma, Extranodal NK/T-cell lymphoma, enteropathic T-cell lymphoma, hepatosplenic T-cell lymphoma, blastic NK cell lymphoma, mycosis fungoides (Sezary syndrome), primary Skin degenerative large cell lymphoma, lymphomatoid papulosis, angioimmunoblastic T-cell lymphoma, unspecified peripheral T-cell lymphoma and degenerative large cell lymphoma, Hodgkin's lymphoma (nodular sclerosis, mixed cell type, lymphocyte rich type, lymphocyte depleted or unreduced type, nodular lymphocyte type), myeloma (multiple myeloma, inert myeloma, smoldering myeloma)), chronic myeloproliferative diseases, myelodysplasia/myeloproliferative diseases, myelodysplastic syndromes, lymphoproliferative disorders associated with immunodeficiency, histiocytic and dendritic cell tumors, Hypercytosis, chondrosarcoma, Ewing sarcoma, fibrosarcoma, malignant giant cell tumor, myeloma bone disease, osteosarcoma, breast cancer (hormone dependent, non-hormone dependent), gynecological cancer (child Cervical, endometrial, fallopian tube, gestational trophoblastic disease, ovary, peritoneum, uterus, vagina and vulva), basal cell carcinoma (BCC), squamous cell carcinoma (SCC), malignant melanoma, protuberous cutaneous fibrosarcoma, Merkel cell carcinoma, Kaposi's sarcoma, astrocytoma, hair cell astrocytoma, embryonic hair growth neuroepithelial neoplasia, oligodendroglioma, Ependymoma, glioblastoma multiforme, mixed glioma, oligodendrocyte astrocytoma, medulloblastoma, retinoblastoma, neuroblastoma, embryonal tissue tumor, teratoma, Malignant mesothelioma (peritoneal mesothelioma, pericardial mesothelioma, pleural mesothelioma), gastric-intestinal-pancreatic or gastrointestinal pancreatic neuroendocrine tumor (GEP-NET), carcinoid tumor, pancreatic endocrine tumor (PET)), colorectal adenocarcinoma, knot Rectal cancer, invasive neuroendocrine tumor, leiomyosarcoma, mucinous adenocarcinoma, signet ring cell adenocarcinoma, hepatocellular carcinoma, hepatobiliary liver cancer, hepatic blastoma, hemangioma, hepatic adenoma, focal nodular hyperplasia (nodular regenerative hyperplasia, hamartoma), non-small cell lung cancer (NSCLC) (squamous cell lung cancer, adenocarcinoma, large cell lung cancer), small cell lung cancer, thyroid cancer, prostate cancer (hormone refractory, non-androgen dependent Sex, androgen-dependent, hormone-insensitive), renal cell carcinoma and soft tissue sarcoma (fibrosarcoma, malignant fibrous histiocytoma, cutaneous fibrosarcoma, liposarcoma, rhabdomyosarcoma, leiomyosarcoma, angiosarcoma, synovial sarcoma, malignant Peripheral nerve sheath tumor/neurofibrosarcoma, extra-osseous osteosarcoma).

The term "CD19" or "Cluster of Differentiation 19" (also known as B4, T-cell surface antigen Leu-12, and CVID3) refers to a B-cell lineage surface biomarker or transmembrane protein that in humans is encoded by the gene CD19. CD19 can function as coreceptor for the B-cell antigen receptor complex (BCR) on B-lymphocytes, which decreases the threshold for activation of downstream signaling pathways and for triggering B cell responses to antigens. Structurally, a CD19 amino acid sequence has at least about 90%, 91%, 92%, 93%, 94%, 95%, 96%, 97%, 98%, 99% or 100% sequence identity with the amino acid sequence, e.g., of GenBank accession no. NM_001178098.2→NP_001171569.1 or NM_001770.6→NP_001761.3 over a sequence length of at least 50, 100, 150, 200, 250, 300, 350, 400, 450, 500 amino acids or over the full length of the polypeptide. Structurally, a CD19 nucleic acid sequence has at least about 90%, 91%, 92%, 93%, 94%, 95%, 96%, 97%, 98%, 99% or 100% sequence identity with the nucleic acid sequence, e.g., of GenBank accession no. NG_007275.1 or NCBI Gene ID 930, over a sequence length of at least 300, 500, 750, 1000, 1250, 1500 nucleic acids or over the full length of the polynucleotide. The sequence alignments can be performed using any alignment algorithm known in the art, e.g., BLAST, ALIGN, set to default settings.

The term "CD38" or "Cluster of Differentiation 38" (also known as ADPRC1) refers to a B-cell surface biomarker or transmembrane protein that in humans is encoded by the gene CD38. CD38 can function in B-cell signaling that leads to cellular activation and proliferation. Structurally, a CD38 amino acid sequence has at least about 90%, 91%, 92%, 93%, 94%, 95%, 96%, 97%, 98%, 99% or 100% sequence identity with the amino acid sequence, e.g., of GenBank accession no. NM_001775.4→NP_001766.2 over a sequence length of at least 50, 100, 150, 200, 250, amino acids or over the full length of the polypeptide. Structurally, an CD19 nucleic acid sequence has at least about 90%, 91%, 92%, 93%, 94%, 95%, 96%, 97%, 98%, 99% or 100% sequence identity with the nucleic acid sequence, e.g., of GenBank accession no. NC 000004.12 or NCBI Gene ID 952, over a sequence length of at least 300, 500, 750 nucleic acids or over the full length of the polynucleotide. The sequence alignments can be performed using any alignment algorithm known in the art, e.g., BLAST, ALIGN, set to default settings.

The term "antibody" herein is used in the broadest sense and includes multivalent or bispecific antibodies and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

Among the provided antibodies are multispecific or multivalent antibodies (for example, bispecific antibodies and polyreactive antibodies) and antibody fragments thereof. The antibodies include antibody-conjugates and molecules comprising the antibodies, such as chimeric molecules. Thus, an antibody includes, but is not limited to, full-length and native antibodies, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A monoclonal antibody can comprise a human IgG1 constant region or a human IgG4 constant region.

The terms "complementarity determining region," and "CDR," which are synonymous with "hypervariable region" or "HVR," are known in the art and refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme); MacCallum et al., *J. Mol. Biol.* 262:732-745 (1996), "Antibody-antigen interactions: Contact analysis and binding site topography," *J Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB,"

*Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology*, 6th ed., W.H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

Among the provided antibodies are antibody fragments. An "antibody fragment" can refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs. Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody.

Herein a molecule, peptide, polypeptide, antibody, or antibody fragment can be referred to as "bispecific" or "dual-specific" including grammatical equivalents. A bispecific molecule possesses the ability to specifically bind to at least two structurally distinct targets. The specific binding may be the result of two distinct binding moieties that are structurally distinct at the molecular level, including but not limited to distinct non-identical amino acid sequences; or a single binding moiety that is able to specifically bind to two structurally distinct targets with high affinity (e.g., with a KD less than about $1 \times 10^{-6}$). A molecule, peptide, polypeptide, antibody, or antibody fragment referred to as "multi-specific" refers to a molecule that possesses the ability to specifically bind to at least three structurally distinct targets. A "bispecific antibody" including grammatical equivalents refers to a bispecific molecule that preserves at least one fragment of an antibody able to specifically bind a target, for example, a variable region, heavy or light chain, or one or more complementarity determining regions from an antibody molecule. A "multi-specific antibody" including grammatical equivalents refers to a multi-specific molecule that preserves at least one fragment of an antibody able to specifically bind with a target, for example, a variable region, heavy or light chain, or complementarity determining region from an antibody molecule.

A "linker" herein is also referred to as "linker sequence" "spacer" "tethering sequence" or grammatical equivalents thereof. A "linker" as referred herein connects two distinct molecules that by themselves possess target binding, catalytic activity, or are naturally expressed and assembled as separate polypeptides. For example, two distinct binding moieties or a heavy-chain/light-chain pair. A number of strategies may be used to covalently link molecules together. These include but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length or about 1 to 30 amino acids in length. In one embodiment, linkers of 1 to 20 amino acids in length may be used. Useful linkers include glycine-serine polymers, including for example (GS)n, (GSGGS)n (SEQ ID NO: 224), (GGGGS)n (SEQ ID NO: 225), and (GGGS)n (SEQ ID NO: 226), where n is an integer of at least one, glycine-alanine polymers, alanine-serine polymers, and other flexible linkers. Exemplary, linkers for linking antibody fragments or single chain variable fragments can include AAEPKSS (SEQ ID NO: 227), AAEPKSSDKTHTCPPCP (SEQ ID NO: 228), GGGG (SEQ ID NO: 229), or GGGGDKTHTCPPCP (SEQ ID NO: 230). Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

"Fragment-based" bispecific antibodies or bispecific antibodies comprising a "single chain variable fragment" or "scFv" of this disclosure can refer to a single chain antibody, or fragment thereof, that comprises two binding moieties and a linker connecting the two binding moieties. The linker may be a polypeptide linker or other linker of suitable flexibility so as not to inhibit binding of either targeting moiety. Fragment based bispecific antibody formats include tandem $V_{HH}$ antibodies, tandem scFvs, scFv-Fabs, F(ab)$_2$, dual-affinity retargeting antibodies (DARTs). Such fragment-based antibodies can be further manipulated to comprise additional binding moieties with specificity for a given target e.g., $A_2:B_1$, $A_1:B_2$ or $A_2:B_2$, or with fragments of an Fc region to improve pharmacokinetics or promote ADCC, ADCP, or CDC.

A "binding moiety" refers to a portion of a molecule, peptide, polypeptide, antibody, or antibody fragment that mediates specific binding to a recited target or antigen or epitope. By way of example, the binding moiety of an antibody may comprise a heavy-chain/light-chain variable region pair or one or more complementarity determining regions (CDRs).

A "target" as referred to herein refers to the portion of a molecule that participates with a binding moiety of a molecule, peptide, polypeptide, antibody, or antibody fragment. A target can comprise an amino acid sequence and/or a carbohydrate, lipid or other chemical entity. An "antigen" is a target comprising a portion that is able to be bound by an adaptive immune molecule such as an antibody or antibody fragment, B-cell receptor, or T-cell receptor.

The "valency" of a bispecific or multi-specific molecule refers to the number of targets a recited molecule, peptide, polypeptide, antibody, or antibody fragment is able to bind. For instance, a molecule that is monovalent is able to bind to one molecule of a specific target, a bivalent molecule is able to bind to two molecules, and a tetravalent molecule is able to bind four targets. A bispecific, bivalent molecule, for example, is one that can bind to two targets and to two structurally different targets. For example, a bispecific, bivalent molecule when placed into contact with a solution comprising target A and target B may bind $A_2$, $B_2$ or A:B.

A "humanized" antibody is an antibody in which all or substantially all CDR amino acid residues are derived from non-human CDRs and all or substantially all FR amino acid residues are derived from human FRs. A humanized antibody optionally can include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

"ADCC" or "antibody dependent cell-mediated cytotoxicity" as used herein, refers to the cell-mediated reaction wherein nonspecific cytotoxic cells that express FcγRs recognize bound antibody on a target cell and subsequently cause lysis of the target cell. ADCC can be correlated with binding to FcγRIIIa wherein increased binding to FcγRIIIa leads to an increase in ADCC activity. "ADCP" or antibody dependent cell-mediated phagocytosis, as used herein, can refer to the cell-mediated reaction wherein nonspecific cytotoxic cells that express FcγRs recognize bound antibody on a target cell and subsequently cause phagocytosis of the target cell.

The terms "polypeptide" and "protein" are used interchangeably and refers to a polymer of amino acid residues, and are not limited to a minimum length. Polypeptides, including the provided antibodies and antibody chains and other peptides, e.g., linkers and binding peptides, can include amino acid residues including natural and/or non-natural amino acid residues. The terms also include post-expression modifications of the polypeptide, for example, glycosylation, sialylation, acetylation, phosphorylation, and the like. In some aspects, the polypeptides can contain modifications with respect to a native or natural sequence, as long as the protein maintains the desired activity. These modifications can be deliberate, as through site-directed mutagenesis, or can be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Amino acid sequence variants of the antibodies provided herein can be contemplated and conceived. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody amino acid sequence variants of an antibody can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Antibody variants having one or more amino acid substitutions can be provided. Sites of interest for mutagenesis by substitution include the CDRs and FRs. Amino acid substitutions can be introduced into an antibody of interest and the products screened for a desired activity, e.g., retained/improved antigen binding, decreased immunogenicity, or improved ADCC or CDC.

This disclosure also provides for "immunoconjugates" or "antibody conjugates" or "antibody-drug conjugates" that refer to an antibody conjugated to one or more heterologous molecule(s). For example, an immunoconjugate can comprise an antibody conjugated to one or more cytotoxic agents, such as chemotherapeutic agents or drugs, growth inhibitory agents, protein domains, toxins (e.g., protein toxins, enzymatically active toxins of bacterial, fungal, plant, or animal origin, or fragments thereof), or radioactive isotopes. In some embodiments, an immunoconjugate can comprise the composite binding molecule disclosed herein, or fragment thereof (e.g., an scFv).

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. See e.g., Li et al., "Cell culture processes for monoclonal antibody production."*Mabs*. 2010 September-October; 2(5): 466-477. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

As used herein the term "individual," "patient," or "subject" refers to individuals diagnosed with, suspected of being afflicted with, or at-risk of developing at least one disease for which the described compositions and method are useful for treating. In certain embodiments, the individual is a mammal. In certain embodiments, the mammal is a mouse, rat, rabbit, dog, cat, horse, cow, sheep, pig, goat, llama, alpaca, or yak. In certain embodiments, the individual is a human.

As used herein, the term "about" used to modify a specific number refers to that number plus or minus 10% of that number. The term "about" modifying a range refers to that range minus 10% of its lowest value and plus 10% of its greatest value.

As used herein, the terms "treatment" or "treating" are used in reference to a pharmaceutical or other intervention regimen used for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made. Skilled artisans will recognize that given a population of potential individuals for treatment not all will respond or respond equally to the treatment. Such individuals are considered treated.

The section headings used herein are for organizational purposes only and are not to be construed as limiting the subject matter described.

Bispecific Molecules

Provided herein are bispecific or multivalent or composite binding molecules comprising a first binding component configured to bind a first target and a second binding component configured to bind a second target, wherein the first target comprises a B-cell lineage surface marker, and wherein the second target comprises a suppressive B-cell surface marker. Immunosuppressive B cells or B-cell populations can comprise a B-cell linage surface biomarker and a suppressive B-cell surface biomarker. The B-cell lineage surface markers can comprise CD19, CD138, IgA, or CD45. Immunosuppressive B-cell surface markers can comprise IgD, CD1, CD5, CD21, CD24, CD38, HM13, SLAMF7, AQP3, or latent TGF-beta (e.g., TGF-beta LAP). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38. In certain embodiments, the composite binding molecule binds to CD38 and CD19.

A multivalent or bispecific or composite binding molecule possesses the ability to specifically bind to at least two structurally distinct targets. The specific binding may be the result of two distinct binding moieties that are structurally distinct at the molecular level, including but not limited to distinct non-identical amino acid sequences; or a single binding moiety that is able to specifically bind to two structurally distinct targets. A molecule, peptide, polypeptide, antibody, or antibody fragment referred to as "multispecific" or "multivalent" or "bispecific" can refer to a molecule that possesses the ability to specifically bind to at least two structurally distinct targets. In some embodiments, the first or the second binding component of the composite binding molecule comprises a polypeptide. In certain embodiments, the first or the second binding component consists of a polypeptide. In some embodiments, the first and the second binding component of the composite binding molecule comprises a polypeptide. In certain embodiments, the first and the second binding component consist of a polypeptide. In certain embodiments, the polypeptide of the first or second binding component comprises an amino acid sequence at least 100 amino acid residues in length. In certain embodiments, the polypeptide of the first and second binding component comprise an amino acid sequence at least 100 amino acid residues in length.

A bispecific molecule can be a bispecific antibody that preserves at least one fragment of an antibody able to specifically bind with a target, for example, a variable region, heavy or light chain, or one or more complementarity determining regions from an antibody molecule. In some embodiments, the composite binding molecule described herein is a bispecific antibody and/or dual antigen-binding fragment thereof. Bispecific antibodies possess the ability to bind to two structurally distinct targets or antigens. In some embodiments, the bispecific antibody comprises a first binding component configured to bind a first target and a second binding component configured to bind a second target, wherein the first target comprises a B-cell lineage surface marker (e.g. CD19, CD138, IgA, or CD45), and wherein the second target comprises a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

Immunosuppressive B cells or immunosuppressive B-cell populations can comprise cell surface biomarkers CD19 and CD38. Further disclosed herein are bispecific antibodies that target CD19 and CD38. In some embodiments, the CD19 binding component comprises a variable heavy chain (VH) comprising SEQ ID NO: 1. In certain embodiments, the CD19 binding component comprises a VH CDR1 region comprising any one of SEQ ID NO: 11, SEQ ID NO: 12, SEQ ID NO: 13, SEQ ID NO: 14, or SEQ ID NO: 15. In certain embodiments, the CD19 binding component comprises a VH CDR2 region comprising any one of SEQ ID NO: 21, SEQ ID NO: 22, SEQ ID NO: 23, SEQ ID NO: 24, or SEQ ID NO: 25. In certain embodiments, the CD19 binding component comprises a VH CDR3 region comprising any one of SEQ ID NO: 31, SEQ ID NO: 32, SEQ ID NO: 33, SEQ ID NO: 34, or SEQ ID NO: 35.

In some embodiments, the CD19 binding component comprises a variable light chain (VL) comprising SEQ ID NO: 2. In certain embodiments, the CD19 binding component comprises a VL CDR1 region comprising any one of SEQ ID NO: 41, SEQ ID NO: 42, SEQ ID NO: 43, SEQ ID NO: 45, or SEQ ID NO: 45. In certain embodiments, the CD19 binding component comprises a VL CDR2 region comprising any one of SEQ ID NO: 51, SEQ ID NO: 52, SEQ ID NO: 53, SEQ ID NO: 54, or SEQ ID NO: 55. In certain embodiments, the CD19 binding component comprises a VL CDR3 region comprising any one of SEQ ID NO: 61, SEQ ID NO: 62, SEQ ID NO: 63, SEQ ID NO: 64, or SEQ ID NO: 65.

In some embodiments, the bispecific antibody comprises a first binding component, wherein the first binding component comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35, an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65.

In some embodiments, the bispecific antibody comprises a CD19 binding component, wherein the CD19 binding component comprises an HCDR1 amino acid sequence set forth in SEQ ID NO: 11, an HCDR2 amino acid sequence set forth in SEQ ID NO: 21, an HCDR3 amino acid sequence set forth in SEQ ID NO: 31, an LCDR1 amino acid sequence set forth in SEQ ID NO: 41, an LCDR2 amino acid sequence set forth in SEQ ID NO: 51, and/or an LCDR3 amino acid sequence set forth in SEQ ID NO: 61.

In some embodiments, the bispecific antibody comprises a CD19 binding component, wherein CD19 first binding component comprises an HCDR1 amino acid sequence set forth in SEQ ID NO: 12, an HCDR2 amino acid sequence set forth in SEQ ID NO: 22, an HCDR3 amino acid sequence set forth in SEQ ID NO: 32, an LCDR1 amino acid sequence set forth in SEQ ID NO: 42, an LCDR2 amino acid sequence set forth in SEQ ID NO: 52, and/or an LCDR3 amino acid sequence set forth in SEQ ID NO: 62.

In some embodiments, the bispecific antibody comprises a CD19 binding component, wherein the CD19 binding component comprises an HCDR1 amino acid sequence set forth in SEQ ID NO: 15, an HCDR2 amino acid sequence set forth in SEQ ID NO: 25, an HCDR3 amino acid sequence set forth in SEQ ID NO: 35, an LCDR1 amino acid sequence set forth in SEQ ID NO: 45, an LCDR2 amino acid sequence set forth in SEQ ID NO: 55, and/or an LCDR3 amino acid sequence set forth in SEQ ID NO: 65.

In some embodiments, the CD19 binding comprises a variable heavy chain and light chain or CDRs corresponding to or derived from Inebilizumab, Tafasitamab, Taplitumomab, Obexelimab, Blinatumomab, Coltuximab, Denintuzumab, or Loncastuximab, MOR208, MEDI-551, XmAb 5871, MDX-1342, or AFM11.

In some embodiments, the CD38 binding component comprises a variable heavy chain (VH) comprising SEQ ID NO: 3. In certain embodiments, the CD19 binding component comprises a VH CDR1 region comprising any one of SEQ ID NO: 71, SEQ ID NO: 72, SEQ ID NO: 73, SEQ ID NO: 75, or SEQ ID NO: 75. In certain embodiments, the CD19 binding component comprises a VH CDR2 region comprising any one of SEQ ID NO: 81, SEQ ID NO: 82, SEQ ID NO: 83, SEQ ID NO: 84, or SEQ ID NO: 85. In certain embodiments, the CD19 binding component comprises a VH CDR3 region comprising any one of SEQ ID NO: 91, SEQ ID NO: 92, SEQ ID NO: 93, SEQ ID NO: 94, or SEQ ID NO: 95.

In some embodiments, the CD38 binding component comprises a variable light chain (VL) comprising SEQ ID NO: 4. In certain embodiments, the CD19 binding component comprises a VL CDR1 region comprising any one of SEQ ID NO: 101, SEQ ID NO: 102, SEQ ID NO: 103, SEQ ID NO: 105, or SEQ ID NO: 105. In certain embodiments, the CD19 binding component comprises a VL CDR2 region comprising any one of SEQ ID NO: 111, SEQ ID NO: 112, SEQ ID NO: 113, SEQ ID NO: 114, or SEQ ID NO: 115. In certain embodiments, the CD19 binding component comprises a VL CDR3 region comprising any one of SEQ ID NO: 121, SEQ ID NO: 122, SEQ ID NO: 123, SEQ ID NO: 124, or SEQ ID NO: 125.

In some embodiments, the bispecific antibody comprises a CD38 binding component, wherein the CD38 binding component comprises an HCDR1 amino acid sequence set forth in SEQ ID NO: 71, an HCDR2 amino acid sequence set forth in SEQ ID NO: 81, an HCDR3 amino acid sequence set forth in SEQ ID NO: 91, an LCDR1 amino acid sequence set forth in SEQ ID NO: 101, an LCDR2 amino acid sequence set forth in SEQ ID NO: 111, and/or an LCDR3 amino acid sequence set forth in SEQ ID NO: 121.

In some embodiments, the bispecific antibody comprises a CD38 binding component, wherein the CD38 binding component comprises an HCDR1 amino acid sequence set forth in SEQ ID NO: 72, an HCDR2 amino acid sequence set forth in SEQ ID NO: 82, an HCDR3 amino acid sequence set forth in SEQ ID NO: 92, an LCDR1 amino acid sequence set forth in SEQ ID NO: 102, an LCDR2 amino acid sequence set forth in SEQ ID NO: 112, and/or an LCDR3 amino acid sequence set forth in SEQ ID NO: 122.

In some embodiments, the bispecific antibody comprises a CD38 binding component, wherein the CD38 binding component comprises an HCDR1 amino acid sequence set forth in SEQ ID NO: 75, an HCDR2 amino acid sequence set forth in SEQ ID NO: 85, an HCDR3 amino acid sequence set forth in SEQ ID NO: 95, an LCDR1 amino acid sequence set forth in SEQ ID NO: 105, an LCDR2 amino acid sequence set forth in SEQ ID NO: 115, and/or an LCDR3 amino acid sequence set forth in SEQ ID NO: 125.

In some embodiments (e.g., any of the preceding embodiments), the CDR-H2 of the CD38 binding component comprises the amino acid residues P(X1)LG(X2)A (SEQ ID NO: 150), wherein X1 and X2 tolerate amino acid substitutions while maintaining binding to CD38. In certain embodiments, X1 and X2 are selected from amino acids that reduce the hydrophobicity of the CDRH2 amino acid sequence. In certain embodiments, the amino acids that reduce the hydrophobicity include H, Q, T, N, S, G, A, R, K, D, or E. In certain embodiments, the X1 is H and X2 is T.

In some embodiments, the bispecific antibody comprises a CD38 binding component and a CD19 binding component, wherein the CD38 binding component comprises a VH amino acid sequence and a VL amino acid sequence and, wherein the VH amino acid sequence comprises an amino acid sequence at least about 90%, 95%, 97%, 98%, or 99% identical to SEQ ID NO: 3, and the VL comprises an amino acid sequence at least about 90%, 95%, 97%, 98%, or 99% identical to SEQ ID NO: 4; and the CD19 binding component comprises a VH amino acid sequence and a VL amino acid sequence, wherein the VH amino acid sequence comprises an amino acid sequence at least about 90%, 95%, 97%, 98%, or 99% identical to SEQ ID NO: 1, and the VL comprises an amino acid sequence at least about 90%, 95%, 97%, 98%, or 99% identical to SEQ ID NO: 2.

In some embodiments, the bispecific antibody comprises a CD38 binding component and a CD19 binding component, wherein the CD38 binding component comprises a VH amino acid sequence and a VL amino acid sequence and, wherein the VH amino acid sequence comprises an amino acid sequence identical to SEQ ID NO: 3, and the VL comprises an amino acid sequence identical to SEQ ID NO: 4; and the CD19 binding component comprises a VH amino acid sequence and a VL amino acid sequence, wherein the VH amino acid sequence comprises an amino acid sequence identical to SEQ ID NO: 1, and the VL comprises an amino acid sequence identical to SEQ ID NO: 2.

In some embodiments, the bispecific antibody comprises a CD38 binding component and a CD19 binding component, wherein the CD38 binding component comprises a VH amino acid sequence and a VL amino acid sequence and, wherein the VH amino acid sequence comprises an amino acid sequence at least about 90%, 95%, 97%, 98%, or 99% identical to SEQ ID NOs: 3, 215, or 218-223, and the VL comprises an amino acid sequence at least about 90%, 95%, 97%, 98%, or 99% identical to SEQ ID NO:s 4 or 223; and the CD19 binding component comprises a VH amino acid sequence and a VL amino acid sequence, wherein the VH amino acid sequence comprises an amino acid sequence at least about 90%, 95%, 97%, 98%, or 99% identical to SEQ ID NOs: 1, 201, or 216-217, and the VL comprises an amino acid sequence at least about 90%, 95%, 97%, 98%, or 99% identical to SEQ ID NO: 2. In some embodiments, the CD19 binding component comprises a $V_H$ amino acid sequence comprising a substitution at A84 and A108. In some embodiments, the substitution comprises A84S and A108L.

In some embodiments, the bispecific antibody comprises a CD38 binding component and a CD19 binding component, wherein the CD38 binding component comprises a VH amino acid sequence and a VL amino acid sequence and, wherein the VH amino acid sequence comprises an amino acid sequence identical to SEQ ID NO: 3, 215, or 218-223, and the VL comprises an amino acid sequence identical to SEQ ID NO: 4 or 223; and the CD19 binding component comprises a VH amino acid sequence and a VL amino acid sequence, wherein the VH amino acid sequence comprises an amino acid sequence identical to SEQ ID NO: 1, 201, 216-217 and the VL comprises an amino acid sequence identical to SEQ ID NO: 2. In some embodiments, the CD19 binding component comprises a VH amino acid sequence comprising a substitution at A84 and A108. In some embodiments, the substitution comprises A84S and A108L.

In some embodiments, the bispecific antibody comprises a CD38 binding component and a CD19 binding component, wherein the CD38 binding component comprises an HCDR1 amino acid sequence set forth in SEQ ID NO: 71, an HCDR2 amino acid sequence set forth in SEQ ID NO: 81, an HCDR3 amino acid sequence set forth in SEQ ID NO: 91, an LCDR1 amino acid sequence set forth in SEQ ID NO: 101, an LCDR2 amino acid sequence set forth in SEQ ID NO: 111, and/or an LCDR3 amino acid sequence set forth in SEQ ID NO: 121; and the CD19 binding component comprises an HCDR1 amino acid sequence set forth in SEQ ID NO: 11, an HCDR2 amino acid sequence set forth in SEQ ID NO: 21, an HCDR3 amino acid sequence set forth in SEQ ID NO: 31, an LCDR1 amino acid sequence set forth in SEQ ID NO: 41, an LCDR2 amino acid sequence set forth in SEQ ID NO: 51, and/or an LCDR3 amino acid sequence set forth in SEQ ID NO: 61.

In some embodiments, the bispecific antibody comprises a CD38 binding component and a CD19 binding component, wherein the CD38 binding component comprises an HCDR1 amino acid sequence set forth in SEQ ID NO: 72, an HCDR2 amino acid sequence set forth in SEQ ID NO: 82, an HCDR3 amino acid sequence set forth in SEQ ID NO: 92, an LCDR1 amino acid sequence set forth in SEQ ID NO: 102, an LCDR2 amino acid sequence set forth in SEQ ID NO: 112, and/or an LCDR3 amino acid sequence set forth in SEQ ID NO: 122; and the CD19 binding component comprises an HCDR1 amino acid sequence set forth in SEQ ID NO: 12, an HCDR2 amino acid sequence set forth in SEQ ID NO: 22, an HCDR3 amino acid sequence set forth in SEQ ID NO: 32, an LCDR1 amino acid sequence set forth in SEQ ID NO: 42, an LCDR2 amino acid sequence set forth in SEQ ID NO: 52, and/or an LCDR3 amino acid sequence set forth in SEQ ID NO: 62.

In some embodiments, when the bispecific comprises a Fab or other structure requiring a light chain constant region for the bispecific format, the VL comprises an amino acid sequence at least about 90%, 95%, 97%, 98%, 99% or is identical to any one of SEQ ID NOs: 210 and/or 211. In some embodiments, when the bispecific comprises a Fab or other structure requiring a light chain constant region for the bispecific format, the VL comprises an amino acid sequence identical to any one of SEQ ID NOs: 210 and/or 211.

In some embodiments, the bispecific antibody comprises a CD38 binding component and a CD19 binding component, wherein the CD38 binding component comprises an HCDR1 amino acid sequence set forth in SEQ ID NO: 75, an HCDR2 amino acid sequence set forth in SEQ ID NO: 85, an HCDR3 amino acid sequence set forth in SEQ ID NO: 95, an LCDR1 amino acid sequence set forth in SEQ ID NO: 105, an LCDR2 amino acid sequence set forth in SEQ ID NO: 115, and/or an LCDR3 amino acid sequence set forth in SEQ ID NO: 125; and the CD19 binding component comprises an HCDR1 amino acid sequence set forth in SEQ ID NO: 15, an HCDR2 amino acid sequence set forth in SEQ ID NO: 25, an HCDR3 amino acid sequence set forth in SEQ ID NO: 35, an LCDR1 amino acid sequence set forth in SEQ ID NO: 45, an LCDR2 amino acid sequence set forth in SEQ ID NO: 55, and/or an LCDR3 amino acid sequence set forth in SEQ ID NO: 65.

In some embodiments, the CD38 binding comprises a variable heavy chain and light chain or CDRs corresponding to or derived from Daratumumab or Isatuximab.

Substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots". In some embodiments, of the variant $V_H$ and $V_L$ sequences, each CDR is unaltered. Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

Alterations (e.g., substitutions) may be made in CDRs, e.g., to improve antibody affinity. Such alterations may be made in CDR encoding codons with a high mutation rate during somatic maturation (See e.g., Chowdhury, *Methods Mol. Biol.* 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See e.g., Hoogenboom et al. in *Methods in Molecular Biology* 178:1-37 (2001)). CDR residues involved in antigen binding may be specifically identified, e.g., using alanine scanning mutagenesis or modeling (See e.g., Cunningham and Wells *Science*, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Antibodies can be altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the CH2 domain of the Fc region (See e.g., Wright et al. *TIBTECH* 15:26-32 (1997)). The oligosaccharide can be various carbohydrates, e.g., mannose, N-acetyl glucosamine (GlcNAc), galactose, sialic acid, fucose attached to a GlcNAc in the stem of the biantennar oligosaccharide structure. Modifications of the oligosaccharide in an antibody can be made, for example, to create antibody variants with certain improved properties. Antibody glycosylation variants can have improved ADCC and/or CDC function. In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (See e.g., WO 08/077546). Asn297 refers to the asparagine residue located at about position 297 in the Fc region (EU numbering of Fc region residues; See e.g., Edelman et al. *Proc Natl Acad Sci USA*. 1969 May; 63(1):78-85). However, Asn297 may also be located about ±3 amino acids upstream or downstream of position 297, i.e., between positions 294 and 300, due to minor sequence variations in antibodies. Such fucosylation variants can have improved ADCC function (See e.g., Okazaki et al. *J. Mol. Biol.* 336:1239-1249 (2004); and Yamane-Ohnuki et al. *Biotech. Bioeng.* 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (See e.g., Ripka et al. *Arch. Biochem. Biophys.* 249:533-545 (1986); Yamane-Ohnuki et al. *Biotech. Bioeng.* 87: 614 (2004); Kanda, Y. et al., *Biotechnol. Bioeng.*, 94(4):680-688 (2006)). Other antibody glycosylation variants are also included (See e.g., U.S. Pat. No. 6,602,684).

In some embodiments, the composite binding molecule provided herein has a dissociation constant ($K_D$) of about 10 µM, 1 µM, 100 nM, 50 nM, 40 nM, 30 nM, 20 nM, 10 nM, 5 nM, 2 nM, 1 nM, 0.5 nM, 0.1 nM, 0.05 nM, 0.01 nM, or 0.001 nM or less (e.g., $10^{-8}$ M or less, e.g., from $10^{-8}$ M to $10^{-13}$M, e.g., from $10^{-9}$M to $10^{-13}$M) for the antibody target. The antibody target can be a CD19 target, a CD38 target, or a target comprising both CD19 and CD38. $K_D$ can be measured by any suitable assay. In certain embodiments, KD can be measured using surface plasmon resonance assays (e.g., using a BIACORE®-2000 or a BIACORE®-3000 or Octet®).

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some instances, the Fc region of an immunoglobulin is important for many important antibody functions (e.g. effector functions), such as antigen-dependent cellular cytotoxicity (ADCC), complement dependent cytotoxicity (CDC), and antibody-dependent cell-mediated phagocytosis (ADCP), result in killing of target cells, albeit by different mechanisms. Accordingly, in some embodiments, the antibodies described herein comprise the variable domains of the invention combined with constant domains comprising different Fc regions, selected based on the biological activities of the antibody for the intended use. In certain instances, Human IgGs, for example, can be classified into four subclasses, IgG1, IgG2, IgG3, and IgG4, and each of these comprises an Fc region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to FcγRIIA$_{H131}$, and with lower affinity to FcγRIIA$_{R131}$ FcγRIIIA$_{V158}$; IgG4 binds to FcγRI, FcγRIIA, FcγRIIB, FcγRIIC, and FcγRIIIA$_{V158}$; and the inhibitory receptor FcγRIIB has a lower affinity for IgG1, IgG2 and IgG3 than all other Fcγ receptors. Studies have shown that FcγRI does not bind to IgG2, and FcγRIIIB does not bind to IgG2 or IgG4. Id. In general, with regard to ADCC activity, human IgG1≥IgG3>>IgG4≥IgG2.

In certain embodiments, anti-CD19 or anti-CD38 variable regions described herein are linked to an Fc that binds to one or more activating Fc receptors (FcγRI/CD64, FcγRIIa/CD32 or FcγRIIIa/CD16), and thereby stimulate ADCC and, in some instances, cause target depletion. In certain embodiments, anti-CD19 or anti-CD38 variable regions described herein are linked to a human IgG1 or IgG3 Fc, i.e., the antibodies are of the IgG1 or IgG3 isotype. In some instances, modifications in the Fc region generate an Fc variant with (a) increased antibody-dependent cell-mediated cytotoxicity ADCC), (b) increased complement mediated cytotoxicity (CDC), (c) increased affinity for C1q and/or (d) increased affinity for a Fc receptor relative to the parent Fc. In some embodiments, the Fc region variants comprise at least one amino acid modification in the Fc region. Combining amino acid modifications are also useful. For example, the variant Fc region may include two, three, four, five, etc. substitutions therein, e.g. of the specific Fc region positions identified herein.

In some embodiments, ADCC activity may be increased by modifying the Fc region. With regard to ADCC activity, in some instances, human IgG1 and IgG3 shows increased ADCC activation when compared to IgG4 and gG2, so an IgG1 or IgG3 constant domain, rather than an IgG2 or IgG4, is chosen for use in an antibody where ADCC is desired. In some embodiments, IgG3 is selected for activation of FcγRIIIA-expressing NK cells, monocytes of macrophages. In certain instances, different IgG isotypes also exhibit differential CDC activity, wherein IgG3 and IgG1 show greater CDC activation than compared to IgG2 or IgG4. Alternatively, in some embodiments, the Fc region is modified to increase antibody dependent cellular cytotoxicity (ADCC), antibody-dependent cell-mediated phagocytosis (ADCP), complement mediated cytotoxicity (CDC), affinity for C1q, and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439 (Kabat numbering). Non-limiting examples of in vitro assays to assess ADCC activity of a molecule of interest is described in U.S. Pat. Nos. 5,500,362 and 5,821, 337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826).

Other examples of Fc region variants are also contemplated (See e.g., Duncan & Winter, *Nature* 322:738-40 (1988); U.S. Pat. Nos. 5,648,260 and 5,624,821; and WO94/29351).

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region.

In some embodiments, an antibody provided herein may be further modified to contain additional non-proteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

Composite binding molecules or bispecific antibodies can differ based on the binding moieties associated with these molecules, wherein there are also several different formats that can be deployed and are envisioned herein. Composite binding molecules or bispecific antibodies can comprise on antibody fragments, substantially intact antibodies, or a combination thereof. In some embodiments, the first or second binding component comprises an immunoglobulin heavy and light chain pair, an scFv, a F(ab), a F(ab')2, a single domain antibody, a variable region fragment from an immunoglobulin new antigen receptor (VNAR), or a variable region derived from a heavy chain antibody (VHH). In certain embodiments, the first and second binding component comprise an immunoglobulin heavy and light chain pair, an scFv, a F(ab), a F(ab')2, a single domain antibody, a variable region fragment from an immunoglobulin new antigen receptor (VNAR), or a variable region derived from a heavy chain antibody (VHH). In some embodiments, the first or second binding component comprises an immunoglobulin heavy and light chain pair. In certain embodiments, the first and second binding component comprise an immunoglobulin heavy and light chain pair. In some embodiments, the first or second binding component comprises an scFv. In certain embodiments, the first and second binding component comprise an scFv.

Bispecific antibodies according to this disclosure comprise intact antibody molecules or substantially fully intact antibody molecules, and may be asymmetric or symmetric.

Asymmetric bispecific antibodies generally comprise a heavy chain/light chain (HC/LC) pair from an antibody specific for target A and an HC/LC pair from an antibody specific for target B, creating a hetero-bifunctional antibody. Hetero-bifunctional antibodies such as these face the problem of unproductive formation of the molecule when it is being produced. HC/LC-A:HC/LC-B is desired, but is usually thermodynamically or statistically unfavorable from all the possible combinations possible. Multiple schemes have been introduced to circumvent this problem. In some instances, the HC/LC pair from an antibody with specificity for A and the HC/LC pair from an antibody with specificity for B further comprise mutations to the FC region to increase the probability of formation of an antibody with HC/LC-A:HC/LC-B. This can be achieved by engineering structural features such as "knobs" into the FC region for HC-A, and "holes" into HC-B, or vice versa, that promote formation of heterodimers between HC-A and HC-B. Another scheme to promote HC-A:HC-B heterodimers is to engineer amino acid residues in the FC portion of HC-A and HC-B to comprise charge pairs that favor electrostatic interactions between HC-B and HC-A. Another scheme to address the problem of chain association is to replace the variable regions of one of the HC/LC pairs with a single-chain binding molecules (e.g., Vim or an scFv). Such that one-half of the molecule comprises a classical HC/LC pair and the other comprises a HC constant region fused or otherwise connected to the single-chain binding molecule. Further modifications can be made to promote proper HC/LC paring and include engineering mutations to the HC and LC for either A or B to favor formation of the proper HC/LC pair; CrossMab technology, which entails swapping the corresponding constant regions of the HC/LC pair. Symmetric bispecific antibodies circumvent the chain association problem by not relying on formation of a hetero-bifunctional molecule. Such examples include: the dual-variable domain molecule, which comprises stacked variable regions of differing specificity; the IgG-scFv molecule, which comprises an scFv of a differing specificity fused to the c-terminus of heavy chain of a classical antibody molecule; the (scFV)$_4$-FC, which comprises two scFvs connected by an Fc region of an Ig (the Fcs dimerize creating a bispecific, tetravalent molecule); the DART-Fc and the two-in-one, amongst others.

The structure of composite binding molecules or bispecific antibodies can be conceived and designed to alter functionality or binding properties of the composite binding molecules or bispecific antibodies (see e.g., "Bispecific antibodies: a mechanistic review of the pipeline." Nat Rev Drug Discovery. 2019 August; 18(8):585-608) (see e.g., "The making of bispecific antibodies" MAbs. 2017 February-March; 9(2): 182-212). For example, the bispecific antibody can be selected from one of the following formats: a common light chain bispecific IgG, a Fab-Fc:scFv-Fc bispecific IgG, a Fab-Fc-Fab:Fc bispecific IgG, a Fab-Fc-scFv:Fab-Fc-scFv bispecific IgG, a Fab-Fc-scFv:Fc bispecific IgG, a Fab-Fc-Fab:Fab-Fc bispecific IgG, an scFv-Fab-Fc:scFv-Fab-Fc bispecific IgG, a Fab-Fab-Fc:Fab-Fab-Fc bispecific IgG, a Fab-Fc-Fab:Fab-Fc-Fab bispecific IgG, and a Fab-Fc-scFv:Fab-Fc bispecific IgG.

Common Light Chain Bispecific IgG

A bispecific antibody having a common light chain bispecific IgG structure can be used herein. FIG. 1 illustrates a bispecific antibody having a common light chain bispecific IgG structure. The structure comprises a first and a second IgG heavy chain. Each heavy chain comprises a VH, CH1, CH2, and CH3 domain. The first heavy chain comprises VH 102, CH1 104, CH2 106, and CH3 108. The second heavy chain comprises VH 112, CH1 114, CH2 116, and CH3 118. The common light chain bispecific IgG structure also comprises a light chain comprising a VL domain 120 and a CL domain 122. Generally, the first heavy chain will comprise a sequence derived from the heavy chain of an antibody with a first specificity; and the second heavy chain will comprise a heavy chain from an antibody with a second specificity. The light chain that pairs with the first and the second heavy chain will be identical, and can be derived from the light chain of an antibody with either specificity, or a separate specificity. A heavy chain can be covalently coupled to a light chain molecule via a covalent bond (e.g. disulfide bond 130). A heavy chain can be coupled to another heavy chain via one or more covalent bonds (e.g. disulfide bond 134 and/or 136). The common light chain bispecific IgG structure can comprise a first and a second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance, "knobs" into "holes") or biochemically (e.g. electrostatic interactions) prevent coupling of the two first heavy chain molecules or two second heavy chain molecules. Exemplary knob into hole mutations can comprise T366W (EU numbering) in one heavy chain and T366S/L368A/Y407V (EU numbering) in a second heavy chain. Exemplary mutations that facilitate coupling of a first and a second heavy chain molecule are disclosed, for example in WO2009089004, U.S. Pat. No. 8,642,745, US PG-PUB: US20140322756 and "The making of bispecific antibodies" MAbs. 2017 February-March; 9(2): 182-212. The common light chain bispecific IgG structure can also comprise carbohydrate molecules 140 coupled thereto or additional modifications thereof.

A bispecific antibody having a common light chain bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the first heavy chain is configured to bind B-cell lineage surface marker and the second heavy is configured to bind a suppressive B-cell surface marker. In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

In some embodiments, the first heavy chain comprises a VH sequence comprising a CD19 binding component and the second heavy chain comprises a VH sequence comprising CD38 binding component. In certain embodiments, the heavy chain CD19 binding component comprises SEQ ID NO: 201, 1, or a variant comprising a mutation at one or both of A84 and A108 of SEQ ID NO: 201 and the heavy chain CD38 binding component comprises SEQ ID NOs: 202, 215, 218-221. In certain embodiments, the variant comprises the mutation A84S and A108L. In some embodiments, the bispecific antibody comprises a common light chain. In certain embodiments, the common light chain sequence comprises a CD19 binding component (e.g. SEQ ID NO: 2). In certain embodiments, the common light chain sequence comprises CD38 binding component (e.g. SEQ ID NO: 4 or SEQ ID NO: 222).

Described herein BS1 comprises a common light chain format with a CD19 binding component configured to bind CD19 and a CD38 binding component configured to bind CD38, wherein the CD19 binding component comprises an antibody or antigen binding fragment thereof and the CD38 binding component comprises an antibody or antigen binding fragment thereof, wherein the CD38 antibody or antigen binding fragment comprises an anti-CD38 immunoglobulin heavy chain variable region paired with an anti-CD38 immunoglobulin light chain variable region and the CD19 antibody or antigen binding fragment comprises an anti-CD19 immunoglobulin heavy chain variable region paired with an anti-CD38 immunoglobulin light chain variable region, wherein the CD38 antibody or antigen binding component comprises: a) a heavy chain complementarity determining region 1 (HCDR1) comprising an amino acid sequence set forth in any one of SEQ ID NOs: 71-75, b) a heavy chain complementarity determining region 2 (HCDR2) comprising an amino acid sequence set forth in any one of SEQ ID NOs: 81-85, or 150-155; c) a heavy chain complementarity determining region 3 (HCDR3) comprising an amino acid sequence set forth in any one of SEQ ID NOs: 91-95; d) a light chain complementarity determining region 1 (LCDR1) comprising an amino acid sequence set forth in any one of SEQ ID NOs: 101-105; e) a light chain complementarity determining region 2 (LCDR2) comprising an amino acid sequence set forth in any one of SEQ ID NOs: 111-115; and/or) a light chain complementarity determining region 3 (LCDR3) comprising an amino acid sequence set forth in any one of SEQ ID NOs: 121-125; and wherein the CD19 antigen binding component comprises: g) a heavy chain complementarity determining region 1 (HCDR1) comprising an amino acid sequence set forth in any one of SEQ ID NOs: 11-15, h) a heavy chain complementarity determining region 2 (HCDR2) comprising an amino acid sequence set forth in any one of SEQ ID NOs: 21-25, i) a heavy chain complementarity determining region 3 (HCDR3) comprising an amino acid sequence set forth in any one of SEQ ID NOs: 31-35; j) a light chain complementarity determining region 1 (LCDR1) comprising an amino acid sequence set forth in any one of SEQ ID NOs: 101-105; k) a light chain complementarity determining region 2 (LCDR2) comprising an amino acid sequence set forth in any one of SEQ ID NOs: 111-115; and/or 1) a light chain complementarity determining region 3 (LCDR3) comprising an amino acid sequence set forth in any one of SEQ ID NOs: 121-125. In some embodiments, the CD 38 antigen binding component comprises a HCDR2 amino acid sequence comprising the sequence P-X1-L-G-X2-A (SEQ ID NO: 156), wherein X1 and X2 are each selected from the group consisting of H, Q, T, N, S, G, A, R, K, D, or E. In certain embodiments, the X1 is H and X2 is T. In some embodiments, the CD19 heavy chain sequence comprises a A84S and/or A108L substitution. In some embodiments, the CD38 light chain comprises a W32H substitution.

Fab-Fc:scFv-Fc Bispecific IgG

Figure 2:
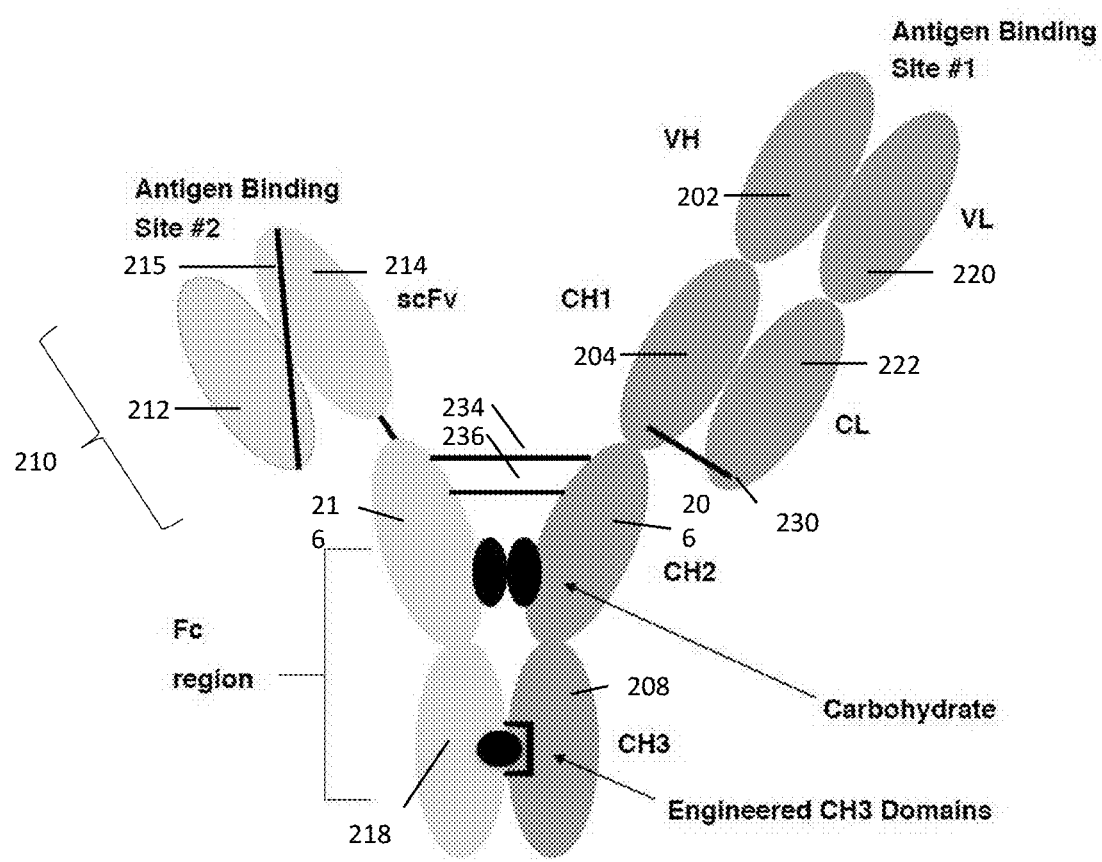
FIG. 2 illustrates the structure of a Fab-Fc:scFv-Fc bispecific IgG.

A bispecific antibody having a Fab-Fc:scFv-Fc Bispecific IgG structure can be used herein. FIG. 2 illustrates a bispecific antibody having a Fab-Fc:scFv-Fc Bispecific IgG structure. The structure comprises a first heavy chain molecule and a modified second IgG heavy chain molecule comprising a single chain variable fragment. The first heavy chain comprises VH 202, CH1 204, CH2 206, and CH3 208, N-terminus to C-terminus respectively. The modified second heavy chain comprises a single chain variable fragment (scFv) 210, CH2 216, and CH3 218, N-terminus to C-terminus respectively. The single chain variable fragment (scFv) can comprises a first domain 212 corresponding to a variable light chain domain, or fragment thereof, a second domain 214 corresponding to a variable heavy chain, or a fragment thereof, and a linker polypeptide 215. The Fab- Fc:scFv-Fc Bispecific IgG structure also comprises a light chain comprising a VL domain 220 and a CL domain 222. The first heavy chain can be covalently coupled to a light chain molecule via a covalent bond (e.g. disulfide bond 230). A first heavy chain can be coupled to the modified second heavy chain via one or more covalent bonds (e.g. disulfide bond 234 and/or 236). The Fab-Fc:scFv-Fc Bispecific IgG structure can comprise a first and a modified second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance) or biochemically (e.g. electrostatic interactions) prevent coupling of the two first heavy chain molecules or two second heavy chain molecules. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The Fab-Fc:scFv-Fc Bispecific IgG structure can also comprise carbohydrate molecules 240 coupled thereto or additional modifications thereof.

A bispecific antibody having a Fab-Fc:scFv-Fc Bispecific IgG structure can target a B-cell lineage surface marker (e.g. CD19, CD138, IgA, or CD45e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc:scFv-Fc Bispecific IgG structure can be engineered so that a first antigen binding site targets CD19 and a second antigen binding site targets CD38. In some embodiments, the first heavy chain comprises a VH sequence comprising CD19 binding component and the second heavy chain comprises a single chain variable fragment (scFv) sequence comprising a CD38 binding component. In certain embodiments, the heavy chain comprising the CD38 single chain variable fragment comprises SEQ ID NO: 205 or SEQ ID NO: 206. In certain embodiments, the VL sequence comprises a CD19 binding component. In certain embodiments, the single chain variable fragment (scFv) sequence comprising a CD38 binding component comprises a CD38 binding component corresponding to an antibody heavy chain and light variable sequence, or CD38 binding fragment thereof. In some embodiments, the first heavy chain comprises a VH sequence comprising CD38 binding component and the second heavy chain comprises a single chain variable fragment (scFv) sequence comprising a CD19 binding component. In certain embodiments, the heavy chain comprising the CD19 single chain variable fragment comprises SEQ ID NO: 203 or SEQ ID NO: 204 or SEQ ID NO: 217. In certain embodiments, the single chain variable fragment (scFv) sequence comprising a CD19 binding component comprises a CD19 binding component corresponding to an antibody heavy chain and light variable sequence, or CD19 binding fragment thereof.

The Fab-Fc:scFv-Fc Bispecific IgG structure can be engineered so that a first antigen binding site targets CD38 and a second antigen binding site targets CD19. In some embodiments, the first heavy chain comprises a VH sequence comprising CD38 binding component and the second heavy chain comprises a single chain variable fragment (scFv) sequence comprising a CD19 binding component. In certain embodiments, the VL sequence comprises a CD38 binding component. In certain embodiments, the single chain variable fragment (scFv) sequence comprising a CD19 binding component comprises a CD19 binding component corresponding to an antibody heavy chain and light variable sequence, or CD19 binding fragment thereof.

Described herein BS2 comprises a CD19 binding component configured to bind CD19 and a CD38 binding component configured to bind CD38, wherein the CD19 binding component comprises an antibody or antigen binding fragment thereof and the CD38 binding component comprises an antibody or antigen binding fragment thereof, wherein the CD38 antigen binding component comprises a Fab that binds CD38 comprising an anti-CD38 immunoglobulin heavy chain variable region paired with an anti-CD38 immunoglobulin light chain variable region and the CD19 antigen binding component comprises an scFv that binds CD19 comprising an anti-CD19 immunoglobulin heavy chain variable region paired with an anti-CD38 immunoglobulin light chain variable region, wherein the CD 38 binding component comprises an immunoglobulin heavy chain comprising an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125; and wherein the CD 19 binding component comprises an immunoglobulin heavy chain comprising an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In some embodiments, the CD 38 antigen binding component comprises a HCDR2 amino acid sequence comprising the sequence P-X1-L-G-X2-A (SEQ ID NO: 156), wherein X1 and X2 are selected from the group consisting of H, Q, T, N, S, G, A, R, K, D, or E. In certain embodiments, the X1 is H and X2 is T. In some embodiments, the CD19 heavy chain sequence comprises a A84S and/or A108L substitution. In some embodiments, the CD38 light chain comprises a W32H substitution.

Fab-Fc-Fab:Fc Bispecific IgG

Figure 3:
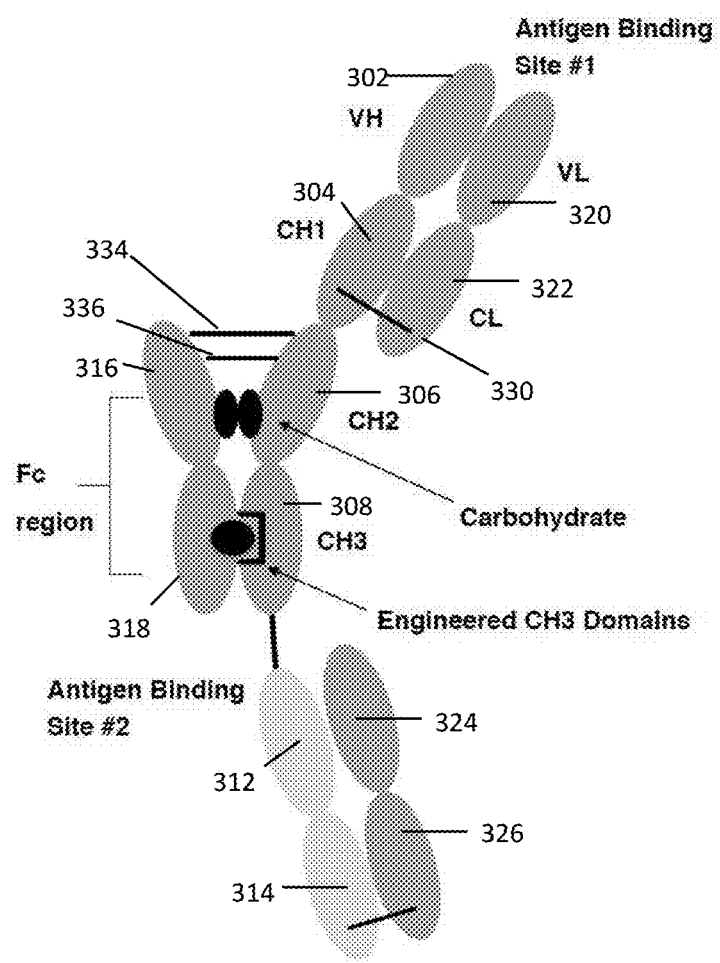
FIG. 3 illustrates the structure of a Fab-Fc-Fab:Fc bispecific IgG.

An engineered bispecific antibody having a Fab-Fc-Fab:Fc Bispecific IgG structure can be used herein. FIG. 3 illustrates a bispecific antibody having a Fab-Fc-Fab:Fc Bispecific IgG structure. The structure comprises a first heavy chain molecule and a modified IgG heavy chain molecule. The first heavy chain comprises VH domain 302, CH1 domain 304, CH2 domain 306, CH3 domain 308, a linker 310, a second VH domain 312, and a second CH1 domain 314, N-terminus to C-terminus respectively. The modified heavy chain comprises a CH2 domain 316, and CH3 domain 318, N-terminus to C-terminus respectively. The Fab-Fc-Fab:Fc Bispecific IgG structure also comprises a first light chain comprising a VL domain 320 and a CL domain 322. The Fab-Fc-Fab:Fc Bispecific IgG structure also comprises a second light chain comprising a VL domain 324 and a CL domain 326. A heavy chain can be covalently coupled to a light chain molecule via a covalent bond (e.g. disulfide bond 330). The first heavy chain can also be covalently coupled to the first second chain molecule via a covalent bond (e.g. disulfide bond 332). A heavy chain and a light chain can be coupled in a manner that the VH domain and CH1 domain of the first heavy chain pair with the VL domain and CL domain of the first light chain. The first heavy chain and second light chain can be coupled in a manner that the second VH domain and second CH1 domain of the first heavy chain pair with the VL domain and CL domain of the second light chain. The first heavy chain can be coupled to the modified second heavy chain via one or more covalent bonds (e.g. disulfide bond 334 and/or 336). The Fab-Fc-Fab:Fc Bispecific IgG structure can comprise a first and a modified second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance) or biochemically (e.g. electrostatic interactions) prevent coupling of the two first heavy chain molecules or two second heavy chain molecules. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The Fab-Fc-Fab:Fc Bispecific IgG structure can also comprise carbohydrate molecules 340 coupled thereto or additional modifications thereof.

A bispecific antibody having a Fab-Fc-Fab:Fc Bispecific IgG structure can target a B-cell lineage surface marker (e.g. CD19, CD138, IgA, or CD45e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-Fab:Fc Bispecific IgG structure can be engineered so that a first antigen binding site targets CD19 and a second antigen binding site targets CD38. In some embodiments, the first heavy chain VH domain (e.g. 302) and VL domain (e.g. 320) comprises a CD19 binding component, wherein the second VH domain (e.g. 312) and VL domain (e.g. 324) comprises a CD38 binding component. In some embodiments, the Fab-Fc-Fab heavy chain comprises SEQ ID NO: 207 and the Fc heavy chain comprises SEQ ID NO: 208.

The Fab-Fc-Fab:Fc Bispecific IgG structure can also be engineered so that a first antigen binding site targets CD38 and a second antigen binding site targets CD19. In some embodiments, the first heavy chain VH domain (e.g. 302) and VL domain (e.g. 320) comprises a CD38 binding component, wherein the second VH domain (e.g. 312) and VL domain (e.g. 324) comprises a CD19 binding component.

Fab-Fc-scFv:Fab-Fc-scFv Bispecific IgG

Figure 4:
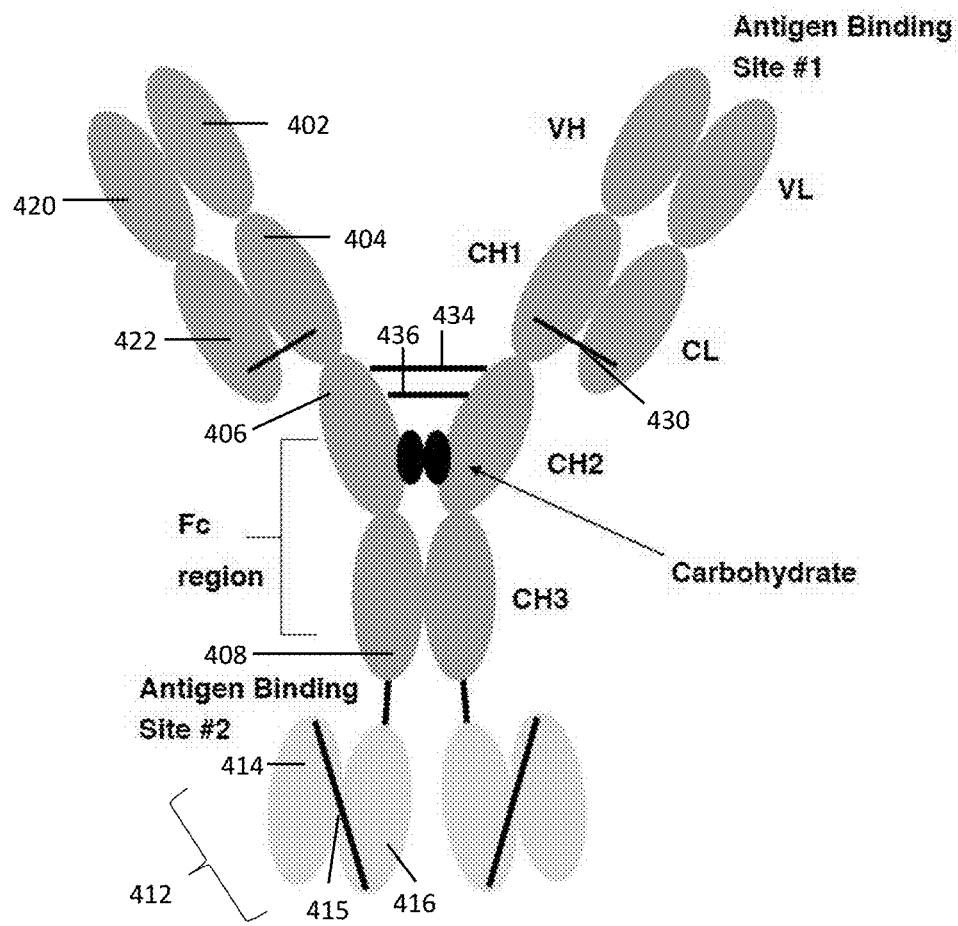
FIG. 4 illustrates the structure of a Fab-Fc-scFv:Fab-Fc-scFv bispecific IgG.

An engineered bispecific antibody having a Fab-Fc-scFv:Fab-Fc-scFv Bispecific IgG structure can be used herein. FIG. 4 illustrates a bispecific antibody having a Fab-Fc-scFv:Fab-Fc-scFv Bispecific IgG structure. The structure comprises a two first heavy chain molecules. The first heavy chain comprises VH domain 402, CH1 domain 404, CH2 domain 406, CH3 domain 408, a linker 410, and a single chain variable fragment (scFv) 412, N-terminus to C-terminus respectively. The single chain variable fragment (scFv) can comprises a first domain 414 corresponding to a variable light chain domain, or fragment thereof, a second domain 416 corresponding to a variable heavy chain, or a fragment thereof, and a second linker polypeptide 415. The Fab-Fc-scFv:Fab-Fc-scFv Bispecific IgG structure also comprises a first light chain comprising a VL domain 420 and a CL domain 422. A heavy chain can be covalently coupled to a light chain molecule via a covalent bond (e.g. disulfide bond 430). A heavy chain can be coupled to another heavy chain via one or more covalent bonds (e.g. disulfide bond 434 and/or 436). The Fab-Fc-scFv:Fab-Fc-scFv Bispecific IgG structure can also comprise carbohydrate molecules 440 coupled thereto or additional modifications thereof.

A bispecific antibody having a Fab-Fc-scFv:Fab-Fc-scFv Bispecific IgG structure can target a B-cell lineage surface marker (e.g. CD19, CD138, IgA, or CD45e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-scFv:Fab-Fc-scFv Bispecific IgG structure can be engineered so that a first antigen binding site targets CD19 and a second antigen binding site targets CD38. In some embodiments, the first heavy chain VH domain (e.g. 402) and VL domain (e.g. 420) comprises a CD19 binding component, wherein the single chain variable fragment (scFv) (e.g. 412) sequence comprises a CD38 binding component. In certain embodiments, the single chain variable fragment (scFv) sequence comprising a CD38 binding component comprises a CD38 binding component corresponding to an antibody heavy chain and light variable sequence, or CD38 binding fragments thereof The Fab-Fc-scFv:Fab-Fc-scFv Bispecific IgG structure can also be engineered so that a first antigen binding site targets CD38 and a second antigen binding site targets CD19. In some embodiments, the first heavy chain VH domain (e.g. 402) and VL domain (e.g. 420) comprises a CD38 binding component, wherein the single chain variable fragment (scFv) (e.g. 412) sequence comprises a CD19 binding component. In certain embodiments, the single chain variable fragment (scFv) sequence comprising a CD19 binding component comprises a CD19 binding component corresponding to an antibody heavy chain and light variable sequence, or CD19 binding fragments thereof. In some embodiments, the Fab-Fc-scFv heavy chain comprises SEQ ID NO: 209.

Fab-Fc-scFv:Fc Bispecific IgG

Figure 5:
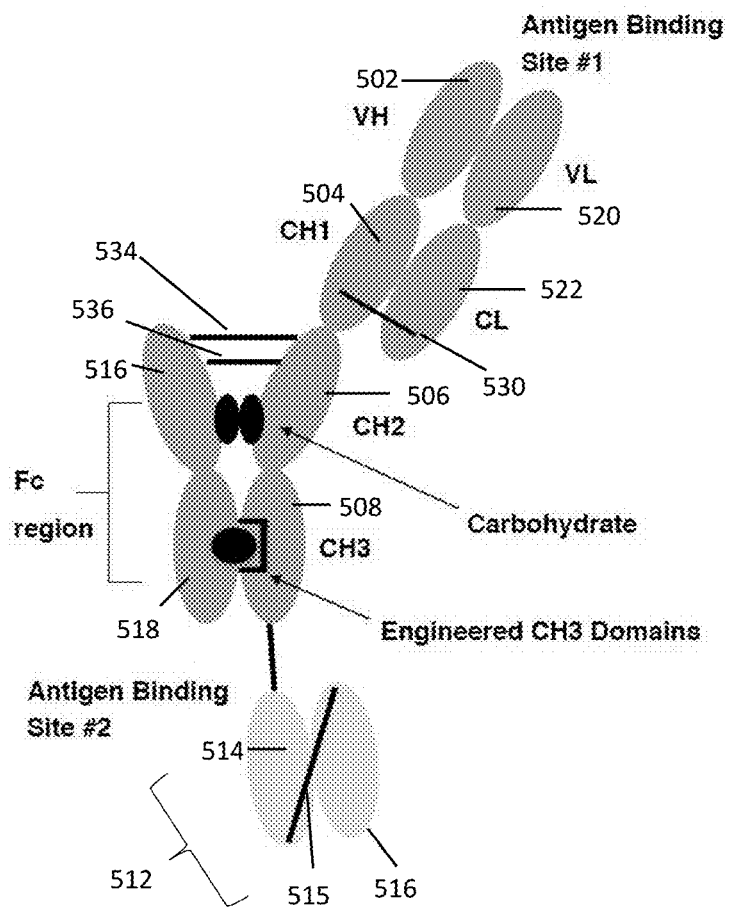
FIG. 5 illustrates the structure of a Fab-Fc-scFv:Fc bispecific IgG.

An engineered bispecific antibody having a Fab-Fc-scFv:Fc Bispecific IgG structure can be used herein. FIG. 5 illustrates a bispecific antibody having a Fab-Fc-scFv:Fc Bispecific IgG structure. The structure comprises a first heavy chain molecule and a second IgG heavy chain molecule. The first heavy chain comprises VH domain 502, CH1 domain 504, CH2 domain 506, CH3 domain 508, a linker 510, and a single chain variable fragment (scFv) 512, N-terminus to C-terminus respectively. The single chain variable fragment (scFv) can comprises a first domain 514 corresponding to a variable light chain domain, or fragment thereof, a second domain 516 corresponding to a variable heavy chain, or a fragment thereof, and a second linker polypeptide 515. The Fab-Fc-scFv:Fc Bispecific IgG structure also comprises a first light chain comprising a VL domain 520 and a CL domain 522. The Fab-Fc-scFv:Fc Bispecific IgG structure also comprises a second light chain comprising a VL domain 524 and a CL domain 526. A heavy chain can be covalently coupled to a light chain molecule via a covalent bond (e.g. disulfide bond 530). A heavy chain can be coupled to another heavy chain via one or more covalent bonds (e.g. disulfide bond 534 and/or 536). The Fab-Fc-scFv:Fc Bispecific IgG structure can comprise a first and a modified second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance) or biochemically (e.g. electrostatic interactions) prevent coupling of the two heavy chain molecules or two second heavy chain molecules. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The Fab-Fc-scFv:Fc Bispecific IgG structure can also comprise carbohydrate molecules 540 coupled thereto or additional modifications thereof.

A bispecific antibody having a Fab-Fc-scFv:Fc Bispecific IgG structure can target a B-cell lineage surface marker (e.g. CD19, CD138, IgA, or CD45.e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-scFv:Fc Bispecific IgG structure can be engineered so that a first antigen binding site targets CD19 and a second antigen binding site targets CD38. In some embodiments, the first heavy chain VH domain (e.g. 502) and VL domain (e.g. 520) comprises a CD19 binding component, wherein the single chain variable fragment (scFv) (e.g. 512) sequence comprises a CD38 binding component. In certain embodiments, the single chain variable fragment (scFv) sequence comprising a CD38 binding component comprises a CD38 binding component corresponding to an antibody heavy chain and light variable sequence, or CD38 binding fragments thereof.

The Fab-Fc-scFv:Fc Bispecific IgG structure can also be engineered so that a first antigen binding site targets CD38 and a second antigen binding site targets CD19. In some embodiments, the first heavy chain VH domain (e.g. 502) and VL domain (e.g. 520) comprises a CD38 binding component, wherein the single chain variable fragment (scFv) (e.g. 512) sequence comprises a CD19 binding component. In certain embodiments, the single chain variable fragment (scFv) sequence comprising a CD19 binding component comprises a CD19 binding component corresponding to an antibody heavy chain and light variable sequence, or CD19 binding fragments thereof.

Fab-Fc-Fab:Fab-Fc Bispecific IgG

Figure 6:
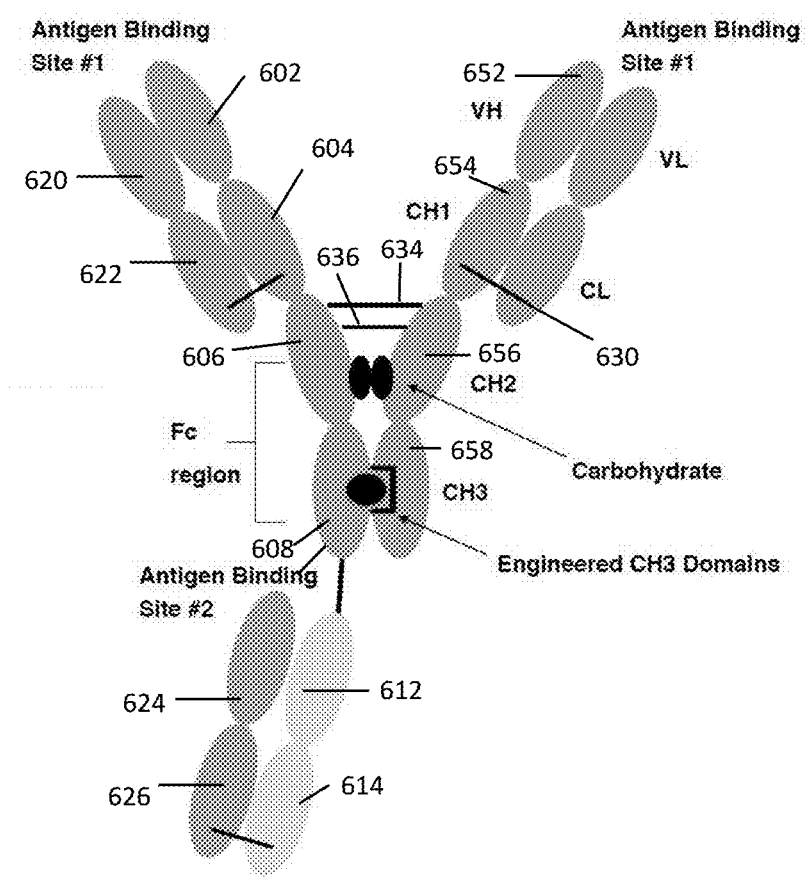
FIG. 6 illustrates the structure of a Fab-Fc-Fab:Fab-Fc bispecific IgG.

An engineered bispecific antibody having a Fab-Fc-Fab:Fab-Fc Bispecific IgG structure can be used herein. FIG. 6 illustrates a bispecific antibody having a Fab-Fc-Fab:Fab-Fc Bispecific IgG structure. The structure comprises a first heavy chain molecule and a second IgG heavy chain molecule. The first heavy chain comprises VH domain 602, CH1 domain 604, CH2 domain 606, CH3 domain 608, a linker 610 a second VH domain 612, and a second CH1 domain 614, N-terminus to C-terminus respectively. The second heavy chain comprises a VH domain 652, a CH1 domain 654, a CH2 domain 656, and CH3 domain 658, N-terminus to C-terminus respectively, as in that of the first heavy chain. The Fab-Fc-Fab:Fab-Fc Bispecific IgG structure also comprises a first light chain comprising a VL domain 620 and a CL domain 622. The Fab-Fc-Fab:Fab-Fc Bispecific IgG structure also comprises a second light chain comprising a VL domain 624 and a CL domain 626. A heavy chain can be covalently coupled to a light chain molecule via a covalent bond (e.g. disulfide bond 630). The first heavy chain and first light chain can be coupled in a manner that the VH domain and CH1 domain of the first heavy chain pair with the VL domain and CL domain of the first light chain. The first heavy chain and second light chain can be coupled in a manner that the second VH domain and second CH1 domain of the first heavy chain pair with the VL domain and CL domain of the second light chain. A heavy chain can be coupled to another heavy chain via one or more covalent bonds (e.g. disulfide bond 634 and/or 636). The Fab-Fc-Fab:Fab-Fc Bispecific IgG structure can comprise a first and a second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance) or biochemically (e.g. electrostatic interactions) prevent coupling of the two first heavy chain molecules or two second heavy chain molecules. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The Fab-Fc-Fab:Fab-Fc Bispecific IgG structure can also comprise carbohydrate molecules coupled thereto or additional modifications thereof.

A bispecific antibody having a Fab-Fc-Fab:Fab-Fc Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-Fab:Fab-Fc Bispecific IgG structure can be engineered so that a first antigen binding site targets CD19 and a second antigen binding site targets CD38. In some embodiments, the first heavy chain VH domain (e.g. 602) and VL domain (e.g. 620) comprises a CD19 binding component, wherein the second VH domain (e.g. 612) and VL domain (e.g. 624) comprises a CD38 binding component.

The Fab-Fc-Fab:Fab-Fc Bispecific IgG structure can also be engineered so that a first antigen binding site targets CD38 and a second antigen binding site targets CD19. In some embodiments, the first heavy chain VH domain (e.g. 602) and VL domain (e.g. 620) comprises a CD38 binding component, wherein the second VH domain (e.g. 612) and VL domain (e.g. 624) comprises a CD19 binding component.

scFv-Fab-Fc:scFv-Fab-Fc Bispecific IgG

Figure 7:
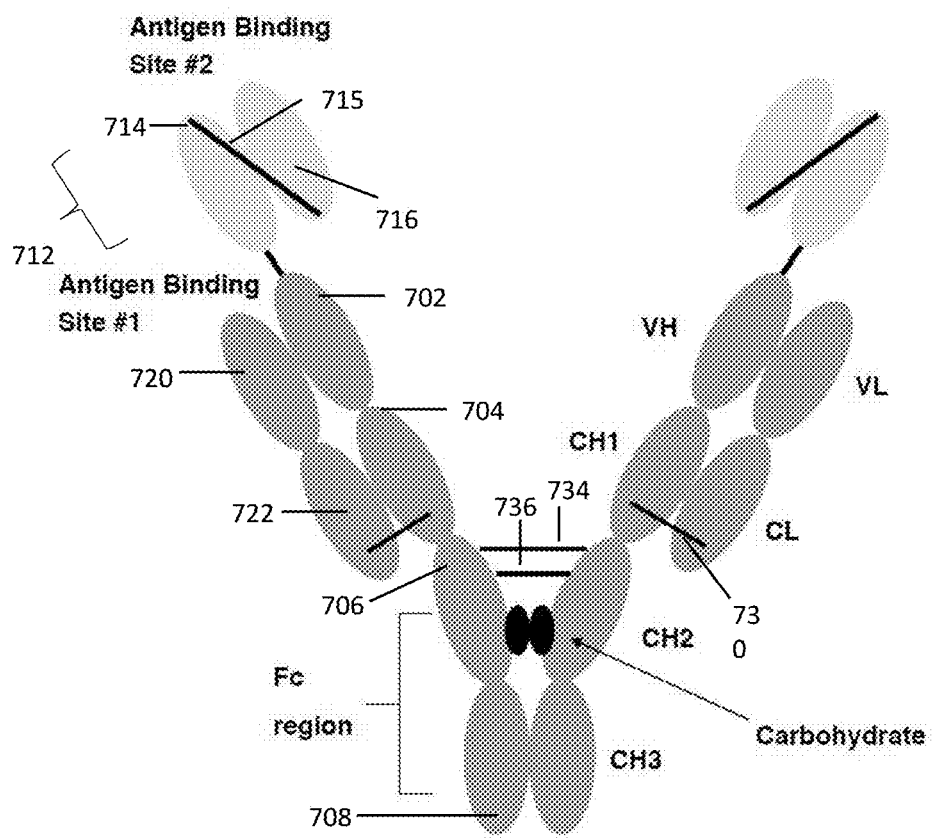
FIG. 7 illustrates the structure of an scFv-Fab-Fc:scFv-Fab-Fc bispecific IgG.

An engineered bispecific antibody having an scFv-Fab-Fc:scFv-Fab-Fc Bispecific IgG structure can be used herein. FIG. 7 illustrates a bispecific antibody having an scFv-Fab-Fc:scFv-Fab-Fc Bispecific IgG structure. The structure comprises a two first heavy chain molecules. The first heavy chain comprises a single chain variable fragment (scFv) 712, a linker 710, VH domain 702, CH1 domain 704, CH2 domain 706, and a CH3 domain 708, N-terminus to C-terminus respectively. The single chain variable fragment (scFv) can comprises a first domain 714 corresponding to a variable light chain domain, or fragment thereof, a second domain 716 corresponding to a variable heavy chain, or a fragment thereof, and a second linker polypeptide 715. The ScFv-Fab-Fc:scFv-Fab-Fc Bispecific IgG structure also comprises a first light chain comprising a VL domain 720 and a CL domain 722. A heavy chain can be covalently coupled to a light chain molecule via a covalent bond (e.g. disulfide bond 730). A heavy chain can be coupled to another heavy chain via one or more covalent bonds (e.g. disulfide bond 734 and/or 736). The ScFv-Fab-Fc:scFv-Fab-Fc Bispecific IgG structure can also comprise carbohydrate molecules 740 coupled thereto or additional modifications thereof.

A bispecific antibody having an scFv-Fab-Fc:scFv-Fab-Fc Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The scFv-Fab-Fc:scFv-Fab-Fc Bispecific IgG structure can be engineered so that a first antigen binding site targets CD19 and a second antigen binding site targets CD38. In some embodiments, the first heavy chain VH domain (e.g. 702) and VL domain (e.g. 720) comprises a CD19 binding component, wherein the single chain variable fragment (scFv) (e.g. 712) sequence comprises a CD38 binding component. In certain embodiments, the single chain variable fragment (scFv) sequence comprising a CD38 binding component comprises a CD38 binding component corresponding to an antibody heavy chain and light variable sequence, or CD38 binding fragments thereof.

The scFv-Fab-Fc:scFv-Fab-Fc Bispecific IgG structure can also be engineered so that a first antigen binding site targets CD38 and a second antigen binding site targets CD19. In some embodiments, the first heavy chain VH domain (e.g. 702) and VL domain (e.g. 720) comprises a CD38 binding component, wherein the single chain variable fragment (scFv) (e.g. 712) sequence comprises a CD19 binding component. In certain embodiments, the single chain variable fragment (scFv) sequence comprising a CD19 binding component comprises a CD19 binding component corresponding to an antibody heavy chain and light variable sequence, or CD19 binding fragments thereof.

Fab-Fab-Fc:Fab-Fab-Fc Bispecific IgG

Figure 8:
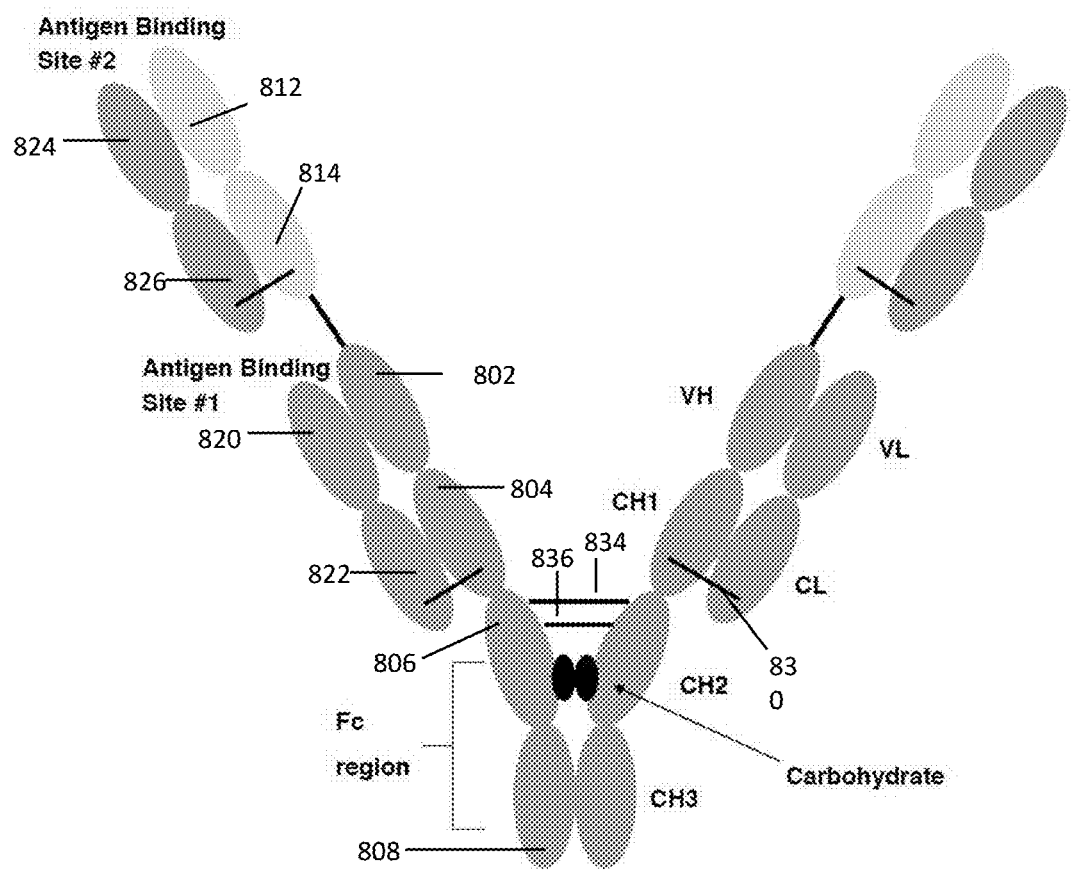
FIG. 8 illustrates the structure of a Fab-Fab-Fc:Fab-Fab-Fc bispecific IgG.

An engineered bispecific antibody having a Fab-Fab-Fc:Fab-Fab-Fc Bispecific IgG structure can be used herein. FIG. 8 illustrates a bispecific antibody having a Fab-Fab-Fc:Fab-Fab-Fc Bispecific IgG structure. The structure comprises two heavy chain molecules. The heavy chain comprises an additional VH domain 812, and an additional CH1 domain 814, a linker 810, VH domain 802, CH1 domain 804, CH2 domain 806, and a CH3 domain 808, N-terminus to C-terminus respectively. The Fab-Fab-Fc:Fab-Fab-Fc Bispecific IgG structure also comprises a first light chain comprising a VL domain 820 and a CL domain 822. The Fab-Fab-Fc:Fab-Fab-Fc Bispecific IgG structure also comprises a second light chain comprising a VL domain 824 and a CL domain 826. A heavy chain molecule can be covalently coupled to a light chain molecule via a covalent bond (e.g. disulfide bond 830). The heavy chain and first light chain can be coupled in a manner that the VH domain and CH1 domain of the heavy chain pair with the VL domain and CL domain of the first light chain. The heavy chain and second light chain can be coupled in a manner that the additional VH domain and additional CH1 domain of the heavy chain pair with the VL domain and CL domain of the second light chain. A heavy chain can be coupled to the modified second heavy chain via one or more covalent bonds (e.g. disulfide bond 834 and/or 836). The Fab-Fab-Fc:Fab-Fab-Fc Bispecific IgG structure can also comprise carbohydrate molecules 840 coupled thereto or additional modifications thereof.

A bispecific antibody having a Fab-Fab-Fc:Fab-Fab-Fc Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fab-Fc:Fab-Fab-Fc Bispecific IgG structure can be engineered so that a first antigen binding site targets CD19 and a second antigen binding site targets CD38. In some embodiments, the first VH domain (e.g. 802) and VL domain (e.g. 820) comprise a CD19 binding component, wherein the second VH domain (e.g. 812) and VL domain (e.g. 824) comprises a CD38 binding component.

The Fab-Fab-Fc:Fab-Fab-Fc Bispecific IgG structure can also be engineered so that a first antigen binding site targets CD38 and a second antigen binding site targets CD19. In some embodiments, the VH domain (e.g. 802) and VL domain (e.g. 820) comprises a CD38 binding component, wherein the second VH domain (e.g. 812) and VL domain (e.g. 824) comprises a CD19 binding component.

Fab-Fc-Fab:Fab-Fc-Fab Bispecific IgG

Figure 9:
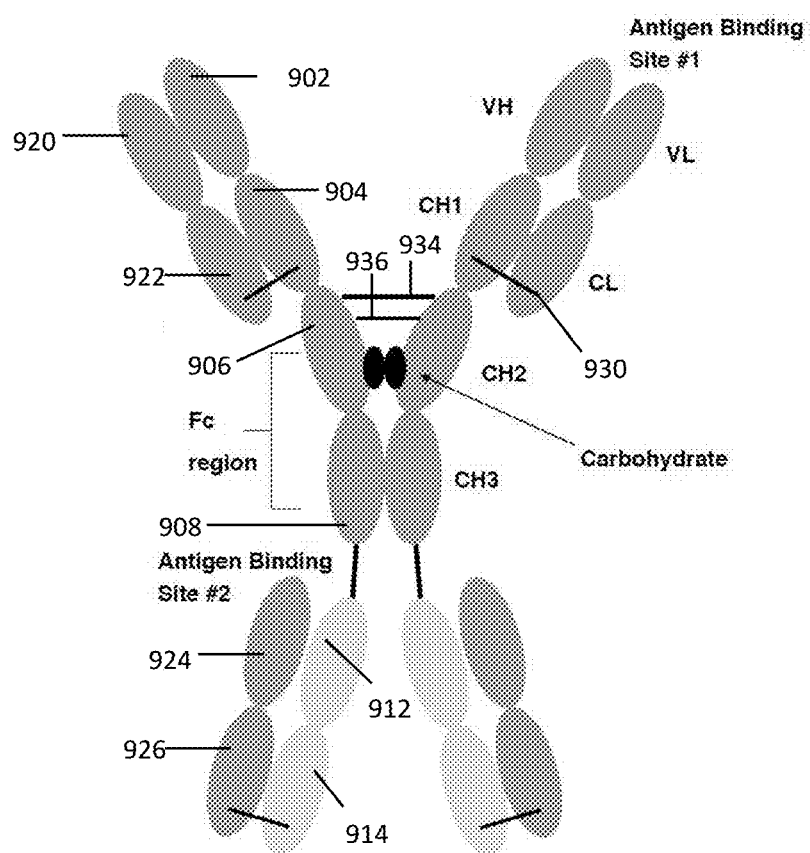
FIG. 9 illustrates the structure of a Fab-Fc-Fab:Fab-Fc-Fab bispecific IgG.

An engineered bispecific antibody having a Fab-Fc-Fab:Fab-Fc-Fab Bispecific IgG structure can be used herein. FIG. 9 illustrates a bispecific antibody having a Fab-Fc-Fab:Fab-Fc-Fab Bispecific IgG structure. The structure comprises two heavy chain molecules and two light chain molecules. The heavy chain comprises VH domain 902, CH1 domain 904, CH2 domain 906, CH3 domain 908, a linker 910 a second VH domain 912, and a second CH1 domain 914, N-terminus to C-terminus respectively. The Fab-Fc-Fab:Fab-Fc-Fab Bispecific IgG structure also comprises a first light chain comprising a VL domain 920 and a CL domain 922. The Fab-Fc-Fab:Fab-Fc-Fab Bispecific IgG structure also comprises a second light chain comprising a VL domain 924 and a CL domain 926. A heavy chain can be covalently coupled to a light chain molecule via a covalent bond (e.g. disulfide bond 930). The heavy chain and first light chain can be coupled in a manner that the VH domain and CH1 domain of the heavy chain pair with the VL domain and CL domain of the first light chain. The heavy chain and second light chain can be coupled in a manner that the second VH domain and second CH1 domain of the heavy chain pair with the VL domain and CL domain of the second light chain. A heavy chain can also be covalently coupled to another heavy chain molecule via a covalent bond (e.g. disulfide bond 934 and 936). The Fab-Fc-Fab Bispecific IgG structure can also comprise carbohydrate molecules 940 coupled thereto or additional modifications thereof.

A bispecific antibody having a Fab-Fc-Fab:Fab-Fc-Fab Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-Fab:Fab-Fc-Fab Bispecific IgG structure can be engineered so that a first antigen binding site targets CD19 and a second antigen binding site targets CD38. In some embodiments, the first VH domain (e.g. 902) and VL domain (e.g. 920) comprise a CD19 binding component, wherein the second VH domain (e.g. 912) and VL domain (e.g. 924) comprises a CD38 binding component.

The Fab-Fc-Fab:Fab-Fc-Fab Bispecific IgG structure can also be engineered so that a first antigen binding site targets CD38 and a second antigen binding site targets CD19. In some embodiments, the VH domain (e.g. 902) and VL domain (e.g. 920) comprises a CD38 binding component, wherein the second VH domain (e.g. 912) and VL domain (e.g. 924) comprises a CD19 binding component.

Fab-Fc-scFv:Fab-Fc Bispecific IgG

Figure 10:
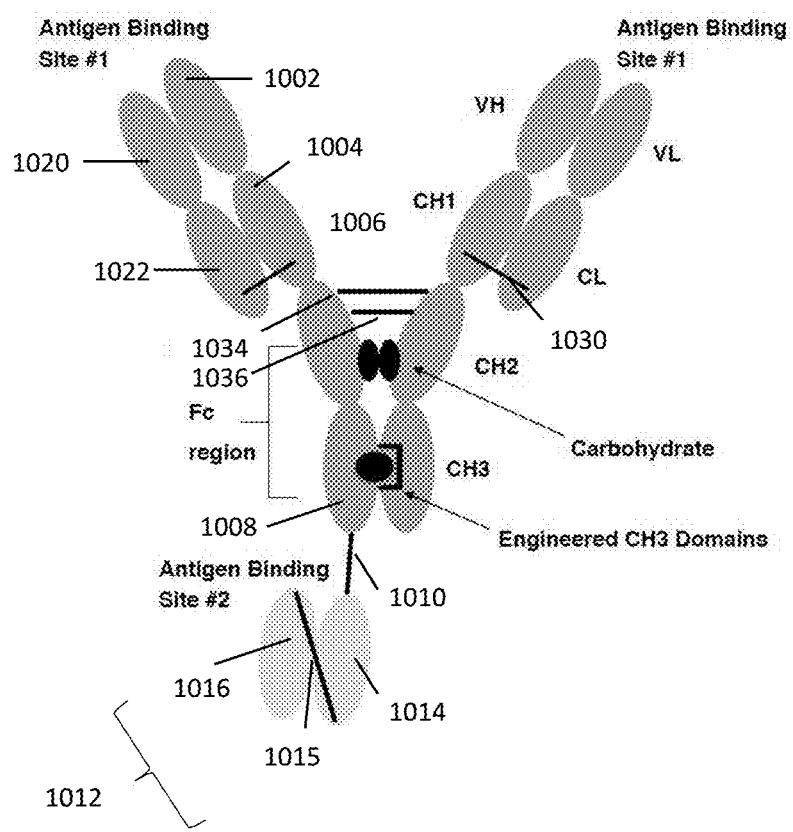
FIG. 10 illustrates the structure of a Fab-Fc-scFv:Fab-Fc bispecific IgG.

An engineered bispecific antibody having a Fab-Fc-scFv:Fab-Fc Bispecific IgG structure can be used herein. FIG. 10 demonstrates a bispecific antibody having a Fab-Fc-scFv:Fab-Fc Bispecific IgG structure. The structure comprises a first heavy chain molecule and a second IgG heavy chain molecule. The first heavy chain comprises VH domain 1002, CH1 domain 1004, CH2 domain 1006, CH3 domain 1008, a linker 1010 and a single chain variable fragment (scFv) 1012, N-terminus to C-terminus respectively. The single chain variable fragment (scFv) can comprises a first domain 1014 corresponding to a variable light chain domain, or fragment thereof, a second domain 1016 corresponding to a variable heavy chain, or a fragment thereof, and a second linker polypeptide 1015. The second heavy chain comprises a VH domain 1002, a CH1 domain 1004, a CH2 domain 1004, and CH3 domain 1008, N-terminus to C-terminus respectively, as in that of the first heavy chain. The Fab-Fc-scFv:Fab-Fc Bispecific IgG structure also comprises a first light chain comprising a VL domain 1020 and a CL domain 1022. A heavy chain can be covalently coupled to a light chain molecule via a covalent bond (e.g. disulfide bond 1030). A heavy chain can be coupled to another heavy chain via one or more covalent bonds (e.g. disulfide bond 1034 and/or 1036). The Fab-Fc-scFv:Fab-Fc Bispecific IgG structure can comprise a first and a second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. steric hinderance) or biochemically (e.g. electrostatic interactions) prevent coupling of the two first heavy chain molecules or two second heavy chain molecules. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The Fab-Fc-scFv:Fab-Fc Bispecific IgG structure can also comprise carbohydrate molecules 1040 coupled thereto or additional modifications thereof.

A bispecific antibody having a Fab-Fc-scFv:Fab-Fc Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The Fab-Fc-scFv:Fab-Fc Bispecific IgG structure can be engineered so that a first antigen binding site targets CD19 and a second antigen binding site targets CD38. In some embodiments, the first heavy chain VH domain (e.g. 1002) and VL domain (e.g. 1020) comprises a CD19 binding component, wherein the single chain variable fragment (scFv) (e.g. 1012) sequence comprises a CD38 binding component. In certain embodiments, the single chain variable fragment (scFv) sequence comprising a CD38 binding component comprises a CD38 binding component corresponding to an antibody heavy chain and light variable sequence, or CD38 binding fragments thereof.

Figure 11:
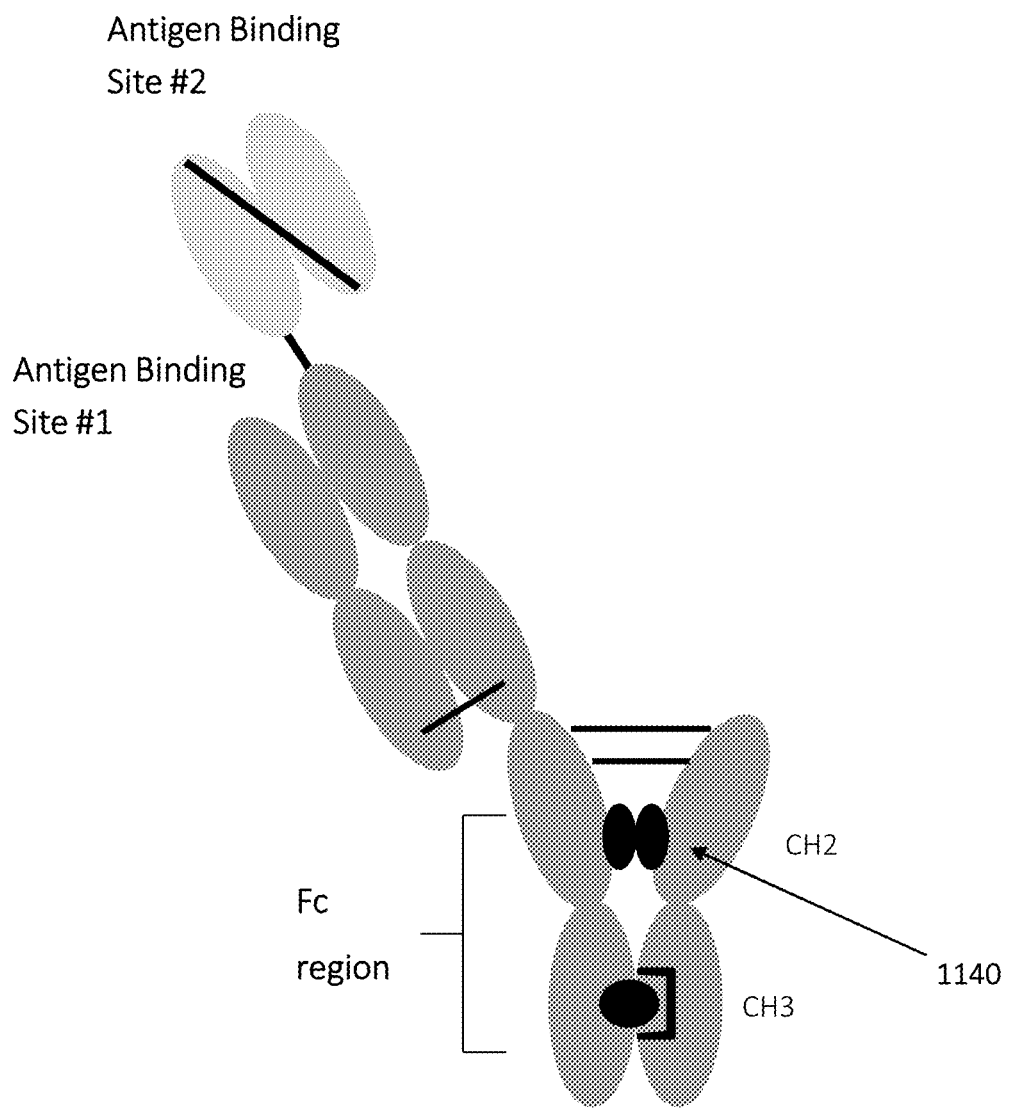
FIG. 11 illustrates the structure of an scFv-Fab-Fc:Fc Bispecific IgG

The Fab-Fc-scFv:Fab-Fc Bispecific IgG structure can also be engineered so that a first antigen binding site targets CD38 and a second antigen binding site targets CD19. In some embodiments, the first heavy chain VH domain (e.g. 1002) and VL domain (e.g. 1020) comprises a CD38 binding component, wherein the single chain variable fragment (scFv) (e.g. 1012) sequence comprises a CD19 binding component. In certain embodiments, the single chain variable fragment (scFv) sequence comprising a CD19 binding component comprises a CD19 binding component corresponding to an antibody heavy chain and light variable sequence, or CD19 binding fragments thereof scFv-Fab-Fc:Fc Bispecific IgG An engineered bispecific antibody having a scFv-Fab-Fc:Fc Bispecific IgG structure can be used herein. FIG. 11 demonstrates a bispecific antibody having a scFv-Fab-Fc:Fc Bispecific IgG structure. The structure comprises a first heavy chain molecule comprising an scFv, VH, and an Fc region and a second heavy chain molecule comprising an Fc. The scFv-Fab-Fc:Fc Bispecific IgG structure can comprise a first and a second heavy chain molecule that further comprises mutations within the CH3 domain that promote coupling of the first and the second heavy chain and/or prevent coupling of a first heavy chain to another first heavy chain or a second heavy chain to another second heavy chain. The mutations can physically (e.g. Knob-in hole architecture) or biochemically (e.g. electrostatic interactions) promote association of the first heavy chain molecule to the second heavy chain molecule. The scFv-Fab-Fc:Fc Bispecific IgG structure comprises a light chain molecule associated with the first heavy chain molecule that creates a first antigen binding site. A second antigen binding site is provided by an scFv fragment coupled to the N-terminal endo of the first heavy chain. Exemplary mutations that facilitate coupling of a first and a second heavy chain molecule are disclosed, for example in US PG-PUB: US20140322756 and "The making of bispecific antibodies" MAbs. 2017 February-March; 9(2): 182-212. The scFv-Fab-Fc:Fc Bispecific IgG structure can also comprise carbohydrate molecules 1140 coupled thereto or additional modifications thereof.

A bispecific antibody having an scFv-Fab-Fc:Fc Bispecific IgG structure can target a B-cell lineage surface marker (e.g. CD19, CD138, IgA, or CD45), and a suppressive B-cell surface marker (e.g. IgD, CD1, CD5, CD21, CD24, CD38, HM13, SLAMF7, AQP3, or latent TGF-beta (e.g., TGF-beta LAP)). In some embodiments, the B-cell lineage surface marker comprises CD19. In certain embodiments, the B-cell lineage surface marker consists of CD19. In some embodiments, the suppressive B-cell surface marker comprises CD38. In certain embodiments, the suppressive B-cell surface marker consists of CD38.

The scFv-Fab-Fc:Fc Bispecific IgG structure can be engineered so that a first antigen binding site targets CD19 and a second antigen binding site targets CD38. In some embodiments, the first heavy chain VH domain and VL domain comprises a CD19 binding component, wherein the single chain variable fragment (scFv) sequence comprises a CD38 binding component. In certain embodiments, the single chain variable fragment (scFv) sequence comprises a CD38 binding component corresponding to an antibody heavy chain and light variable sequence, or CD38 binding fragments thereof.

The scFv-Fab-Fc:Fc Bispecific IgG structure can also be engineered so that a first antigen binding site targets CD38 and a second antigen binding site targets CD19. In some embodiments, the heavy chain VH domain and VL domain comprises a CD38 binding component, wherein the single chain variable fragment (scFv) sequence comprises a CD19 binding component. In certain embodiments, the single chain variable fragment (scFv) sequence comprising a CD19 binding component comprises a CD19 binding component corresponding to an antibody heavy chain and light variable sequence, or CD19 binding fragments thereof.

In certain embodiments, the first heavy chain molecule comprises an amino acid sequence at least about 90%, 95%, 97%, 98%, or 99% identical to the amino acid sequence set forth in SEQ ID NO: 212. In certain embodiments, the first heavy chain molecule comprises an amino acid sequence identical to the amino acid sequence set forth in SEQ ID NO: 212.

In certain embodiments, the light chain molecule comprises an amino acid sequence at least about 90%, 95%, 97%, 98%, or 99% identical to the amino acid sequence set forth in SEQ ID NO: 213. In certain embodiments, the light chain molecule comprises an amino acid sequence identical to the amino acid sequence set forth in SEQ ID NO: 213.

In certain embodiments, the second heavy chain molecule comprises an amino acid sequence at least about 90%, 95%, 97%, 98%, or 99% identical to the amino acid sequence set forth in SEQ ID NO: 214. In certain embodiments, the first heavy chain molecule comprises an amino acid sequence identical to the amino acid sequence set forth in SEQ ID NO: 214.

Framework Region

Mutations or reversions to a germline sequence made within the framework regions of the heavy and light chains can be advantageous for improving the pharmacokinetic and pharmacodynamic properties of the CD19 and CD38 binding molecules described herein. In certain instances, mutations or reversions to a germline sequence made within a of the heavy and/or light chain improve stability of the CD19 and CD38 binding molecules (e.g. the bispecific antibodies described herein). In certain instances, mutations or reversions to a germline sequence made within a of the heavy and/or light chain reduce immunogenicity of the CD19 and CD38 binding molecules (e.g. the bispecific antibodies described herein). Accordingly, in some embodiments, a Framework Region of a heavy chain and/or light chain comprises 1, 2, 3, 4 5, 8, or 10 mutations or reversions back to a germline sequence. In some embodiments, the Framework Region of a heavy chain and/or light chain comprises 1 mutation or reversion back to a germline sequence to 10 mutations or reversions back to a germline sequence. In some embodiments, the Framework Region of a heavy chain and/or light chain comprises at least 1 mutation or reversion back to a germline sequence. In some embodiments, the Framework Region of a heavy chain and/or light chain comprises at most 10 mutations or reversions back to a germline sequence. In some embodiments, the Framework Region of a heavy chain and/or light chain comprises 1 mutation or reversion back to a germline sequence to 2 mutations or reversions back to a germline sequence, 1 mutation or reversion back to a germline sequence to 3 mutations or reversions back to a germline sequence, 1 mutation or reversion back to a germline sequence to 4 mutations or reversions back to a germline sequence, 1 mutation or reversion back to a germline sequence to 5 mutations or reversions back to a germline sequence, 1 mutation or reversion back to a germline sequence to 8 mutations or reversions back to a germline sequence, 1 mutation or reversion back to a germline sequence to 10 mutations or reversions back to a germline sequence, 2 mutations or reversions back to a germline sequence to 3 mutations or reversions back to a germline sequence, 2 mutations or reversions back to a germline sequence to 4 mutations or reversions back to a germline sequence, 2 mutations or reversions back to a germline sequence to 5 mutations or reversions back to a germline sequence, 2 mutations or reversions back to a germline sequence to 8 mutations or reversions back to a germline sequence, 2 mutations or reversions back to a germline sequence to 10 mutations or reversions back to a germline sequence, 3 mutations or reversions back to a germline sequence to 4 mutations or reversions back to a germline sequence, 3 mutations or reversions back to a germline sequence to 5 mutations or reversions back to a germline sequence, 3 mutations or reversions back to a germline sequence to 8 mutations or reversions back to a germline sequence, 3 mutations or reversions back to a germline sequence to 10 mutations or reversions back to a germline sequence, 4 mutations or reversions back to a germline sequence to 5 mutations or reversions back to a germline sequence, 4 mutations or reversions back to a germline sequence to 8 mutations or reversions back to a germline sequence, 4 mutations or reversions back to a germline sequence to 10 mutations or reversions back to a germline sequence, 5 mutations or reversions back to a germline sequence to 8 mutations or reversions back to a germline sequence, 5 mutations or reversions back to a germline sequence to 10 mutations or reversions back to a germline sequence, or 8 mutations or reversions back to a germline sequence to 10 mutations or reversions back to a germline sequence. In some embodiments, the Framework Region of a heavy chain and/or light chain comprises 1 mutation or reversion back to a germline sequence, 2 mutations or reversions back to a germline sequence, 3 mutations or reversions back to a germline sequence, 4 mutations or reversions back to a germline sequence, 5 mutations or reversions back to a germline sequence, 8 mutations or reversions back to a germline sequence, or 10 mutations or reversions back to a germline sequence. In some embodiments, the CD38 binding moiety comprises a heavy chain framework region as set forth in SEQ ID NO: 5. In some embodiments, the CD binding moiety comprises a heavy chain framework region as set forth in SEQ ID NO: 6 or 7.

Pharmaceutically Acceptable Excipients, Carriers, And Diluents

Compositions comprising the composite binding molecules of the current disclosure are included in a pharmaceutical composition comprising one or more pharmaceutically acceptable excipients, carriers, and diluents. In certain embodiments, the antibodies of the current disclosure are administered suspended in a sterile and/or isotonic solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween® 80), polysorbate 20 (Tween® 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

Subcutaneous formulations for administration of antibodies can comprise one or more of: buffers, for example, acetate, citrate, histidine, succinate, phosphate, bicarbonate and hydroxymethylaminomethane (Tris); surfactants, for example, polysorbate 80 (Tween® 80), polysorbate 20 (Tween® 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA. Additionally, a compound or molecule that relieves pain at the injection site can be included, such as hyaluronidase, for example at a concentration of from about 2,000 U/ml to about 12,000 U/ml.

In certain embodiments, the composite binding molecules of the current disclosure are shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

Also described herein are kits comprising one or more of the composite binding molecules described herein in a suitable container and one or more additional components selected from: instructions for use; a diluent, an excipient, a carrier, and a device for administration.

In certain embodiments, described herein is a method of preparing a cancer treatment comprising admixing one or more pharmaceutically acceptable excipients, carriers, or diluents and a composite binding molecule of the current disclosure. In certain embodiments, described herein is a method of preparing a cancer treatment for storage or shipping comprising lyophilizing one or more antibodies of the current disclosure.

Production and Manufacture

The nucleic acids encoding the composite binding molecules (e.g. bispecific antibodies) described herein can be used to infect, transfect, transform, or otherwise render a suitable cell transgenic for the nucleic acid, thus enabling the production of composite binding molecules for commercial or therapeutic uses. Standard cell lines and methods for the production of antibodies from a large-scale cell culture are known in the art. See e.g., Li et al., "Cell culture processes for monoclonal antibody production." Mabs. 2010 September-October; 2(5): 466-477.

In certain embodiments, a nucleic acid sequence encodes the composite binding molecule or bispecific antibodies disclosed herein. In certain embodiments, the polynucleotide sequence encoding the composite binding molecule is operatively coupled to a eukaryotic regulatory sequence. In some embodiments, a cell comprises the nucleic acid sequence.

In some embodiments, a cell comprises a nucleic acid encoding the composite binding molecules disclosed herein. In certain embodiments, the cell comprises a prokaryotic cell. In certain embodiments, the prokaryotic cell is an *Escherichia coli* cell. In certain embodiments, the cell comprises a eukaryotic cell. In certain embodiments, the eukaryotic cell is a Chines Hamster Ovary (CHO) cell, an NS0 murine myeloma cell, or a human PER.C6 cell In certain embodiments, described herein is a method of making a composite binding molecule comprising culturing a cell comprising a nucleic acid encoding a composite binding molecule under conditions in vitro sufficient to allow production and secretion of the composite binding molecules.

In certain embodiments, described herein, is a master cell bank comprising: (a) a mammalian cell line comprising a nucleic acid encoding an antibody described herein integrated at a genomic location; and (b) a cryoprotectant. In certain embodiments, the cryoprotectant comprises glycerol. In certain embodiments, the master cell bank comprises: (a) a CHO cell line comprising a nucleic acid encoding a composite binding molecule integrated at a genomic location; and (b) a cryoprotectant. In certain embodiments, the cryoprotectant comprises glycerol. In certain embodiments, the master cell bank is contained in a suitable vial or container able to withstand freezing by liquid nitrogen.

Also described herein are methods of making composite binding molecules described herein. Such methods comprise incubating a cell or cell-line comprising a nucleic acid encoding the composite binding molecules in a cell culture medium under conditions sufficient to allow for expression and secretion of the composite binding molecules, and further harvesting the composite binding molecules from the cell culture medium. The harvesting can further comprise one or more purification steps to remove live cells, cellular debris, non-composite binding molecules proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

Methods of Use

Suppression of the immune response by immunoregulatory cells can facilitate tumor growth, migration, and metastasis. Immunosuppression or negative immune modulation can include processes or pathways that result in the full or partial reduction of the immune response. Immunosuppression can be systemic or localized to a specific site (e.g. the tumor microenvironment), tissue, or region of a subject's or patient's body. Although B cells are primarily known as a positive immune modulator through the production of antibodies that facilitate neutralization of a pathogen, certain populations of B cells can function to suppress or negatively regulate the immune response. Such populations of B cells can be defined by the expression of more than one cell surface biomarkers. Immunosuppressive B cells or B-cell populations can comprise a B-cell linage surface biomarker and a suppressive B-cell surface biomarker. The B-cell lineage surface markers can comprise CD19, CD138, IgA, or CD45. B-cell surface markers can comprise IgD, CD1, CD5, CD21, CD24, CD38, HM13, SLAMF7, AQP3, or latent TGF-beta (e.g., TGF-beta LAP). Immunosuppressive B cells or immunosuppressive B-cell populations can function to suppress the immune response by suppressing a diverse set of cell subtypes, including T cells, through the secretion of anti-inflammatory mediators, such as cytokines. Immunosuppressive B cells can also function in attenuating the immune response by negatively modulating lymphoid structures and/or facilitating the conversion of T cells to regulatory T cells. Thus, disclosed herein are methods for targeting immunosuppressive B-cell populations to effectively modulate a response.

Targeting immunosuppressive B cells or B-cell populations can result in the immune activation or positive modulation of the immune response against a tumor or tumorigenic cell. Provided herein are methods of treating an individual afflicted with a cancer or a tumor comprising administering to the individual afflicted with the cancer or the tumor the composite binding molecules disclosed herein. Also provided herein are methods of reducing immunosuppressive B cells in, adjacent to, or surrounding a tumor of an individual afflicted with a tumor or cancer comprising administering to the individual afflicted with the tumor or the cancer the composite binding molecules disclosed herein, thereby reducing immunosuppressive B cells in, adjacent to, or surrounding the tumor. Further disclosed are methods of contacting an immunosuppressive B cell in a subject with a composite binding molecule, wherein the method comprises administering the composite binding molecule to the subject. In certain embodiments, the subject has a tumor or cancer.

The type, subtype, or form of a tumor or cancer can be an important factor in treatment strategies and methods. In some embodiments, the cancer or tumor is a hematologic cancer. In some embodiments, the cancer or tumor is a solid-tissue cancer. In some embodiments, the cancer comprises breast cancer, prostate cancer, pancreatic cancer, lung cancer, kidney cancer, stomach cancer, esophageal cancer, skin cancer, colorectal cancer, or head and neck cancer.

Immunosuppressive B cells can suppress the anti-tumor immune response. In some embodiments, the tumor or cancer comprise B cells comprising a B-cell linage surface biomarker and a suppressive B-cell surface biomarker. The B-cell lineage surface markers can comprise CD19, CD138, IgA, or CD45. B-cell surface markers can comprise IgD, CD1, CD5, CD21, CD24, CD38, HM13, SLAMF7, AQP3, or TGFB. In some embodiments, the B-cell surface markers comprise CD19 (e.g. CD19+) and CD38 (e.g. CD CD38+). In Some embodiments, the tumor infiltrating B cells or the immunosuppressive B cells comprise CD19+, CD38+ B cells.

In certain embodiments, disclosed herein, are bispecific antibodies useful for the treatment of a cancer or tumor. Treatment refers to a method that seeks to improve or ameliorate the condition being treated. With respect to cancer, treatment includes, but is not limited to, reduction of tumor volume, reduction in growth of tumor volume, increase in progression-free survival, or overall life expectancy. In certain embodiments, treatment will affect remission of a cancer being treated. In certain embodiments, treatment encompasses use as a prophylactic or maintenance dose intended to prevent reoccurrence or progression of a previously treated cancer or tumor. It is understood by those of skill in the art that not all individuals will respond equally or at all to a treatment that is administered, nevertheless these individuals are considered to be treated.

In certain embodiments, the cancer or tumor is a solid cancer or tumor. In certain embodiments, the cancer or tumor is a blood cancer or tumor. In certain embodiments, the cancer or tumor comprises breast, heart, lung, small intestine, colon, spleen, kidney, bladder, head, neck, ovarian, prostate, brain, pancreatic, skin, bone, bone marrow, blood, thymus, uterine, testicular, and liver tumors. In certain embodiments, tumors which can be treated with the antibodies of the invention comprise adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and/or teratoma. In certain embodiments, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPpoma, and Wilm's tumor. In certain embodiments, the tumor/cancer to be treated with one or more antibodies of the invention comprise brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer, and/or breast carcinoma. In certain embodiments, the cancer treated with the antibodies of this disclosure comprises glioblastoma. In certain embodiments, the cancer treated with one or more antibodies of this disclosure comprises pancreatic cancer. In certain embodiments, the cancer treated with one or more antibodies of this disclosure comprises ovarian cancer. In certain embodiments, the cancer treated with one or more antibodies of this disclosure comprises lung cancer. In certain embodiments, the cancer treated with one or more antibodies of this disclosure comprises prostate cancer. In certain embodiments, the cancer treated with one or more antibodies of this disclosure comprises colon cancer. In certain embodiments, the cancer treated comprises glioblastoma, pancreatic cancer, ovarian cancer, colon cancer, prostate cancer, or lung cancer. In a certain embodiment, the cancer is refractory to other treatment. In a certain embodiment, the cancer treated is relapsed. In a certain embodiment, the cancer is a relapsed/refractory glioblastoma, pancreatic cancer, ovarian cancer, colon cancer, prostate cancer, or lung cancer.

In certain embodiments the cancer and or tumor to be treated with the composite binding molecules herein is a Mature B-cell neoplasm: Chronic Lymphocytic Leukemia, Small Lymphocytic Lymphoma, Mantle Cell Lymphoma, Non-Hodgkins Lymphomas (Diffuse Large B-cell Lymphoma, Follicular Lymphoma), Mucosa-associated lymphatic tissue (MALT) lymphoma, Mediastinal (thymic) large B-cell lymphoma, Lymphoplasmacytic lymphoma and Waldenstrom macroglobulinemia, Nodal marginal zone B-cell lymphoma, Splenic marginal zone lymphoma, Extranodal marginal zone B-cell lymphoma, Intravascular large B-cell lymphoma, Primary effusion lymphoma, Burkitt lymphoma, or Primary central nervous system lymphoma.

In certain embodiments the cancer and or tumor to be treated with the composite binding molecules herein is a T cell neoplasm such as T-cell Non-Hodgkin Lymphoma, T-cell ALL, Mycosis Fungoides, Anaplastic Large Cell Lymphoma, Peripheral T-cell Lymphoma, T-Lymphocytic Leukemia (T-ALL), Acute Myeloblastic Leukemia, Acute Monocytic Leukemia, and others.

In certain embodiments, the antibodies can be administered to a subject in need thereof by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 5 mg/kg and about 30 mg/kg. Therapeutically effective amounts include amounts are those sufficient to ameliorate one or more symptoms associated with the disease or affliction to be treated.

Exemplary Embodiments

Provided herein are composite binding molecules comprising a CD19 binding component configured to bind CD19 and a CD38 binding component configured to bind CD38, wherein the CD19 binding component comprises an antibody or antigen binding fragment thereof and the CD38 binding component comprises an antibody or antigen binding fragment thereof. In some embodiments, provided is a composite binding molecule of any of the preceding embodiments, wherein the CD19 and/or CD38 binding component comprise an immunoglobulin heavy and light chain pair, an scFv, a F(ab), a F(ab')2, a single domain antibody, a variable region fragment from an immunoglobulin new antigen receptor (VNAR), or a variable region derived from a heavy chain antibody (VHH). In some embodiments, provided is a composite binding molecule of any of the preceding embodiments, wherein the CD19 or CD38 binding component comprises an immunoglobulin heavy and light chain pair. In some embodiments, provided is a composite binding molecule of any of the preceding embodiments, wherein the CD19 and CD38 binding component comprise an immunoglobulin heavy and light chain pair.

In some embodiments, provided is a composite binding molecule of any of the preceding embodiments, wherein the CD38 binding component comprises an immunoglobulin heavy chain and an immunoglobulin light chain, wherein the immunoglobulin heavy chain comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125; and wherein the CD19 binding component comprises an immunoglobulin heavy chain and an immunoglobulin light chain, wherein the immunoglobulin heavy chain comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125. In some embodiments, provided is a composite binding molecule of any of the preceding embodiments, wherein the CD 38 binding component comprises an immunoglobulin heavy chain comprising an amino acid sequence having at least about 90%, 95%, 97%, 99% identity to SEQ ID NO: 3; and the immunoglobulin light chain having at least about 90%, 95%, 97%, 99% identity to SEQ ID NO: 4; and/or wherein the CD19 binding component comprises an immunoglobulin heavy chain comprising an amino acid sequence having at least about 90%, 95%, 97%, 99% identity to SEQ ID NO: 1; and an immunoglobulin light chain having at least about 90%, 95%, 97%, 99% identity to SEQ ID NO: 4. In some embodiments, provided is a composite binding molecule of any of the preceding embodiments, wherein the immunoglobulin heavy chain comprises an amino acid sequence identical to that set forth in SEQ ID NO: 3 or 5; and the immunoglobulin light chain comprises an amino acid sequence identical to that set forth in SEQ ID NO: 4; and/or wherein the immunoglobulin heavy chain comprises an amino acid sequence identical to that set forth in SEQ ID NO: 1 or 6; and the immunoglobulin light chain comprises an amino acid sequence identical to that set forth in SEQ ID NO: 4.

In some embodiments, provided is a composite binding molecule of any of the preceding embodiments, wherein the composite binding molecule is a common light chain bispecific IgG. In some embodiments, provided is a composite binding molecule of any of the preceding embodiments, wherein the CD 38 binding component comprises an immunoglobulin heavy chain comprising an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125; and wherein the CD 19 binding component comprises an immunoglobulin heavy chain comprising an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In some embodiments, provided is a composite binding molecule of any of the preceding embodiments, wherein the immunoglobulin heavy chain comprises an amino acid sequence having at least about 90%, 95%, 97%, 99% identity to SEQ ID NO: 3 or 5; and the immunoglobulin light chain having at least about 90%, 95%, 97%, 99% identity to SEQ ID NO: 4; and/or wherein the immunoglobulin heavy chain comprises an amino acid sequence having at least about 90%, 95%, 97%, 99% identity to SEQ ID NO: 1 or 7; and the immunoglobulin light chain having at least about 90%, 95%, 97%, 99% identity to SEQ ID NO: 2.

In some embodiments, provided is a composite binding molecule of any of the preceding embodiments, wherein the immunoglobulin heavy chain comprises an amino acid sequence identical to that set forth in SEQ ID NO: 3 or 5; and the immunoglobulin light chain comprises an amino acid sequence identical to that set forth in SEQ ID NO: 4; and wherein the immunoglobulin heavy chain comprises an amino acid sequence identical to that set forth in SEQ ID NO: 1 or 7; and the immunoglobulin light chain comprises an amino acid sequence identical to that set forth in SEQ ID NO: 2. In some embodiments, provided is a composite binding molecule of any of the preceding embodiments, wherein the CD19 binding component or CD38 binding component comprise an scFv. In some embodiments, provided is a composite binding molecule of any of the preceding embodiments, wherein the CD19 binding component comprises an scFv. In some embodiments, provided is a composite binding molecule of any of the preceding embodiments, wherein the CD38 binding component comprises an scFv. In some embodiments, provided is a composite binding molecule of any of the preceding embodiments, wherein the CD19 binding component or CD38 binding component comprise an immunoglobulin heavy-chain/light chain pair. In some embodiments, provided is a composite binding molecule of any of the preceding embodiments, wherein the CD19 binding component comprises an immunoglobulin heavy-chain/light chain pair. In some embodiments, provided is a composite binding molecule of any of the preceding embodiments, wherein the CD38 binding component comprises an immunoglobulin heavy-chain/light chain pair.

Further provided are composite binding molecules, wherein the composite binding molecule comprises a CD38 antigen binding component that binds CD38 comprising an anti-CD38 immunoglobulin heavy chain variable region paired with an anti-CD38 immunoglobulin light chain variable region and a CD19 antigen binding component that binds CD19 comprising an anti-CD19 immunoglobulin heavy chain variable region paired with an anti-CD38 immunoglobulin light chain variable region, wherein the CD38 antigen binding component comprises: a) a heavy chain complementarity determining region 1 (HCDR1) comprising an amino acid sequence set forth in any one of SEQ ID NOs: 71-75; b) a heavy chain complementarity determining region 2 (HCDR2) comprising an amino acid sequence set forth in any one of SEQ ID NOs: 81-85, or 150-155, c) a heavy chain complementarity determining region 3 (HCDR3) comprising an amino acid sequence set forth in any one of SEQ ID NOs: 91-95; d) a light chain complementarity determining region 1 (LCDR1) comprising an amino acid sequence set forth in any one of SEQ ID NOs: 101-105; e) a light chain complementarity determining region 2 (LCDR2) comprising an amino acid sequence set forth in any one of SEQ ID NOs: 111-115; and/or f) a light chain complementarity determining region 3 (LCDR3) comprising an amino acid sequence set forth in any one of SEQ ID NOs: 121-125.

In some embodiments, provided is a composite binding molecule of any of the preceding embodiments, wherein the CD19 antigen binding component comprises: g) a heavy chain complementarity determining region 1 (HCDR1) comprising an amino acid sequence set forth in any one of SEQ ID NOs: 11-15, h) a heavy chain complementarity determining region 2 (HCDR2) comprising an amino acid sequence set forth in any one of SEQ ID NOs: 21-25, i) a heavy chain complementarity determining region 3 (HCDR3) comprising an amino acid sequence set forth in any one of SEQ ID NOs: 31-35; j) a light chain complementarity determining region 1 (LCDR1) comprising an amino acid sequence set forth in any one of SEQ ID NOs: 101-105; k) a light chain complementarity determining region 2 (LCDR2) comprising an amino acid sequence set forth in any one of SEQ ID NOs: 111-115; and/or 1) a light chain complementarity determining region 3 (LCDR3) comprising an amino acid sequence set forth in any one of SEQ ID NOs: 121-125.

In some embodiments, provided is a composite binding molecule of any of the preceding embodiments, wherein the CD38 antigen binding component comprises an immunoglobulin heavy chain variable region comprising an amino acid sequence having at least about 90%, 95%, 97%, 99% identity to SEQ ID NO: 3 or 5; and an immunoglobulin light chain variable region comprising an amino acid sequence having at least about 90%, 95%, 97%, 99% identity to SEQ ID NO: 4. In some embodiments, provided is a composite binding molecule of any of the preceding embodiments, wherein the CD38 antigen binding component comprises an immunoglobulin heavy chain variable region comprising an amino acid sequence identical to SEQ ID NO: 3 or 5; and an immunoglobulin light chain variable region comprises an amino acid sequence identical to SEQ ID NO: 4. In some embodiments, provided is a composite binding molecule of any of the preceding embodiments, wherein the CD19 antigen binding component comprises an anti-CD19 immunoglobulin heavy chain variable region comprising an amino acid sequence having at least about 90%, 95%, 97%, 99% identity to SEQ ID NO: 1 or 6; and an immunoglobulin light chain variable region comprising an amino acid sequence having at least about 90%, 95%, 97%, 99% identity to SEQ ID NO: 4.

In some embodiments, provided is a composite binding molecule of any of the preceding embodiments, wherein the anti-CD19 antigen binding component comprises an immunoglobulin heavy chain variable region comprising an amino acid sequence identical to SEQ ID NO: 1 or 6; and an immunoglobulin light chain variable region comprises an amino acid sequence identical to SEQ ID NO: 4. In some embodiments, provided is a composite binding molecule of any of the preceding embodiments, wherein the anti-CD38 immunoglobulin heavy chain variable region further comprises a first immunoglobulin heavy chain constant region. In some embodiments, provided is a composite binding molecule of any of the preceding embodiments, wherein the anti-CD38 immunoglobulin light chain variable region further comprises an immunoglobulin light chain constant region. In some embodiments, provided is a composite binding molecule of any of the preceding embodiments, wherein the anti-CD19 immunoglobulin heavy chain variable region further comprises a second immunoglobulin heavy chain constant region. In some embodiments, provided is a composite binding molecule of any of the preceding embodiments, wherein the first immunoglobulin heavy chain constant region and/or the second immunoglobulin heavy chain constant region comprises one or more amino acid substitutions that disfavors homodimerization of the anti-CD38 immunoglobulin heavy chain constant region and/or promotes heterodimerization of the first heavy chain constant region and the second heavy chain constant region. In some embodiments, provided is a composite binding molecule of any of the preceding embodiments, wherein the one of the first or second immunoglobulin heavy chain constant regions comprises a T366W substitution (EU numbering), and the other of the first or second immunoglobulin heavy chain constant regions comprises a T366S/L368A/Y407V substitution (EU numbering), such that the heterodimerization of the first and second immunoglobulin heavy chain constant regions is favored compared to homodimerization of the first or second immunoglobulin heavy chain constant regions. In some embodiments, provided is a composite binding molecule of any of the preceding embodiments, wherein a single bispecific binding molecule is formed from the CD38 antigen binding component and the CD19 antigen binding component.

Also provided are composite binding molecules comprising a CD19 binding component that binds to CD19 and a CD38 binding component that binds to CD38, wherein the CD19 binding component comprises an scFV that binds to CD19, and the CD38 binding component comprises an immunoglobulin variable region comprising a light-chain variable region and a heavy-chain variable region that bind to CD38. In some embodiments, provided is a composite binding molecule of any of the preceding embodiments, wherein the scFv that binds to CD19 is coupled to a first immunoglobulin heavy chain constant region. In some embodiments, provided is a composite binding molecule of any of the preceding embodiments, wherein the heavy-chain variable region of the CD38 binding component further comprises a second immunoglobulin heavy chain constant region. In some embodiments, provided is a composite binding molecule of any of the preceding embodiments, wherein the light-chain variable region of the CD38 binding component further comprises an immunoglobulin light chain constant region. In some embodiments, provided is a composite binding molecule of any of the preceding embodiments, wherein the CD19 binding component comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35; and the immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65.

In some embodiments, provided is a composite binding molecule of any of the preceding embodiments, wherein the CD38 binding component comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and the immunoglobulin light chain comprises an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125. In some embodiments, provided is a composite binding molecule of any of the preceding embodiments, wherein the CD19 binding component comprises an amino acid sequence having at least about 90%, 95%, 97%, 99% identity to SEQ ID NO: 1 or 7; and the immunoglobulin light chain having at least about 90%, 95%, 97%, 99% identity to SEQ ID NO: 2. In some embodiments, provided is a composite binding molecule of any of the preceding embodiments, wherein the CD38 binding component comprises an amino acid sequence having at least about 90%, 95%, 97%, 99% identity to SEQ ID NO: 3 or 5; and an amino acid sequence having at least about 90%, 95%, 97%, 99% identity to SEQ ID NO: 4. In some embodiments, provided is a composite binding molecule of any of the preceding embodiments, wherein the CD19 binding component comprises an amino acid sequence identical to that set forth in SEQ ID NO: 1 or 7; and an amino acid sequence identical to that set forth in SEQ ID NO: 2. In some embodiments, provided is a composite binding molecule of any of the preceding embodiments, wherein the CD38 binding component comprises an amino acid sequence identical to that set forth in SEQ ID NO: 3 or 5; and an amino acid sequence identical to that set forth in SEQ ID NO: 4.

In some embodiments, provided is a composite binding molecule of any of the preceding embodiments, wherein the first immunoglobulin heavy chain constant region and/or the second immunoglobulin heavy chain constant region comprises one or more amino acid substitutions that disfavors homodimerization of the anti-CD38 immunoglobulin heavy chain constant region and/or promotes heterodimerization of the first heavy chain constant region and the second heavy chain constant region. In some embodiments, provided is a composite binding molecule of any of the preceding embodiments, wherein the one of the first or second immunoglobulin heavy chain constant regions comprises a T366W substitution (EU numbering), and the other of the first or second immunoglobulin heavy chain constant regions comprises a T366S/L368A/Y407V substitution (EU numbering), such that the heterodimerization of the first and second immunoglobulin heavy chain constant regions is favored over homodimerization of the first or second immunoglobulin heavy chain constant regions. In some embodiments, provided is a composite binding molecule of any of the preceding embodiments, wherein single bispecific binding molecule is formed from the CD38 antigen binding component and the CD19 antigen binding component.

In some embodiments, provided is a composite binding molecule of any of the preceding embodiments, wherein composite binding molecule is a bispecific antibody or dual-antigen binding fragment thereof. In some embodiments, provided is a composite binding molecule of any of the preceding embodiments, comprising an Fc region comprising a native carbohydrate or an afucosylated carbohydrate modified amino acid residue. In some embodiments, provided is a composite binding molecule of any of the preceding embodiments, wherein the native carbohydrate or the afucosylated carbohydrate modified amino acid residue corresponds to Asparagine 297 according to EU numbering.

In some embodiments, provided is a composite binding molecule of any of the preceding embodiments, wherein the composite binding molecule binds to CD19+, CD38+ B cells. In some embodiments, provided is a composite binding molecule of any of the preceding embodiments, wherein the composite binding molecule binds exhibits reduced hemagglutination compared to a CD19 or CD38 monospecific antibody comprising an Fc region.

Provided are nucleic comprising a polynucleotide sequence encoding the composite binding molecule of any one of composite binding molecules of the preceding embodiments. Embodiment 49: The nucleic acid of embodiment 47, wherein the polynucleotide sequence encoding the composite binding molecule is operatively coupled to a eukaryotic regulatory sequence. In some embodiments, provided is a cell comprising the nucleic acid of embodiment any one of the preceding embodiments. In some embodiments, provided is a cell of any of the preceding embodiments, wherein the cell comprises a prokaryotic cell. In some embodiments, provided is a cell of any of the preceding embodiments, wherein the prokaryotic cell is an *Escherichia coli* cell. In some embodiments, provided is a cell of any of the preceding embodiments, wherein the cell comprises a eukaryotic cell. In some embodiments, provided is a cell of any of the preceding embodiments, wherein the eukaryotic cell is a Chinese Hamster Ovary (CHO) cell, an NS0 murine myeloma cell, or a human PER.C6 cell.

Also provided are pharmaceutical compositions, for example, composition comprising the composite binding molecule of any one of the preceding embodiments and a pharmaceutically acceptable diluent, carrier, or excipient. In some embodiments, composition is formulated for intravenous administration. In some embodiments, composition is formulated for subcutaneous administration.

Provided are composite binding molecules of any one of the preceding embodiments or the pharmaceutical composition of any one of the preceding embodiments for use in a method of treating a tumor or a cancer in an individual. In some embodiments, the tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

In some embodiments, the cancer or the tumor is a solid-tissue cancer. In some embodiments, the solid-tissue cancer comprises breast cancer, prostate cancer, pancreatic cancer, lung cancer, kidney cancer, stomach cancer, esophageal cancer, skin cancer, colorectal cancer, brain cancer, or head and neck cancer. In some embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma.

Provided are also composite binding molecules of any one of the preceding embodiments or the pharmaceutical composition of any one of the preceding embodiments for use in a method of reducing immunosuppressive B cells in, adjacent to, or surrounding a tumor of an individual. In some embodiments, Further provided are composite binding molecules of any one of the preceding embodiments or the pharmaceutical composition of any one of the preceding embodiments for use in a method of reducing immunosuppressive B cells in, adjacent to, or surrounding a tumor of an individual. In some embodiments, the tumor infiltrating B cells or the immunosuppressive B cells comprise CD19+, CD38+ B cells.

In some embodiments, provided is a composite binding molecule of any of the preceding embodiments, wherein the CD38 binding component comprises a HCDR2 amino acid sequence comprising the sequence P-X1-LG-X2-A (SEQ ID NO: 156), wherein X1 and X2 are each selected from the group consisting of H, Q, T, N, S, G, A, R, K, D, or E. In certain embodiments, the X1 is H and X2 is T. In some embodiments, provided is a composite binding molecule of any of the preceding embodiments, X1 is H and X2 is T. In some embodiments, provided is a composite binding molecule of any of the preceding embodiments, wherein a heavy chain constant region of the CD19 binding component comprises a A84S and/or A108L modification. In certain embodiments, provided is a composite binding molecule of any of the preceding embodiments, wherein the CD38 binding component comprises a light chain sequence comprising a W32H substitution.

Further provided are methods of treating an individual afflicted with a cancer or a tumor comprising administering to the individual afflicted with the cancer or the tumor the composite binding molecule of any one of the preceding embodiments or the pharmaceutical composition of any one of the preceding embodiments, thereby treating the cancer or tumor. In some embodiments, the cancer or tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

In some embodiments, the cancer or tumor is a solid-tissue cancer. In some embodiments, the solid-tissue cancer comprises breast cancer, prostate cancer, pancreatic cancer, lung cancer, kidney cancer, stomach cancer, esophageal cancer, skin cancer, colorectal cancer, or head and neck cancer. In some embodiments, the breast cancer is triple negative breast cancer, the lung cancer is non-small cell lung cancer, the head and neck cancer is head and neck squamous cell cancer, the kidney cancer is renal cell carcinoma, the brain cancer is glioblastoma multiforme, or the skin cancer is melanoma.

Provided are methods of reducing immunosuppressive B cells in, adjacent to, or surrounding a tumor of an individual afflicted with a tumor or cancer comprising administering to the individual afflicted with the tumor or the cancer the composite binding molecule of any one of the preceding embodiments or the pharmaceutical composition of any one of the preceding embodiments, thereby reducing immunosuppressive B cells in the tumor.

Also provided are methods of reducing immunosuppressive B cells in, adjacent to, or surrounding a tumor of an individual afflicted with a tumor or cancer comprising administering to the individual afflicted with the tumor or the cancer the composite binding molecule of any one of the preceding embodiments or the pharmaceutical composition of any one of the preceding embodiments, thereby reducing immunosuppressive B cells in the tumor. In some embodiments, the tumor infiltrating B cells or the immunosuppressive B cells comprise CD19+, CD38+ B cells.

Provided herein are also methods of making the composite binding molecule of any one of the preceding embodiments comprising incubating the cell of the preceding embodiments in a cell culture medium under conditions sufficient to allow expression, assembly, and secretion of the composite binding molecule into the cell culture medium. In some embodiments, the method comprises comprising isolating and purifying the molecule from the cell culture medium. Also provided are methods of preparing a cancer treatment for an individual comprising admixing the composite binding molecule of any one of the preceding embodiments with a pharmaceutically acceptable diluent, carrier, or excipient.

Thus, provided herein is a composite binding molecule comprising a first binding component configured to bind a first target and a second binding component configured to bind a second target, wherein the first target comprises a B-cell lineage surface marker, and wherein the second target comprises a suppressive B-cell surface marker, wherein the first target and the second target are not identical. In some embodiments, the first or the second binding component comprises a polypeptide. In certain embodiments, the first or the second binding component consists of a polypeptide. In some embodiments, the first and the second binding component comprise a polypeptide. In certain embodiments, the first and the second binding component consist of a polypeptide. In some embodiments, the polypeptide of the first or second binding component comprises an amino acid sequence at least 100 amino acid residues in length. In some embodiments, the polypeptide of the first and second binding component comprise an amino acid sequence at least 100 amino acid residues in length.

The B-cell lineage surface marker can comprise CD19, CD138, IgA, or CD45. In some embodiments, the B-cell lineage surface marker comprises CD19. In certain embodiments, the B-cell lineage surface marker is CD19. In some embodiments, the B-cell lineage surface marker is IgA. In certain embodiments, the B-cell lineage surface marker is IgA. In some embodiments, the B-cell lineage surface marker is CD138. In certain embodiments, the B-cell lineage surface marker is CD138. In some embodiments, the B-cell lineage surface marker is CD45. In certain embodiments, the B-cell lineage surface marker is CD45. In some embodiments, the B-cell lineage surface marker is selected from the group consisting of IgA, CD19, CD138, CD45, and any combination thereof.

The suppressive B-cell surface marker can comprise IgD, CD1, CD5, CD21, CD24, CD38, HM13, SLAMF7, AQP3, or latent TGF-beta (e.g., TGF-beta LAP). In some embodiments, the suppressive B-cell surface marker comprises IgD. In certain embodiments, the suppressive B-cell surface marker is IgD. In some embodiments, the suppressive B-cell surface marker comprises CD1. In certain embodiments, the suppressive B-cell surface marker is CD1. In some embodiments, the suppressive B-cell surface marker comprises CD5. In certain embodiments, the suppressive B-cell surface marker is CD5. In some embodiments, the suppressive B-cell surface marker comprises CD21. In certain embodiments, the suppressive B-cell surface marker is CD21. In some embodiments, the suppressive B-cell surface marker comprises CD24. In certain embodiments, the suppressive B-cell surface marker is CD24. In some embodiments, the suppressive B-cell surface marker comprises CD38. In certain embodiments, the suppressive B-cell surface marker is CD38. In some embodiments, the B-cell surface marker is selected from the group consisting of IgD, CD1, CD5, CD21, CD24, CD38, HM13, SLAMF7, AQP3, latent TGF-beta (e.g., TGF-beta LAP), and any combination thereof.

The composite binding molecule can comprise an antibody or target-binding fragments thereof. In some embodiments, the first or second binding component comprise an immunoglobulin heavy and light chain pair, an scFv, a F(ab), a F(ab')2, a single domain antibody, a variable region fragment from an immunoglobulin new antigen receptor ($V_{NAR}$), or a variable region derived from a heavy chain antibody (VHH). In some embodiments, the first and second binding component comprise an immunoglobulin heavy and light chain pair, an scFv, a F(ab), a F(ab')2, a single domain antibody, a variable region fragment from an immunoglobulin new antigen receptor (VNAR), or a variable region derived from a heavy chain antibody (VHH). In certain embodiments, the first or second binding component comprises an immunoglobulin heavy and light chain pair. In certain embodiments, the first and second binding component comprise an immunoglobulin heavy and light chain pair. In certain embodiments, the first or second binding component comprises an scFv. In certain embodiments, the first and second binding component comprise an scFv.

The composite binding molecule described herein, wherein composite binding molecule is a bispecific antibody or dual-antigen binding fragment thereof.

In some embodiments, the composite binding molecule comprises an immunoglobulin heavy chain and an immunoglobulin light chain, wherein the immunoglobulin heavy chain comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95; and an immunoglobulin light chain comprises an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In certain embodiments, the immunoglobulin heavy chain comprises an amino acid sequence having at least about 90%, 95%, 97%, 99% identity to SEQ ID NO: 3; and the immunoglobulin light chain having at least about 90%, 95%, 97%, 99% identity to SEQ ID NO: 2. In certain embodiments, the immunoglobulin heavy chain comprises an amino acid sequence identical to that set forth in SEQ ID NO: 3; and the immunoglobulin light chain comprises an amino acid sequence identical to that set forth in SEQ ID NO: 2. In some embodiments, the composite binding molecule is a common light chain bispecific IgG.

The composite binding molecule can be a bispecific antibody. In some embodiments, the bispecific antibody is selected from one of the following formats: a common light chain bispecific IgG, a Fab-Fc:scFv-Fc bispecific IgG, a Fab-Fc-Fab:Fc bispecific IgG, a Fab-Fc-scFv:Fab-Fc-scFv bispecific IgG, a Fab-Fc-scFv:Fc bispecific IgG, a Fab-Fc-Fab:Fab-Fc bispecific IgG, an scFv-Fab-Fc:scFv-Fab-Fc bispecific IgG, a Fab-Fab-Fc:Fab-Fab-Fc bispecific IgG, a Fab-Fc-Fab:Fab-Fc-Fab bispecific IgG, and a Fab-Fc-scFv:Fab-Fc bispecific IgG. In certain embodiments, the bispecific antibody is a common light chain bispecific IgG. In certain embodiments, the bispecific antibody is a Fab-Fc:scFv-Fc bispecific IgG. In certain embodiments, the bispecific antibody is a Fab-Fc-Fab:Fc bispecific IgG. In certain embodiments, the bispecific antibody is a Fab-Fc-scFv:Fab-Fc-scFv bispecific IgG. In certain embodiments, the bispecific antibody is a Fab-Fc-scFv:Fc bispecific IgG. In certain embodiments, the bispecific antibody is a Fab-Fc-Fab:Fab-Fc bispecific IgG. In certain embodiments, the bispecific antibody is an scFv-Fab-Fc:scFv-Fab-Fc bispecific IgG. In certain embodiments, the bispecific antibody is a Fab-Fab-Fc:Fab-Fab-Fc bispecific IgG. In certain embodiments, the bispecific antibody is a Fab-Fc-Fab:Fab-Fc-Fab bispecific IgG. In certain embodiments, the bispecific antibody is an IgG-scFv The composite binding molecule can comprise post-translational modification. In some embodiments, the composite binding molecule comprises an Fc region comprising a native carbohydrate or an afucosylated carbohydrate modified amino acid residue. In certain embodiments, the native carbohydrate or the afucosylated carbohydrate modified amino acid residue corresponds to Asparagine 297 according to EU numbering.

In some embodiments, the first binding component comprises an HCDR1 amino acid sequence set forth in any one of SEQ ID NOs: 11-15, an HCDR2 amino acid sequence set forth in any one of SEQ ID NOs: 21-25, an HCDR3 amino acid sequence set forth in any one of SEQ ID NOs: 31-35, an LCDR1 amino acid sequence set forth in any one of SEQ ID NOs: 41-45, an LCDR2 amino acid sequence set forth in any one of SEQ ID NOs: 51-55, and/or an LCDR3 amino acid sequence set forth in any one of SEQ ID NOs: 61-65. In certain embodiments, the first binding component comprises an amino acid sequence comprising at least about 90%, 95%, 97%, 99% identity to, or is 100% identical to the amino acid sequence set forth in any one of SEQ ID NOs: SEQ ID NO: 1 and SEQ ID NO: 2. In certain embodiments, the first binding component comprises an amino acid sequence comprising at least about 90%, 95%, 97%, 99% identity to, or is 100% identical to the amino acid sequence set forth in SEQ ID NO: 1 and SEQ ID NO: 2.

In some embodiments, the second binding component comprises an HCDR1 amino acid sequence set forth in any one of SEQ ID NOs: 71-75, an HCDR2 amino acid sequence set forth in any one of SEQ ID NOs: 81-85, or 150-155, an HCDR3 amino acid sequence set forth in any one of SEQ ID NOs: 91-95, an LCDR1 amino acid sequence set forth in any one of SEQ ID NOs: 101-105, an LCDR2 amino acid sequence set forth in any one of SEQ ID NOs: 111-115, and/or an LCDR3 amino acid sequence set forth in any one of SEQ ID NOs: 121-125. In certain embodiments, the second binding component comprises an amino acid sequence comprising at least about 90%, 95%, 97%, 99% identity to, or is 100% identical to the amino acid sequence set forth in any one of SEQ ID NO: 3 and SEQ ID NO: 4. In certain embodiments, the second binding component comprises an amino acid sequence comprising at least about 90%, 95%, 97%, 99% identity to, or is 100% identical to the amino acid sequence set forth in SEQ ID NO: SEQ ID NO: 3 and SEQ ID NO: 4.

The composite binding molecule can bind a first target and a second target, wherein the first target comprises a B-cell lineage surface marker, and wherein the second target comprises a suppressive B-cell surface marker. In some embodiments, the composite binding molecule binds to CD19 positive (CD19+ or CD19$^{high}$) and CD38 positive (CD38+ or CD19$^{high}$) B-cells.

The composite binding molecule can be encoded for by a nucleic acid molecule. Disclosed herein are nucleic acids comprising a polynucleotide sequence encoding a composite binding molecule disclosed herein. In some embodiments, the polynucleotide sequence encoding the composite binding molecule is operatively coupled to a eukaryotic regulatory sequence.

A cell can comprise the nucleic acid encoding the composite binding molecules. In some embodiments, the cell comprises a prokaryotic cell. In certain embodiments, the prokaryotic cell is an *Escherichia coli* cell. In come embodiments, the cell comprises a eukaryotic cell. In certain embodiments, the eukaryotic cell is a Chines Hamster Ovary (CHO) cell, an NS0 murine myeloma cell, or a human PER.C6 cell.

Also disclosed herein are compositions comprising the composite binding molecule and a pharmaceutically acceptable diluent, carrier, or excipient. In some embodiments, the compositions are formulated for intravenous administration. In some embodiments, the compositions are formulated for subcutaneous administration.

The composite binding molecule disclosed herein can inhibit and/or reduce the number of immunosuppressive B cells that suppress an anti-tumor immune response. Thus, the composite binding molecules herein can be used in a method of treating a tumor or a cancer in an individual. In some embodiments, the cancer or the tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

In some embodiments, the cancer or the tumor is a solid-tissue cancer. In some embodiments, the cancer comprises breast cancer, prostate cancer, pancreatic cancer, lung cancer, kidney cancer, stomach cancer, esophageal cancer, skin cancer, colorectal cancer, or head and neck cancer. In some embodiments, the cancer is breast cancer. In some certain embodiments, the breast cancer is triple negative breast cancer. In some embodiments, the cancer is lung cancer. In certain embodiments, the lung cancer is non-small cell lung cancer. In some embodiments, the cancer is head and neck cancer. In certain embodiments, the head and neck cancer is head and neck squamous cell cancer. In some embodiments, the cancer is kidney cancer. In certain embodiments, the kidney cancer is renal cell carcinoma. In some embodiments, the cancer is brain cancer. In some embodiments, the brain cancer is glioblastoma multiforme. In some embodiments, the cancer is skin cancer. In certain embodiments, the skin cancer is melanoma.

The composite binding molecules herein can be used in a method of reducing tumor infiltrating B cells and/or immunosuppressive B cells that suppress an anti-tumor immune response against a tumor of an individual. The composite binding molecules herein can be used in a method of inhibiting the function of tumor infiltrating B cells and/or immunosuppressive B cells that suppress an anti-tumor immune response against a tumor of an individual. The composite binding molecule can be used in a method of reducing suppressive B cells in, adjacent to, or surrounding a tumor of an individual. In some embodiments, the tumor infiltrating B cells or the immunosuppressive B cells comprise CD19+, CD38+ B cells.

Further disclosed herein are methods of treating an individual afflicted with a cancer or a tumor comprising administering to the individual afflicted with the cancer or the tumor the composite binding molecule disclosed herein, thereby treating the cancer or tumor. In some embodiments, the cancer or tumor is a hematologic cancer. In some embodiments, the hematological cancer is a B cell malignancy. In certain embodiments, the B cell malignancy is B-cell Acute Lymphocytic Leukemia. In certain embodiments, the B cell malignancy is Chronic Lymphocytic Leukemia, Small Lymphocytic Lymphoma, Mantle Cell Lymphoma, or Non-Hodgkins Lymphomas (Diffuse Large B-cell Lymphoma, Follicular Lymphoma). In some embodiments, the hematological cancer is a plasma malignancy. In certain embodiments, the plasma malignancy is multiple myeloma. In some embodiments of any of the preceding embodiments, the hematological cancer expresses CD19 and CD38 (e.g. cells of the cancer express CD19 and CD38).

In some embodiments, the cancer or tumor is a solid-tissue cancer. In some embodiments, the cancer comprises breast cancer, prostate cancer, pancreatic cancer, lung cancer, kidney cancer, stomach cancer, esophageal cancer, skin cancer, colorectal cancer, or head and neck cancer. In some embodiments, the cancer is breast cancer. In some certain embodiments, the breast cancer is triple negative breast cancer. In some embodiments, the cancer is lung cancer. In certain embodiments, the lung cancer is non-small cell lung cancer. In some embodiments, the cancer is head and neck cancer. In certain embodiments, the head and neck cancer is head and neck squamous cell cancer. In some embodiments, the cancer is kidney cancer. In certain embodiments, the kidney cancer is renal cell carcinoma. In some embodiments, the cancer is brain cancer. In some embodiments, the brain cancer is glioblastoma multiforme. In some embodiments, the cancer is skin cancer. In certain embodiments, the skin cancer is melanoma.

Also disclosed is a method of reducing tumor infiltrating B cells in, adjacent to, or surrounding a tumor of an individual afflicted with a tumor or cancer comprising administering to the individual afflicted with the tumor or the cancer the composite binding molecule disclosed herein, thereby reducing tumor infiltrating B cells in the tumor. Also disclosed are methods of reducing immunosuppressive B cells in, adjacent to, or surrounding a tumor of an individual afflicted with a tumor or cancer comprising administering to the individual afflicted with the tumor or the cancer the composite binding molecule disclosed herein, thereby reducing immunosuppressive B cells in the tumor. In some embodiments, the tumor infiltrating B cells or the immunosuppressive B cells comprise CD19+, CD38+ B cells. In some embodiments, reducing tumor infiltrating B cells comprises reducing and/or blocking and/or preventing and/or inhibiting the recruitment of immunosuppressive B cells into a tumor environment or microenvironment. In some embodiments, reducing tumor infiltrating B cells comprises reducing and/or blocking and/or preventing and/or inhibiting cell-to-cell contact induced immunosuppression mediated by immunosuppressive B cells. In some embodiments, reducing tumor infiltrating B cells comprises reducing and/or blocking and/or preventing and/or inhibiting immunosuppressive B cell differentiation.

Disclosed herein are method of making the composite binding molecule disclosed herein, comprising incubating the cell disclosed herein in a cell culture medium under conditions sufficient to allow expression, assembly and secretion of the composite binding molecule into the cell culture medium. In some embodiments, the method comprised isolating and purifying the molecule from the cell culture medium.

The composite binding molecule disclosed herein can be used in treating a cancer or tumor. Thus, disclosed is a method of preparing a cancer treatment for an individual comprising admixing a composite binding molecule of the disclosure with a pharmaceutically acceptable diluent, carrier, or excipient.

EXAMPLES

The following examples are included for illustrative purposes only and are not intended to limit the scope of the invention.

Example 1: Cell Binding Properties of CD19 and CD38 Antibodies

Figure 12A:
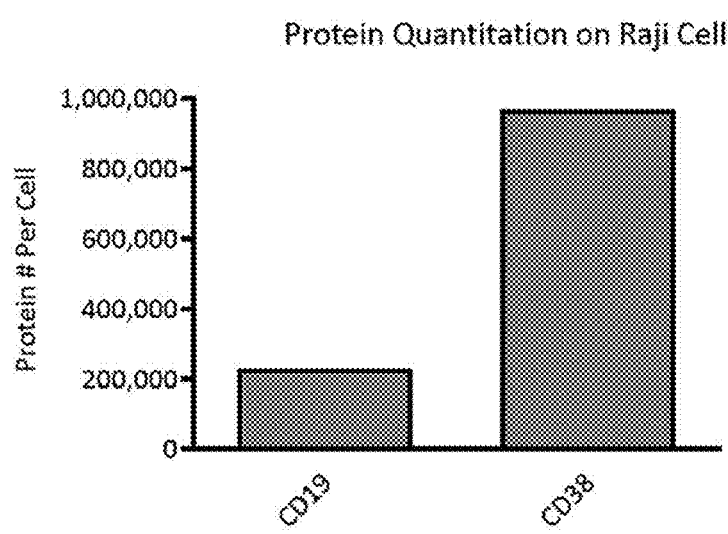
FIG. 12A to 12E show binding data of CD19 and CD38 antibodies.
Figure 12B:
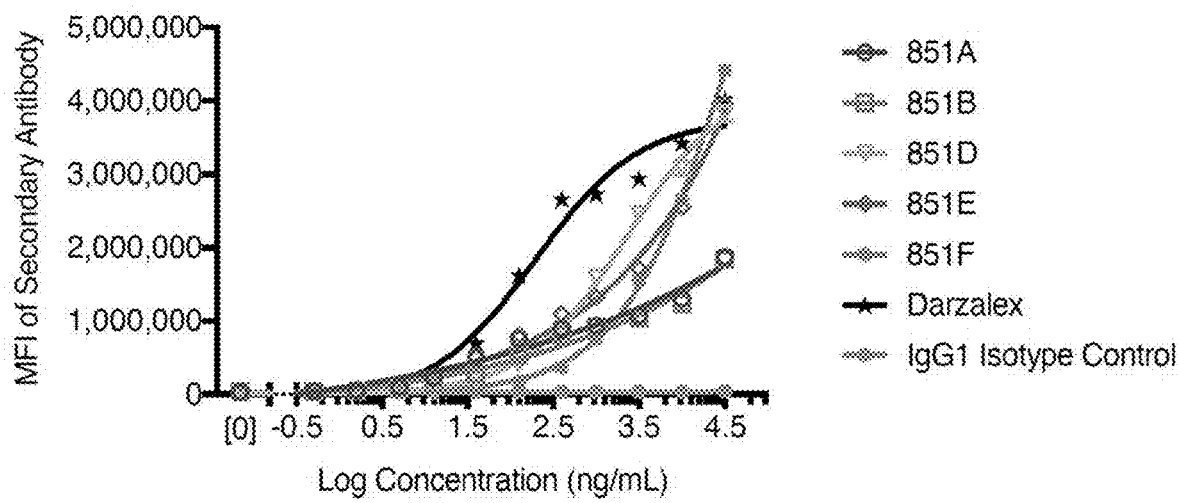
Figure 12C:
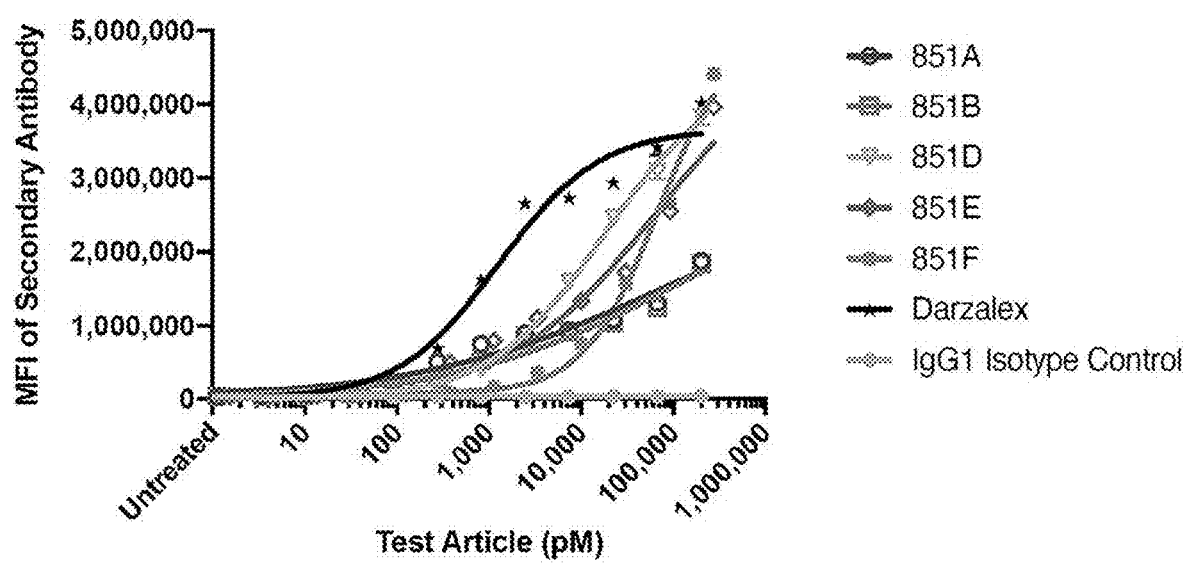
Figure 12D:
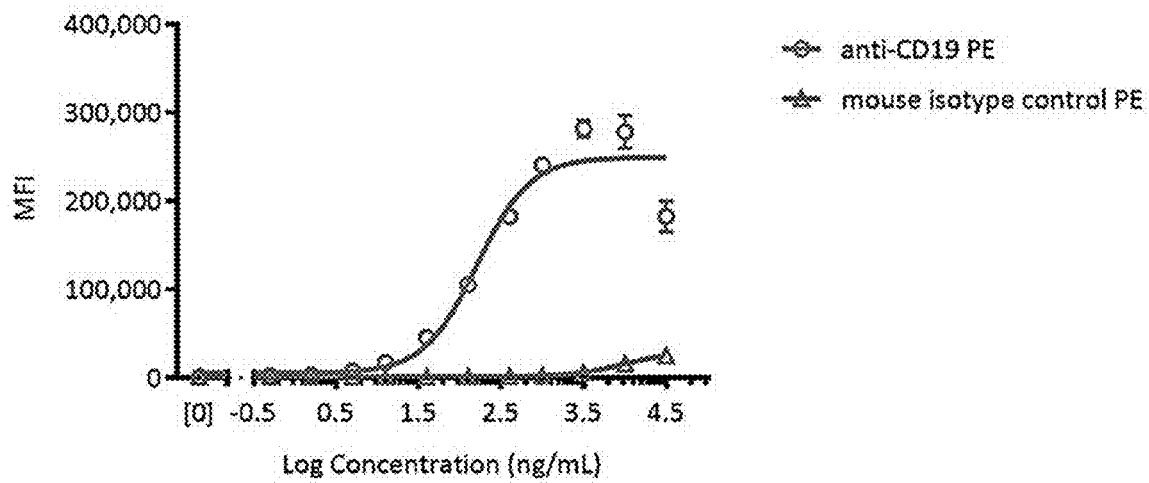
Figure 12E:
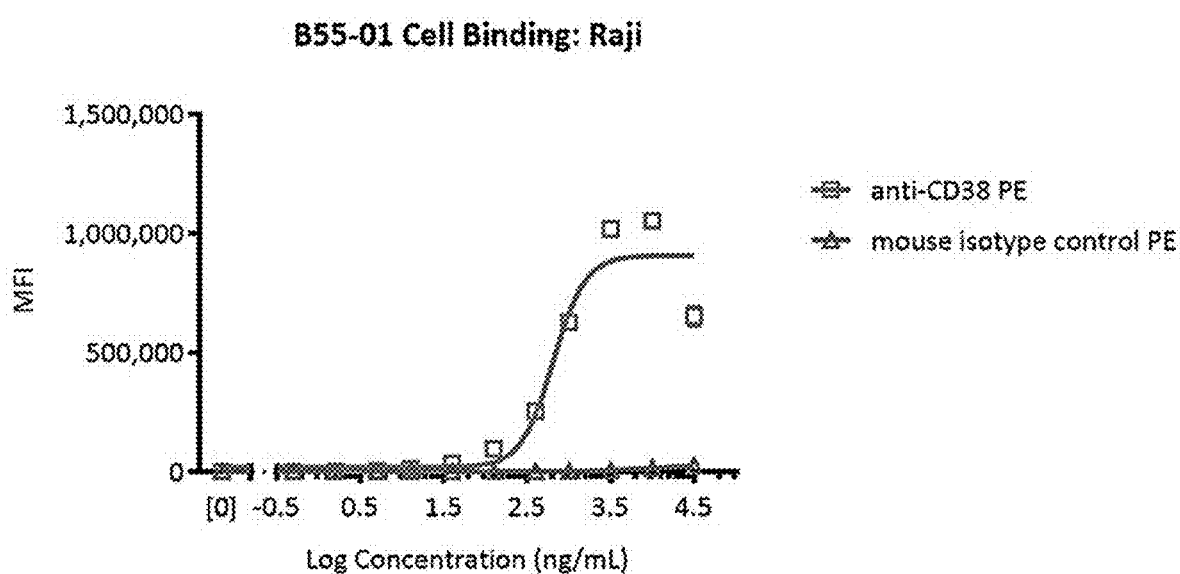
Figure 12F:
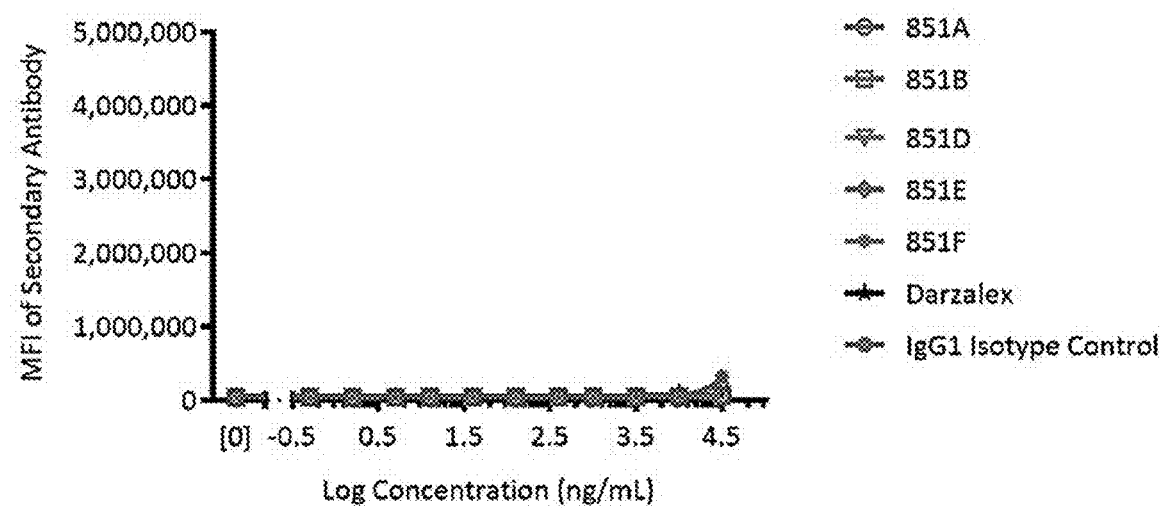
FIG. 12F shows binding profiles of cells that do not express CD19 and CD38.

Exemplifying the disclosure herein, composite binding molecule comprising a first binding component configured to bind a first target and a second binding component configured to bind a second target, wherein the first target comprises a B-cell lineage surface marker, and wherein the second target comprises a suppressive B-cell surface marker, were tested for binding to cells expressing CD19 and CD38. The binding properties of antibodies comprising CD19 and CD38 light and heavy chains to Raji cells expressing CD19 and CD38. FIG. 12A shows cell surface expression data of CD19 and CD38 in Raji cells. Raji cells expressing CD19 and CD38 were incubated with antibodies comprising CD19 and CD38 light and heavy chains. Cells were incubated with 30 ug/mL of antibodies across 11 differing concentrations to generate a binding profile for each sample. expression of CD19 and CD38 was validated using commercially available antibodies. Samples tested include: (A) matched CD19 heavy and light chains, the CD19 heavy chain comprising SEQ ID NO: 1 and CD19 light chain comprising SEQ ID NO: 2; (B) swapped CD19 heavy and CD38 light chains, the CD19 heavy chain comprising SEQ ID NO: 1 and CD38 light chain comprising SEQ ID NO: 4; (C) swapped CD38 heavy and CD19 light chains, the CD38 heavy chain comprising SEQ ID NO: 3 and CD19 light chain comprising SEQ ID NO: 2; (D) matched CD38 heavy and light chains, the CD38 heavy chain comprising SEQ ID NO: 3 and CD38 light chain comprising SEQ ID NO: 4; (E) a CD19 single chain variable fragment (scFv) comprising SEQ ID NO:1-2; (F) a CD38 single chain variable fragment (scFv) comprising SEQ ID NO:3-4; Darzalex® (CD38 control); Anti-CD19 PE (CD19 control); Anti-CD38 PE (CD38 control); and an IgG1 isotype control FIGS. 12B and 12C show binding profiles of samples A-F, Darzalex®, and the IgG1 isotype control. TABLE 1 and TABLE 2 shows $EC_{50}$ values and maximum mean fluorescence intensity (MFI) of samples A-F, Darzalex®, and the IgG1 isotype control. Each of samples A-F demonstrated binding to Raji cells expressing CD19 and CD38, wherein the binding profiles of samples A-F varied amongst the samples. FIGS. 12D and 12E show binding of control anti-CD19 (FIG. 11D) and anti-CD38 antibodies (FIG. 11E). FIG. 12F shows that the antibodies tested did not bind to CHO cells that do not express CD19 and CD38.

TABLE 1

| | Cell Binding | |
|---|---|---|
| Sample | EC50 (ng/mL) | Max MFI |
| A | ~6E+21 | 1878626 |
| B | ~38394212 | 1842964 |
| C | ND | ND |
| D | 2260 | 3827997 |
| E | ~1E+16 | 3957921 |
| F | 37889 | 4416606 |
| Darzalex ® | 195 | 4016941 |
| IgG1 isotype control | ~4622880 | 38691 |

TABLE 2

| | Cell Binding | | |
|---|---|---|---|
| Sample | EC50 (nM) | Max MFI | Adjusted* EC50 (nM) |
| A | NA | 1878626 | 78.79 |
| B | NA | 1842964 | 113.11 |
| C | ND | ND | ND |
| D | 17.39 | 3827997 | 17.39 |
| E | NA | 3957921 | 66.85 |
| F | NA | 4416606 | 67.40 |
| Darzalex ® | 1.27 | 4016941 | 1.27 |
| IgG1 isotype control | — | 38691 | — |

NA - The treatment did not produce a signal that plateaued. EC50 cannot be defined in the conventional manner
*The top asymptote is fixed at about the maximum response of Darzalex ®.

Example 2: Octet® Binding Data

The binding affinities of parental and bispecific antibodies were determined using bio-layer interferometry. Binding experiments were performed on Octet® Red96 at 25° C. using an assay Buffer consisting of 0.1% BSA, 1×PBS, 0.02% Tween®-20, 0.05% NaN3. The antibodies were loaded onto Anti-hIgG Fc Capture biosensors for 300 seconds. The ligand-loaded sensors were dipped into a series dilution (starting at 300 nM: two-fold series dilution for CD19 and three-fold series dilution for CD38) of the antigens for association (200 seconds for CD19 and 150 seconds for CD38) followed by dissociation (600 seconds for CD19 and 400 seconds for CD38). Kinetic constants were calculated using a monovalent (1:1) binding model.

Parental test articles included:
851A=anti-CD19 3C10
851B=anti-CD19 3C10 heavy chain & anti-CD38 003 light chain
851C=anti-CD38 003 heavy chain & anti-CD19 3C10 light chain
851D=anti-CD38 003
851E=anti-CD19 3C10 (scFv-Fc)2
851F=anti-CD38 003 (scFv-Fc)2

The two parental antibodies with anti-CD19 3C10 VH and VL (851A/851E) bound CD19 with a similar KD. Substituting the anti-CD19 3C10 VL with the anti-CD38 VL (851B) resulted in a reduction of binding to CD19 of about 5-fold. The parental antibodies with anti-CD38 003 VH and VL (851D/851F) did not bind to CD19, as expected.

Table 3 shows binding data. The two parental antibodies with anti-CD38 003 VH and VL (851D/851F) bound CD38 with a similar KD. Substituting the anti-CD38 003 VL with the anti-CD19 VL (851C) resulted in a large reduction of binding to CD38. The parental antibodies with anti-CD19 VH and VL (851A/851E) did not bind to CD38, as expected; 851B also did not bind to CD38. This data shows that only the anti-CD38 003 VL can function as a common light chain for the anti-CD19 3C10 VH.

TABLE 3

| | KD (nM) | |
|---|---|---|
| Sample | CD19 | CD38 |
| 851A | 1.53 | NB |
| 851B | 7.07 | NB |
| 851C | NB | 285 |
| 851D | NB | 0.98 |
| 851E | 1.21 | NB |
| 851F | NB | 2.22 |

NB = no binding

Bispecific antibody (format) test articles included:

BS1=1:1:2 ratio 003HC:3C10HC:003LC (common light chain)

BS1b=2:1:2 ratio 003HC:3C10HC:003LC (common light chain)

BS2=1:1:1 ratio 003Knob:3C10scFvHole:003LC (Fab-Fc: scFv-Fc bispecific IgG1)

BS2b=4:1:4 ratio 003Knob:3C10scFvHole:003LC (Fab-Fc: scFv-Fc bispecific IgG1)

BS3=1:1:1 ratio 3C10scFv-003Fab-FcKnob:FcHole: 003LC) (scFv-Fab-Fc: Fc bispecific IgG1)

BS4=1:1:1 ratio 003Fab-FcKnob-3C10scFv:FcHole (Fab-Fc-scFv: Fc bispecific IgG1)

BS4b=4:1:4 ratio 003Fab-FcKnob-3C10scFv:FcHole (Fab-Fc-scFv: Fc bispecific IgG1)

CM1=1:1:2 ratio 3C10Hole:VZVKnob:003LC anti-CD19 control antibody

CM1b=1:3:3 ratio 3C10Hole:VZVKnob:003LC

CM2=1:1:2 ratio 003Knob:VZVHole:003LC anti-CD38 control antibody

CM2b=3:1:3 ratio 003Knob:VZVHole:003LC

Table 4 shows binding data for bispecific test articles in a single antigen format. Bispecific antibodies BS1/BS2/BS4 bound to both target antigens with a KD within 4-fold of parental antibodies (shown with gray shading). BS3 bound only to CD19 but not CD38 suggesting that either the anti-CD38 Fab binding site was blocked by the anti-CD19 scFv N-terminal fusion or the anti-CD38 requires a free VH N-terminus for binding. One-arm control antibodies (CM1, CM2) bound only to their intended target antigen.

TABLE 4

| Sample | KD (nM) CD19 | KD (nM) CD38 |
|---|---|---|
| BS1 | 13.8 | 1.32 |
| BS1b | 13.0 | 1.23 |
| BS2 | 1.53 | 1.33 |
| BS2b | 1.58 | 1.12 |
| BS3 | 3.32 | NB |
| BS4 | 1.31 | 1.20 |
| BS4b | 4.78 | 1.21 |
| CM1 | 18.2 | NB |
| CM1b | 15.9 | 2210 |
| CM2 | NB | 1.67 |
| CM2b | 21300 | 0.59 |

NB = no binding

For a two-antigen format, the antibodies were loaded onto Anti-hIgG Fc Capture biosensors for 300 seconds. The ligand-loaded sensors were saturated with 500 nM of first antigen for 500 seconds followed by 300 nM of second antigen for 240 seconds. Kinetic constants were calculated using a monovalent (1:1) binding model. Table 5 shows bispecific antibodies BS1/BS2/BS4 could simultaneously bind to both target antigens with a ka (1/Ms) within 2-fold of parental antibodies (851B, 851D, and 851E). As with the one-antigen format, BS3 bound only to CD19 but not CD38.

TABLE 5

| Sample | KD (nM) Antigen 1 | KD (nM) Antigen 2 | Second Antigen Ka (1/Ms)E + 04 |
|---|---|---|---|
| 851B | — | CD19 | 4.24 |
| 851D | — | CD38 | 43.1 |
| 851E | — | CD19 | 4.89 |
| BS1 | CD19 | CD38 | 27.0 |
| BS1 | Buffer | CD38 | 40.9 |
| BS1b | CD19 | CD38 | 26.3 |
| BS1b | Buffer | CD38 | 31.6 |
| BS2 | CD19 | CD38 | 25.4 |
| BS2 | Buffer | CD38 | 44.7 |
| BS2b | CD19 | CD38 | 22 |
| BS2b | Buffer | CD38 | 32.8 |
| BS3 | CD19 | CD38 | NB |
| BS3 | Buffer | CD38 | NB |
| BS4 | CD19 | CD38 | 37.2 |
| BS4 | Buffer | CD38 | 44.5 |
| BS4b | CD19 | CD38 | 26.7 |
| BS4b | Buffer | CD38 | 39.0 |
| CM1 | CD19 | CD38 | NB |
| CM1 | Buffer | CD38 | NB |
| CM2 | CD19 | CD38 | 30.0 |
| CM2 | Buffer | CD38 | 29.4 |
| BS1 | CD38 | CD19 | 4.44 |
| BS1 | Buffer | CD19 | 5.34 |
| BS1b | CD38 | CD19 | 6.87 |
| BS1b | Buffer | CD19 | 8.98 |
| BS2 | CD38 | CD19 | 5.74 |
| BS2 | Buffer | CD19 | 5.31 |
| BS2b | CD38 | CD19 | 6.66 |
| BS2b | Buffer | CD19 | 8.20 |
| BS3 | CD38 | CD19 | 8.84 |
| BS3 | Buffer | CD19 | 8.93 |
| BS4 | CD38 | CD19 | 2.65 |
| BS4 | Buffer | CD19 | 4.55 |
| BS4b | CD38 | CD19 | 3.29 |
| BS4b | Buffer | CD19 | 4.64 |
| CM1 | CD38 | CD19 | 5.07 |
| CM1 | Buffer | CD19 | 4.73 |
| CM2 | CD38 | CD19 | NB |
| CM2 | Buffer | CD19 | NB |

NB = no binding

Variants were further tested for the ability to bind CD19 and/or CD38. Binding experiments were performed on Octet® Red at 25° C. The antibodies were loaded onto anti-hIgG Fc Capture (AHC) biosensors for 300 seconds. The ligand-loaded sensors were dipped into a two-fold series dilution (starting at 300 nM) of the antigens (CD19 and CD38) for 240 seconds of CD19 and 150 seconds of CD38 for association followed by dissociation for 600 seconds of CD19 and 130 seconds of CD38. Kinetic constants were calculated using a monovalent (1:1) binding model. TABLE 6 shows binding of anti-CD38 CDRH2 variants. TABLE 7 shows binding of the CD38 light chain W32H variant. TABLE 8 shows binding of CD19 heavy chain framework mutant A84S A108L.

TABLE 6

Bispecific BS1 anti-CD38 arm CDR-H2 variants
("RVIPFLGIAN" disclosed as SEQ ID NO: 85)

| | SEQUENCE | | | | | | | | | | CD38 Binding KD (nM) |
|---|---|---|---|---|---|---|---|---|---|---|---|
| BS1 | R | V | I | P | F | L | G | I | A | N | 1.2 |
| BS1M-1 | • | • | • | • | • | • | • | T | • | • | 13.2 |
| BS1M-3 | • | • | • | • | H | • | • | • | • | • | 6.9 |
| BS1M-4 | • | • | • | • | H | • | • | T | • | • | 94.4 |
| BS1M-6 | • | • | • | • | Q | • | • | • | • | • | 4.4 |
| BS1M-7 | • | • | • | • | Q | • | • | T | • | • | 60.5 |
| BS1M-2 | • | • | T | • | • | • | • | T | • | • | No binding |
| BS1M-5 | • | • | T | • | H | • | • | T | • | • | No binding |
| BS1M-8 | • | • | • | • | H | Q | • | T | • | • | No binding |
| BS1M-9 | • | • | • | • | Q | Q | • | T | • | • | No binding |

TABLE 7

Bispecific BS1 common light chain variant

| | CD38 Binding KD (nM) | CD19 Binding KD (nM) |
|---|---|---|
| BSM-10 (W32H) | 77.3 | 39.4 |
| BS1 | 1.2 | 13 |

TABLE 8

Bispecific BS1 anti-CD19 arm framework variant

| | CD19 Binding KD (nM) |
|---|---|
| BSM-14 (A84S A108L) | 9.5 |
| BS1 | 13 |

Example 3: Cell Binding Studies

Cell Binding Studies Protocol: Five cell lines (HEK293-CD19, HEK293-CD38, HEK293-CD19/CD38, Daudi, and REH) were incubated with test articles at 133 nM followed by a 3-fold dilution series (7 points total), in addition to a no treatment control, in triplicate. The HEK293 cell lines were transiently transfected.

A study was performed to evaluate the cell surface expression of CD19 and CD38 on Daudi, Raji and REH cell lines. Cells were stained, in triplicate, with commercially available antibody conjugated to PE, washed, and acquired via flow cytometry. To quantify the molecule expression on the surface of the cells, a Quantum Simply Cellular antimouse IgG kit from Bangs Laboratories (Catalog #815-A) was used to generate a standard curve for interpolating MFI to a molecule number per cell value (Table 9).

TABLE 9

| Cell Line | Number of Molecules | |
|---|---|---|
| | CD19 | CD38 |
| Daudi | 200,000 | 1,000,000 |
| Raji | 200,000 | 1,000,000 |
| REH | 50,000 | 300,000 |

Figure 13A:
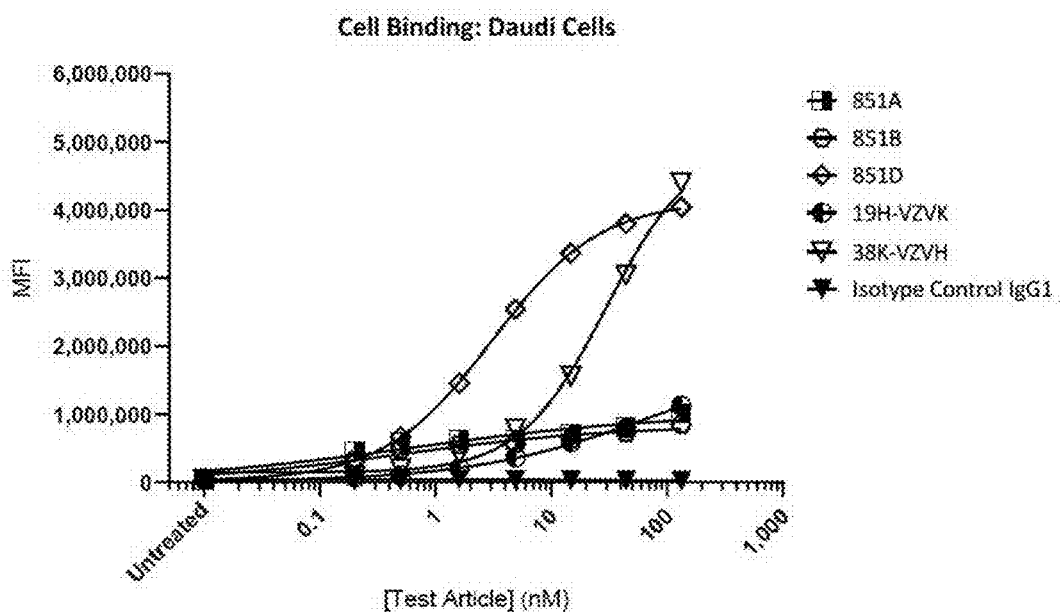
FIG. 13A to 13B shows binding data of antibodies to Daudi cells.

FIG. 13A shows binding to Daudi cells of the parental antibodies (851A, 851B, 851D) and the two control bispecific antibodies (each with one arm against CD19 or CD38 and the other arm against varicella zoster virus). Given that the Daudi cells have ~1 million copies of CD38 on their surface but only ~200,000 copies of CD19, FIG. 13A shows efficient binding of anti-CD38 851D and 38K-VZVH but only moderate binding of the anti-CD19 851A, 851B, 19H-VZVK. Note that 851D with two CD38 binding Fabs binds about 5-fold better than 38K-VZVH, which has only one binding Fab for CD38.

Figure 13B:
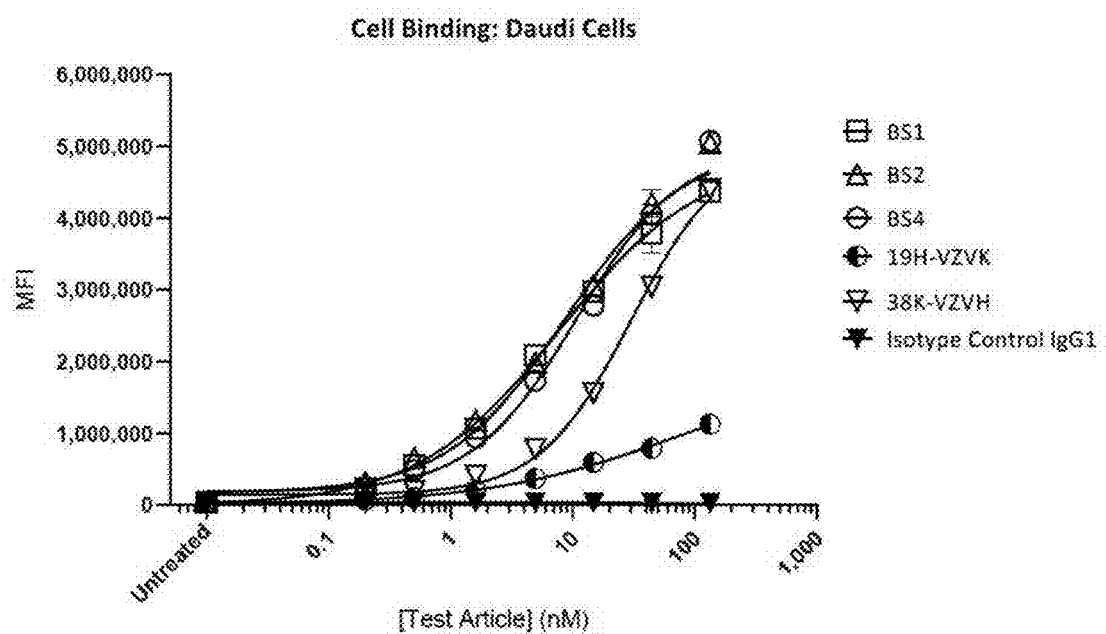

FIG. 13B shows binding to Daudi cells of bispecific antibodies BS1, BS2 and BS4. The avidity of the bispecific antibodies, binding to both CD38 and CD19, is apparent by comparing their binding to the 38K-VZVH, which binds only to CD38.

Figure 14A:
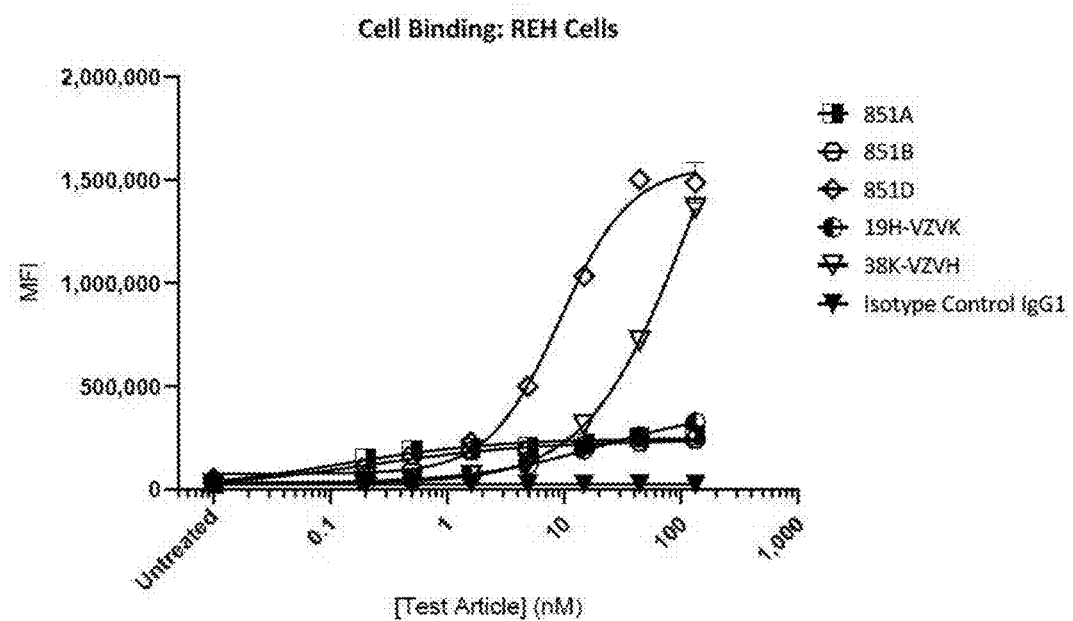
FIG. 14A to 14B shows binding data of antibodies to REH cells.

FIG. 14A shows binding to REH cells of the parental antibodies (851A, 851B, 851D) and the two control bispecific antibodies (each with one arm against CD19 or CD38 and the other arm against varicella zoster virus). Given that the REH cells have ~300,000 copies of CD38 on their surface but only 50,000 copies of CD19, FIG. 14A shows efficient binding of anti-CD38 851D and 38K-VZVH but only moderate binding of the anti-CD19 851A, 851B, 19H-VZVK. The magnitude of MFI is significantly less compared to Daudi cells (FIGS. 2A, 2B) due to the lower expression level of both CD38 and CD19 on REH cells. Note that 851D with two CD38 binding Fabs binds about 5-fold better than 38K-VZVH, which has only one binding Fab for CD38.

Figure 14B:
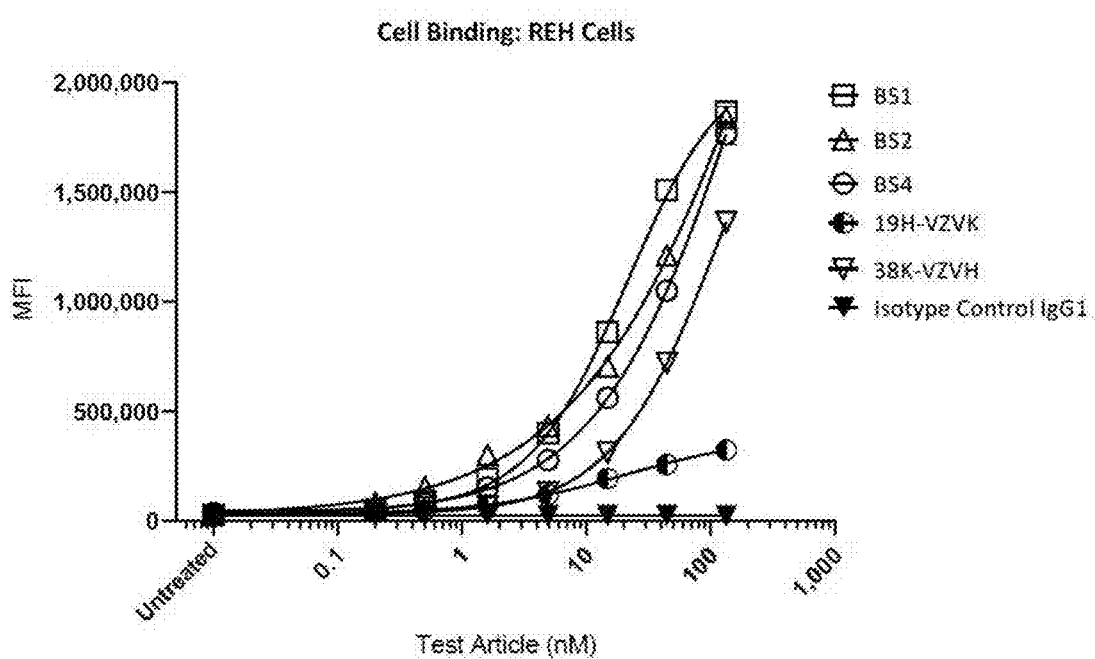

FIG. 14B shows binding to REH cells of bispecific antibodies BS1, BS2 and BS4. The avidity of the bispecific antibodies, binding to both CD38 and CD19, is apparent by comparing their binding to the 38K-VZVH, which binds only to CD38.

Figure 15A:
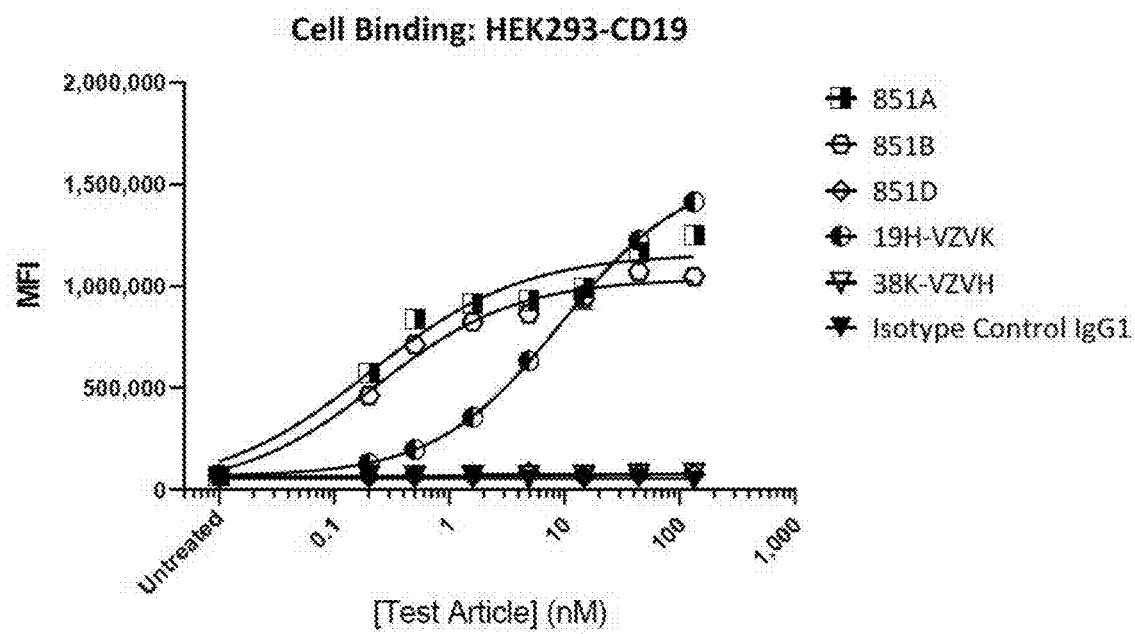
FIG. 15A to 15B shows binding data of antibodies to CD19 transfected HEK293 cells.

FIG. 15A shows binding to CD19-transfected HEK293 cells of the parental antibodies (851A, 851B, 851D) and two control bispecific antibodies (38K-VZVH, 19H-VZVK). As expected, the two anti-CD38 antibodies do not bind to these cells. Note that 851A and 851B, each with two CD19 binding Fabs, bind significantly better than 19H-VZVK, which has only one binding Fab for CD19.

Figure 15B:
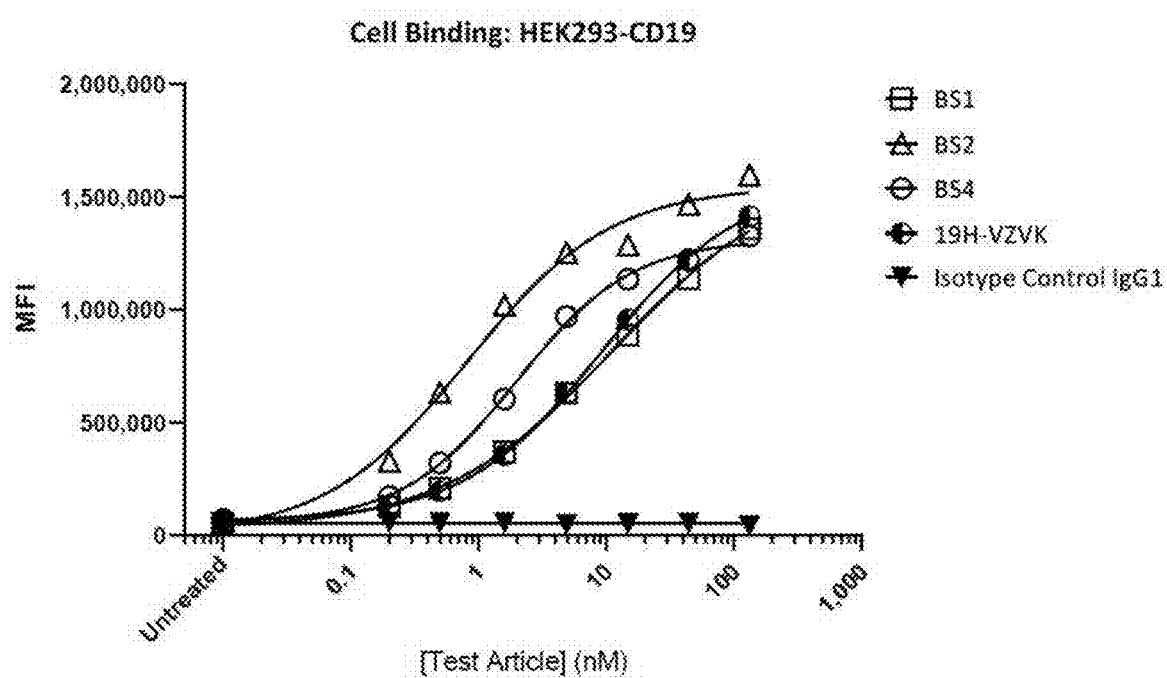

FIG. 15B shows binding to CD19-transfected HEK293 cells of bispecific antibodies BS1, BS2 and BS4. BS2 and BS$ bind slightly better than BS1; BS2 and BS4 bind CD19 about 10-fold better than BS1 since BS1 has the anti-CD38 light chain (see Table Octet® data).

Figure 16A:
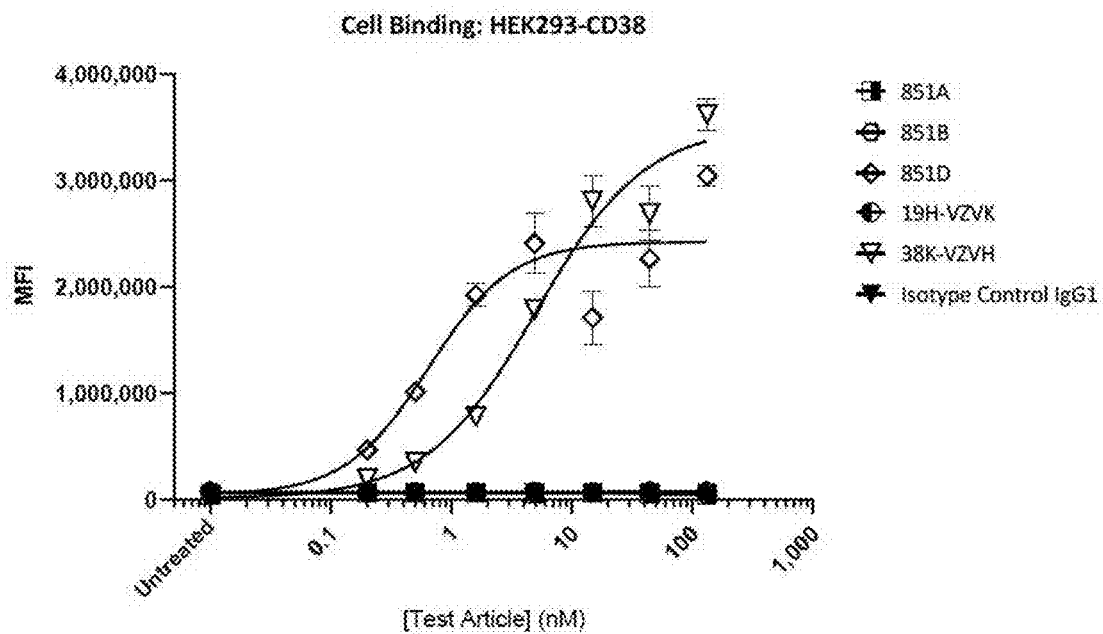
FIG. 16A to 16B shows binding data of antibodies to CD38 transfected HEK293 cells.

FIG. 16A shows binding to CD38-transfected HEK293 cells of the parental antibodies (851A, 851B, 851D) and two control bispecific antibodies (38K-VZVH, 19H-VZVK). As expected, the three anti-CD19 antibodies do not bind to these cells. Note that 851D, with two CD38 binding Fabs, binds better than 38K-VZVH, which has only one binding Fab for CD38.

Figure 16B:
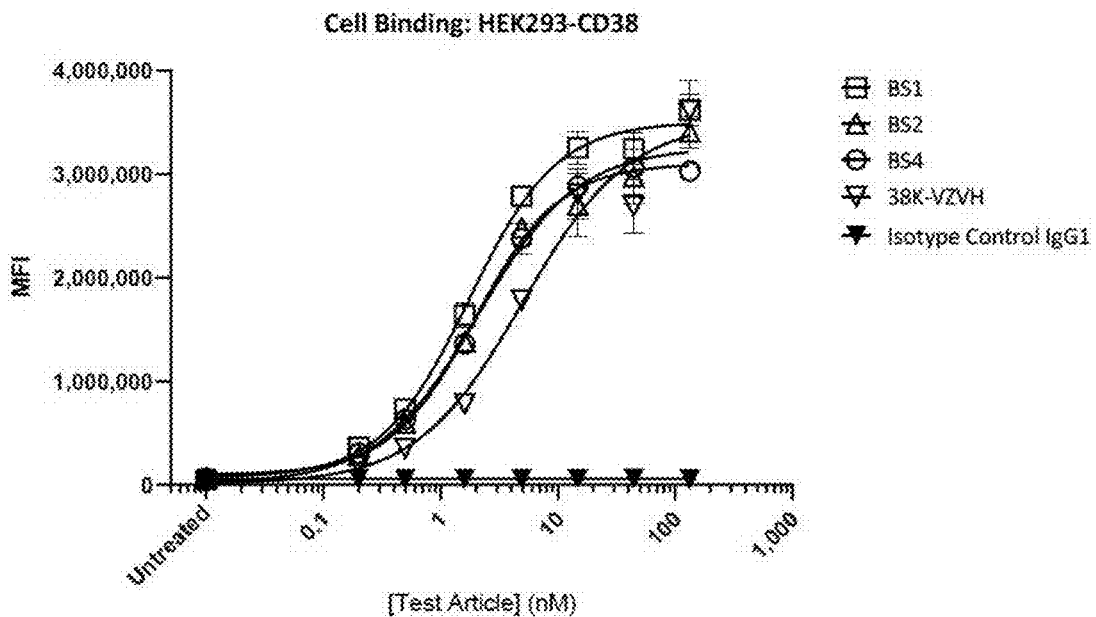

FIG. 16B shows binding to CD38-transfected HEK293 cells of bispecific antibodies BS1, BS2 and BS4.

Cell Binding Studies Protocol—Non-Specific Background Binding: A study was performed to evaluate the binding of three parental monoclonal antibodies (anti-CD19 clones 851A and 851B and anti-CD38 clone 851D), a human IgG1 isotype control, and daratumumab to CHO-S and Expi293T cell lines. The two cell lines were stained with a viability dye, then incubated with test articles at a top concentration of 1,250 nM followed by a 5-fold dilution series (4 points total), in addition to a no treatment control, as well as a no treatment, no secondary control, in triplicate.

Figure 17A:
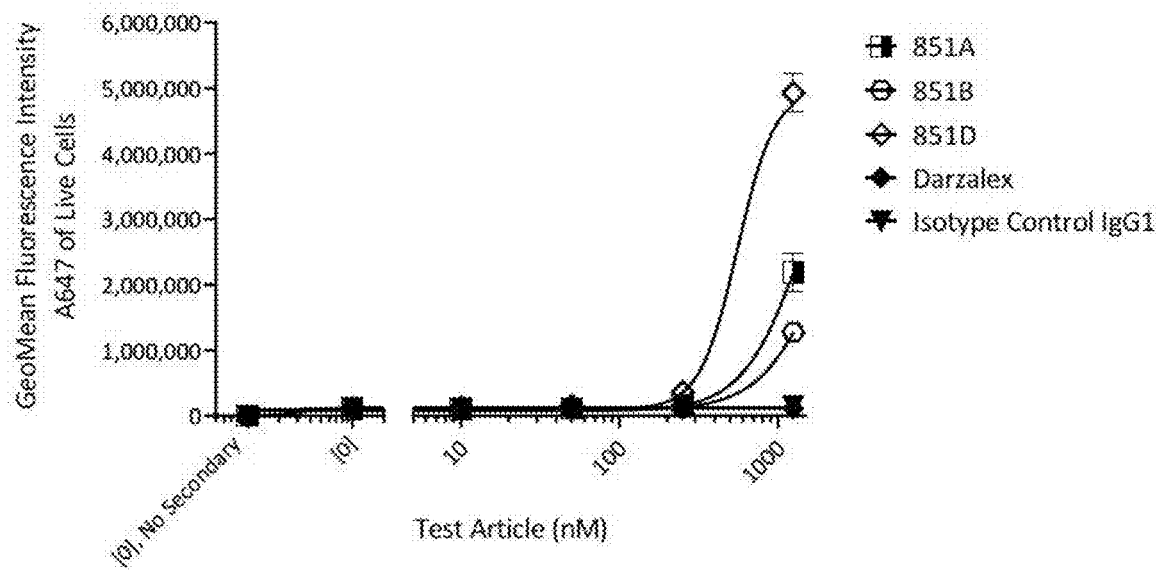
FIG. 17A to 17B shows binding data of antibodies to non-transfected CHO cells.

FIG. 17A shows binding to non-transfected CHO-S cells of the parental antibodies (851A, 851B, 851D). Non-specific binding was seen beginning at 250 nM for all three parental antibodies and was more pronounced for anti-CD38 851D.

Figure 17B:
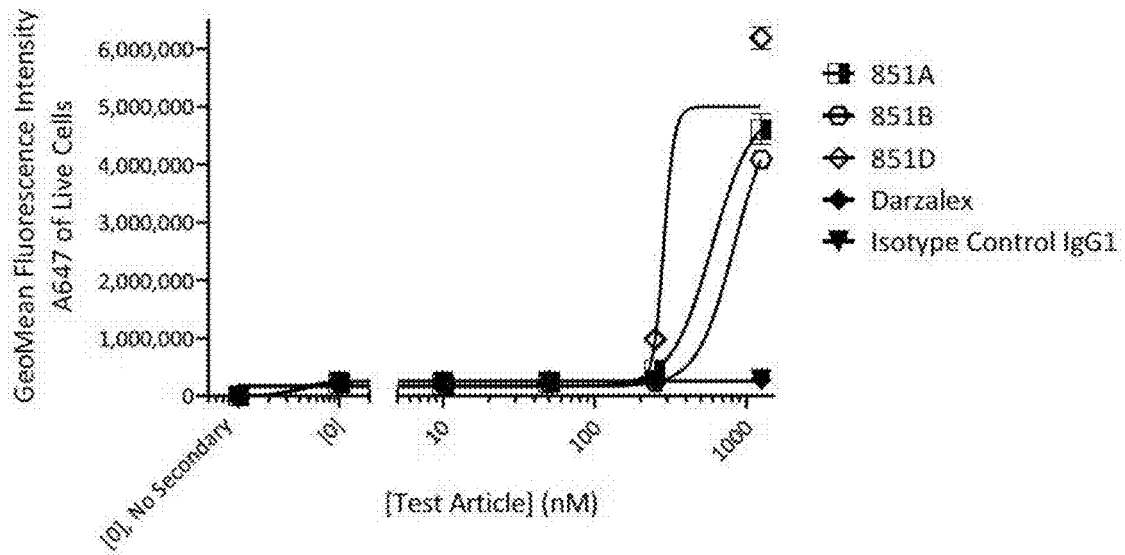

FIG. 17B shows binding to non-transfected Expi293T cells of the parental antibodies (851A, 851B, 851D). Non-specific binding was seen beginning at 250 nM for all three parental antibodies and was more pronounced for anti-CD38 851D.

Example 4: Direct and Cross-Linked Apoptosis

For assessment of direct apoptosis, cells were treated with test articles and incubated for 48 hours at 37° C./5% CO2. For assessment of cross-linking induced apoptosis, cells were incubated with test articles on ice for 30 minutes prior to the addition of rabbit anti-human Fc gamma specific F(ab')2 at 5 µg/mL. Cells were then incubated for 48 hours at 37 C/5% CO2. After incubation, cells were washed and stained with Annexin V, then resuspended in Annexin V buffer containing a viability dye (propidium iodide; PI) prior to flow cytometry acquisition. Early apoptotic cells were defined as Annexin V+/PI− single cells, while late apoptotic/necrotic cells were defined as Annexin V+/PI+ single cells. The sum of Annexin V+/PI− and Annexin V+/PI− were defined as total apoptotic/necrotic cells. The percentages of Annexin V+/PI− cells or Annexin V+/PI+ were plotted to compare the various apoptosis conditions.

For direct apoptosis assessment, test articles were each tested at a final top concentration of 33 nM, followed by a 7-point five-fold dilution series, in addition to an untreated control, in triplicate. For cross-linking induced apoptosis, individual test articles (BS1, BS2, BS4, 851A, 851B, and 851D) and combinations of test articles (851A and 851D; 851B and 851D; and 38K-VZVH and 19H-VZVK), in addition to daratumumab and IgG1 isotype control, were each tested at a final top concentration of 33 nM, followed by a 7-point five-fold dilution series, in addition to an untreated control, in triplicate. As a positive control for Annexin V staining, cells were treated with 5 mM staurosporine.

Figure 18A:
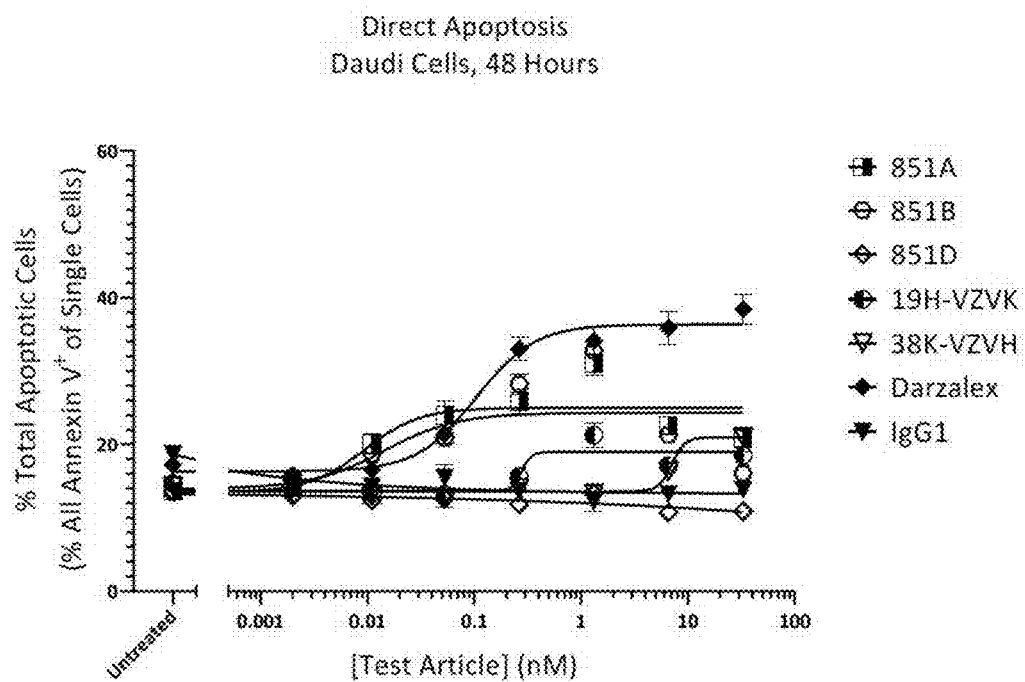
FIG. 18A to 18B shows data for direct apoptosis on Daudi cells for antibody test articles.

FIG. 18A shows direct apoptosis on Daudi cells for the parental antibodies (851A, 851B, 851D), two control bispecific antibodies (38K-VZVH, 19H-VZVK), daratumumab and IgG1 isotype control. Daratumumab exhibited the highest level of apoptosis. Both anti-CD19 parents (851A, 851B) exhibited a lower level of apoptosis compared to daratumumab. The two bispecific controls and the anti-CD38 parental antibody 851D did not show appreciable direct apoptosis.

Figure 18B:
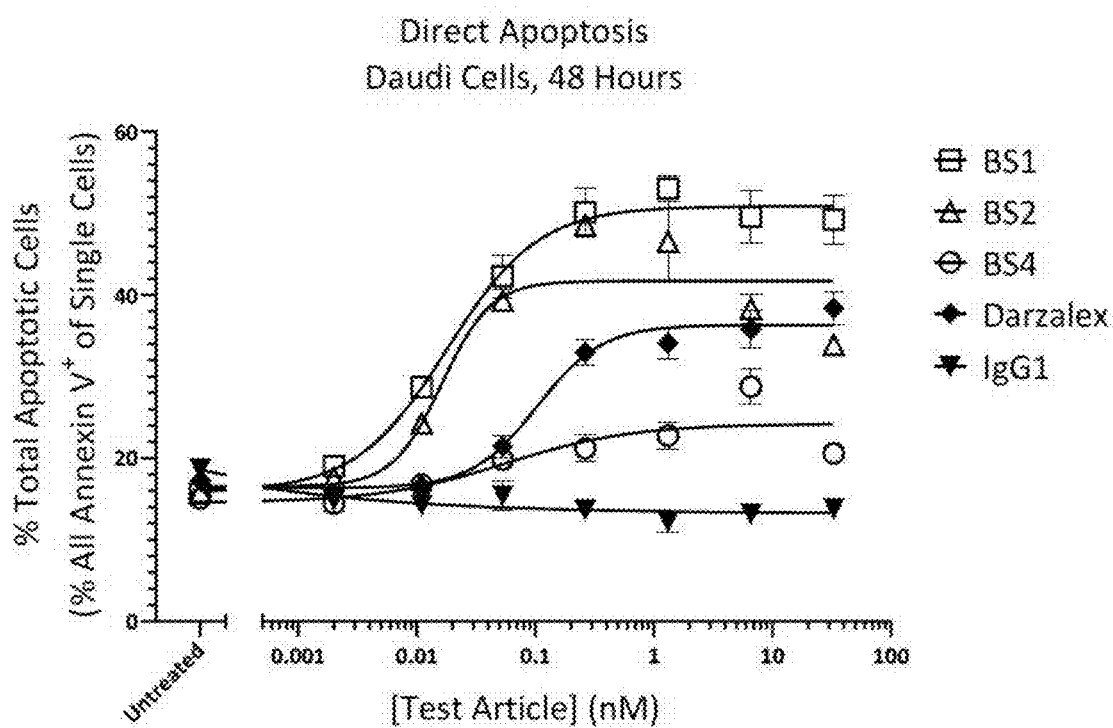

FIG. 18B shows direct apoptosis on Daudi cells for bispecific antibodies BS1, BS2, BS4, daratumumab and IgG1 isotype control. BS1 and BS2 formats showed a significantly higher level of direct apoptosis compared to daratumumab. Bispecific format BS4 showed a level of direct apoptosis comparable to the parental anti-CD19 851A/851B antibodies (compare FIG. 12A); this may be due to the BS4 format not being able to bring the CD19 and CD38 into close proximity in order to initiate apoptosis.

Figure 19A:
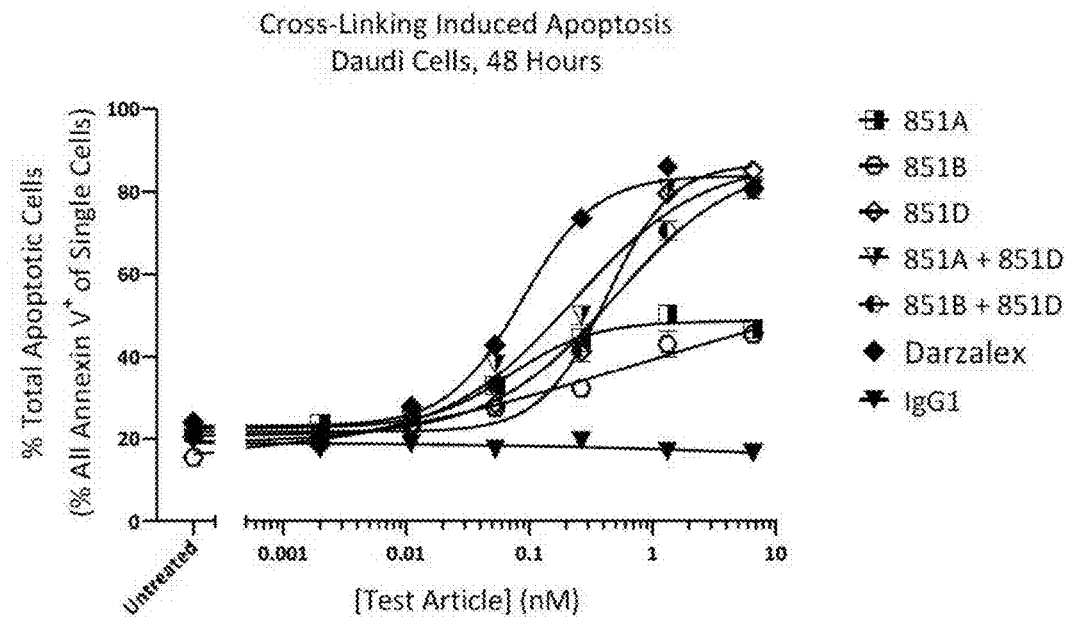
FIG. 19A to 19B shows data for cross-linking induced apoptosis on Daudi cells for antibody test articles.

FIG. 19A shows cross-linking induced apoptosis on Daudi cells for the parental antibodies (851A, 851B, 851D), two combinations of parental antibodies (851A+851D; 851B+851D), daratumumab and IgG1 isotype control. Cross-linking increased the level of daratumumab-driven apoptosis (compare FIGS. 12A and 7A). Cross-linking significantly increased the level of apoptosis for anti-CD38 851D, which showed no direct apoptosis (compare FIGS. 12A and 7A). The increase in level of apoptosis when cross-linking the anti-CD19 parent antibodies 851A and 851B was less than for CD38 antibodies, possibly due to the lower level of CD19, compared to CD38, on Daudi cells (see Table 9). Cross-linking combinations of anti-CD19 851A or 851B with anti-CD38 851D did not increase the level of apoptosis compared to 851D alone.

Figure 19B:
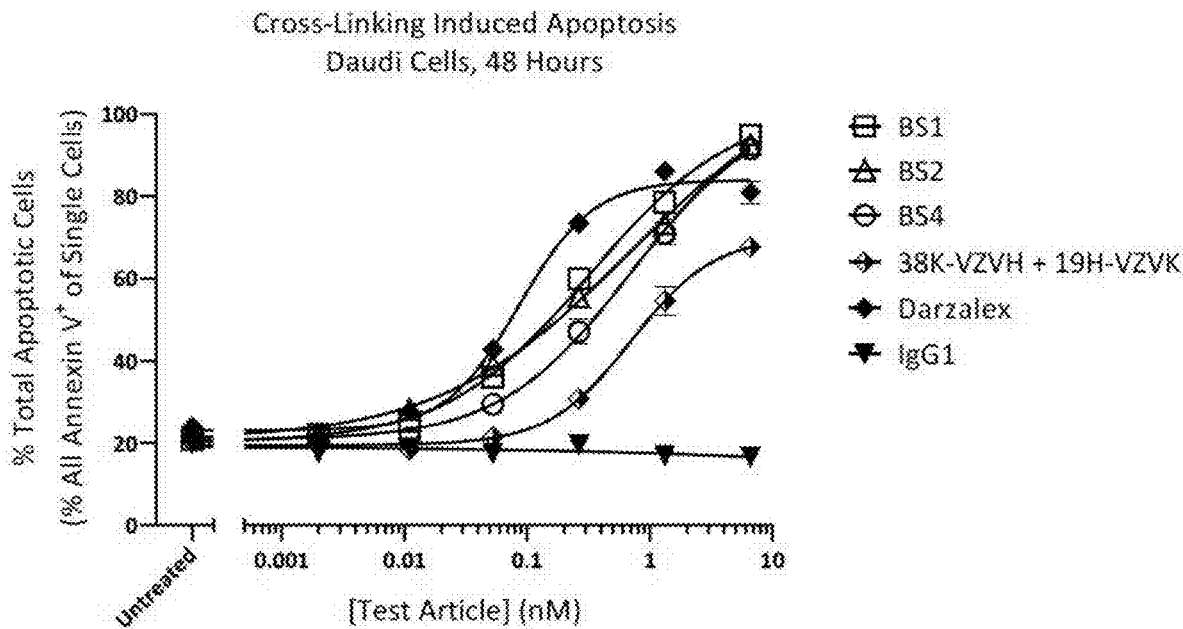

FIG. 19B shows cross-linking induced apoptosis on Daudi cells for bispecific antibodies BS1, BS2, BS4, (38K-VZVH+19H-VZVK), daratumumab and IgG1 isotype control. When cross-linked, BS1 and BS2 formats showed a level of apoptosis comparable to daratumumab. Notably, bispecific format BS4 showed a level of cross-linking induced apoptosis comparable to BS1, BS2 and daratumumab; without cross-linking, BS4 showed no apoptosis (see FIG. 6B). The combination of the two control antibodies, 38K-VZVH and 19H-VZVK, exhibited significant apoptosis but less than any of the bispecific formats, showing that including the anti-CD19 and anti-CD38 binding sites in a single antibody is more advantageous than in independent antibodies.

Example 5: Cytotoxicity

Daudi target cells were treated with a dose response of test articles and incubated for 15 minutes at 37 C/5% CO2. Test articles were tested at a final top concentration of 133 nM, followed by a 7-point five-fold dilution series, in addition to 0 nM control. Daratumumab and IgG1 isotype control were used as a positive and negative control.

Pre-treated target cells were co-cultured with human PBMCs from n=3 donors (E:T 25:1). PBMCs had been "primed" overnight with 100 U/mL of IL-2. PBMCs were ViaFluor 405-labeled. Samples were incubated for 4 hours at 37 C/5% CO2 prior to flow cytometry analysis for cytotoxicity. For cytotoxicity analysis, cells were stained with Propidium Iodide (P.I.) and analyzed by high throughput flow cytometry. The percentage of P.I.+ cells within the VF405-population was analyzed as a measure of target cell cytotoxicity.

Figure 20A:
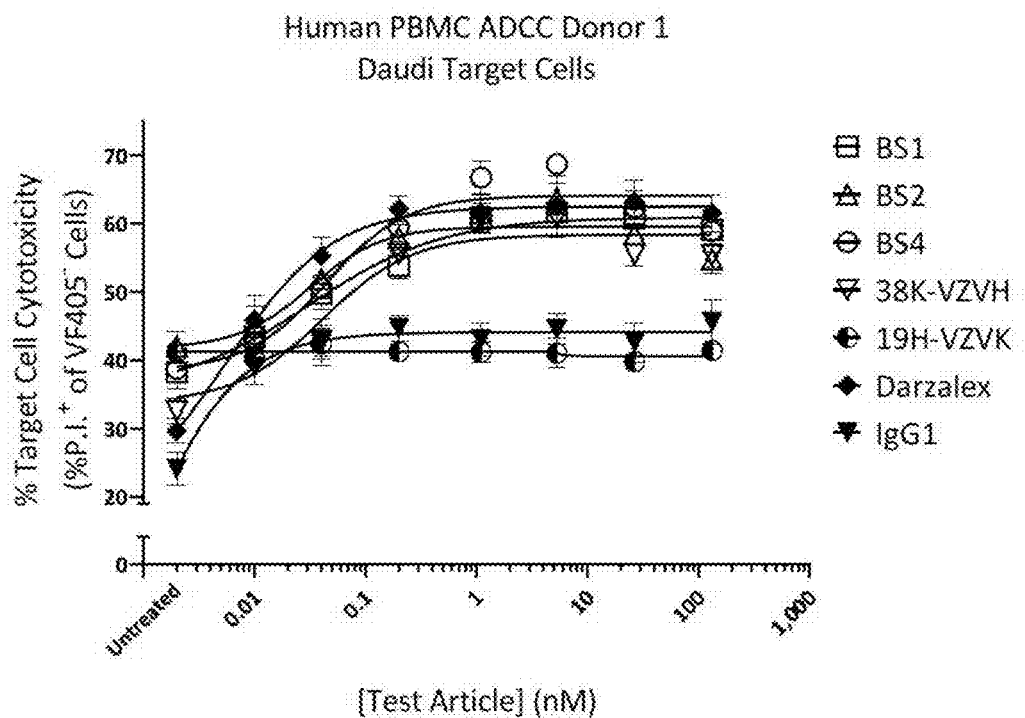
FIG. 20A to 20C shows ADCC data for three donors across antibody test articles.
Figure 20B:
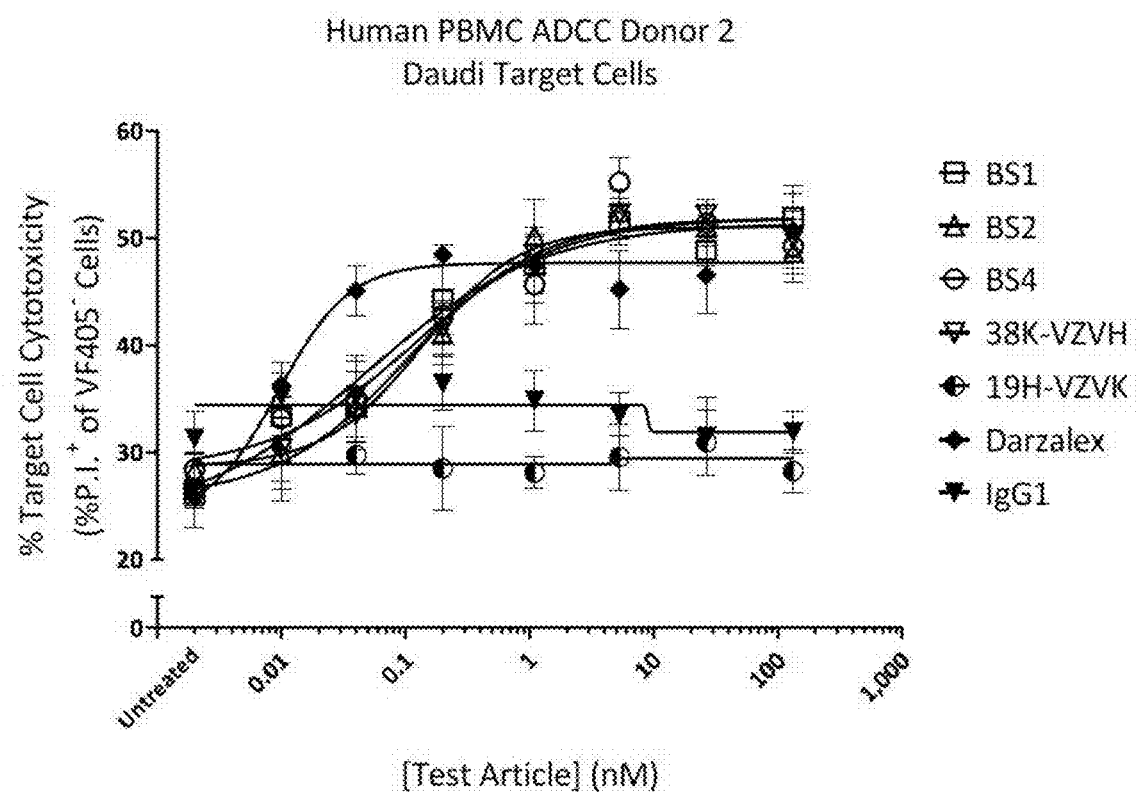
Figure 20C:
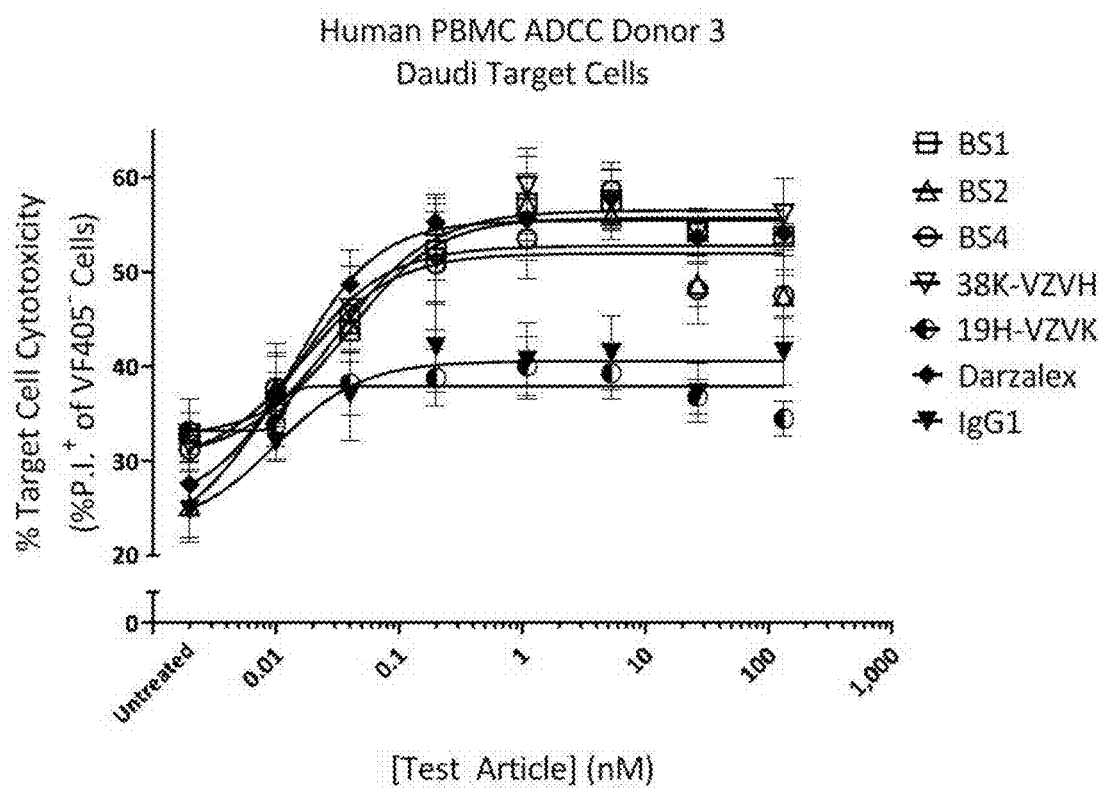

FIGS. 20A, 20B, and 20C show Antibody-Dependent Cellular Cytotoxicity (ADCC) for three donors. For all three donors, the results were similar. The three bispecific formats—BS1, BS2, BS4—and daratumumab exhibited similar levels of ADCC. The anti-CD19 bispecific control 19H-VZVK did not induce ADCC and was equivalent to the IgG1 control antibody, possibly due to low levels of CD19 on the target Daudi cells (see Table 9). In contrast, the anti-CD38 bispecific control 38K-VZVH exhibited ADCC equivalent to the bispecifics and daratumumab, likely due to the much higher level of CD38 on the Daudi cells compared to CD19.

Figure 21A:
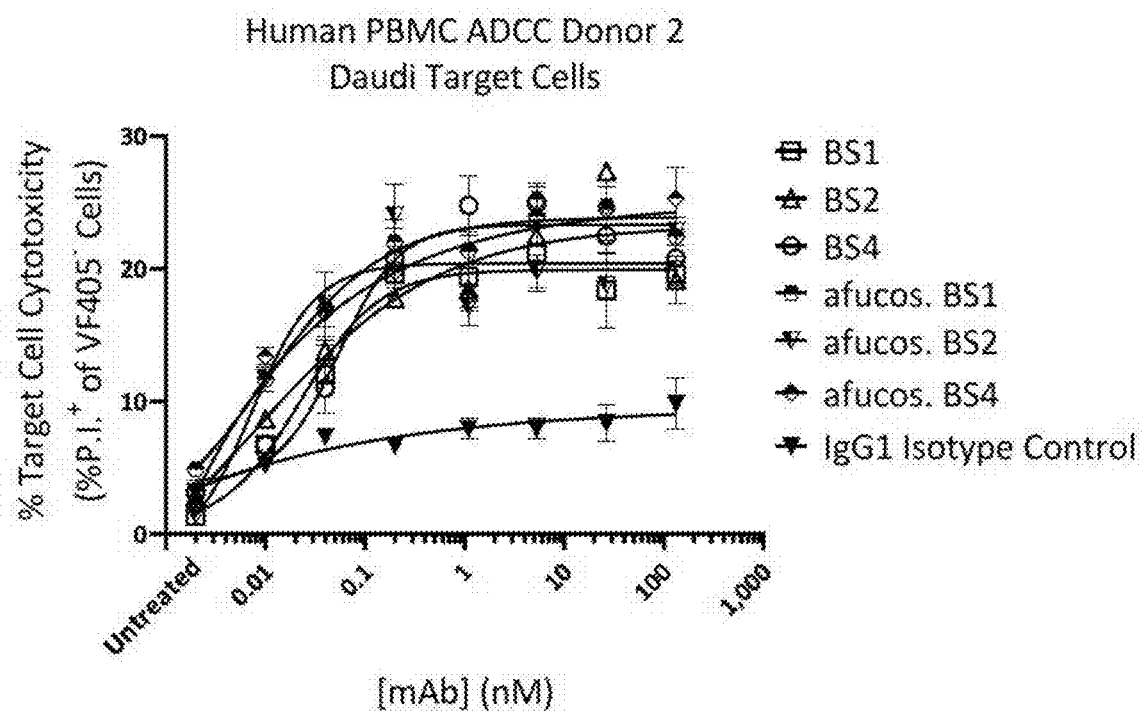
FIG. 21A to 21C shows ADCC data for three donors across antibody test articles.
Figure 21B:
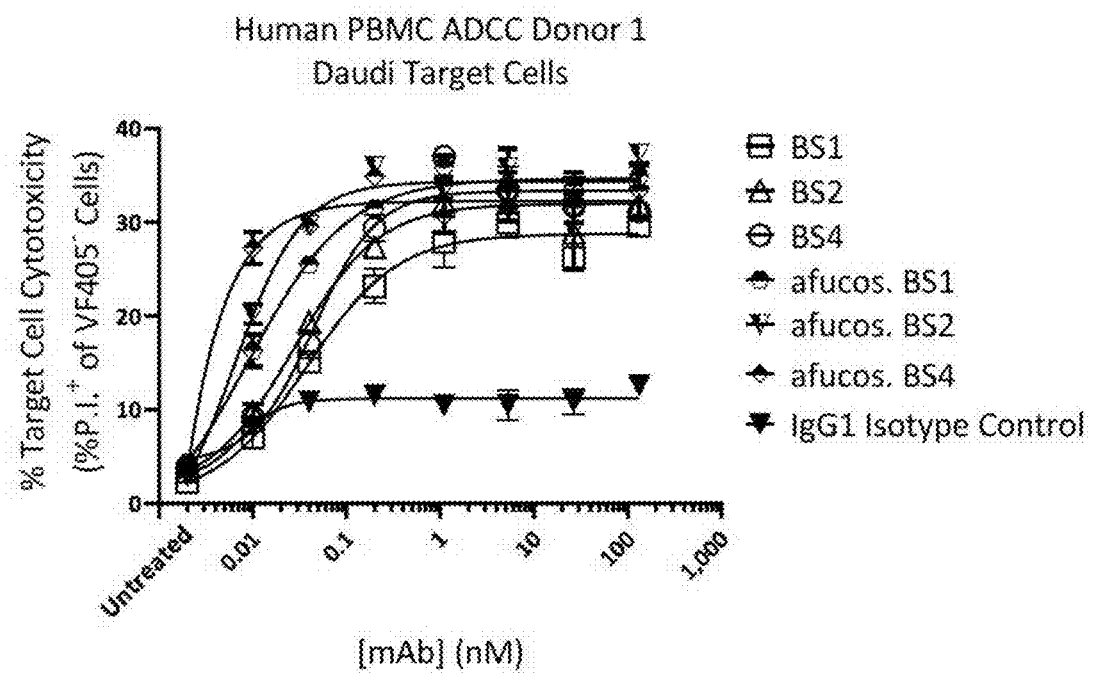
Figure 21C:
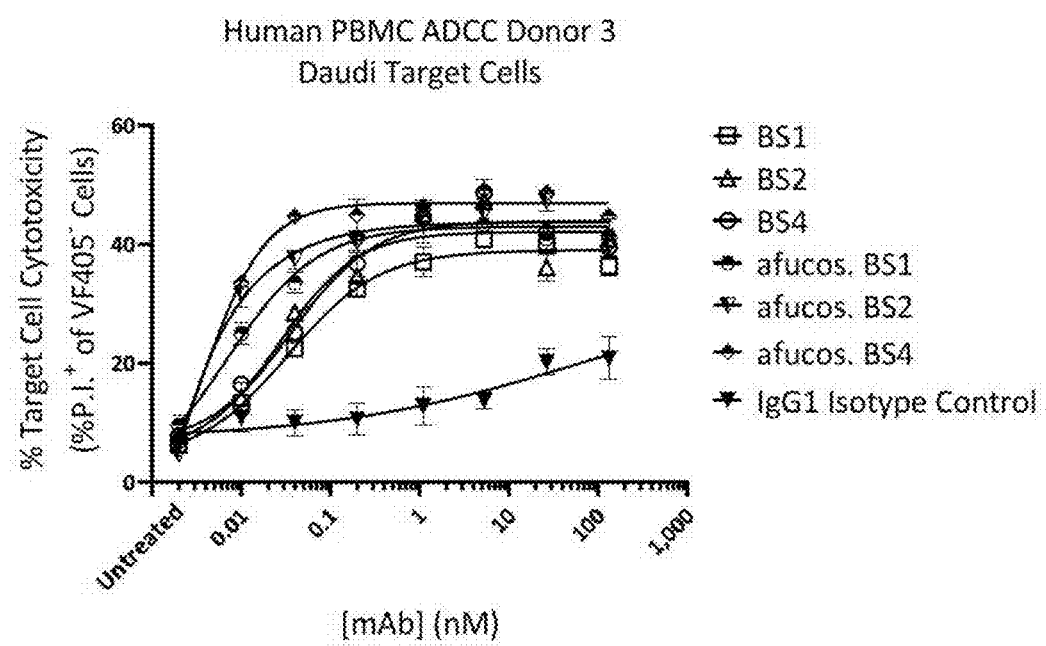

FIGS. 21A-C show ADCC for three donors. For all three donors, the results were similar. The three bispecific formats—BS1, BS2, BS4—exhibited similar levels of ADCC. Afucosylated versions of BS1, BS2, BS4 showed increased ADCC of about 10-fold compared to the fucosylated versions.

Complement-Dependent Cytotoxicity (CDC) assays were also performed. Target cells were treated with a dose response of the following test articles: BS1, BS2, 38K-VZVH, 19H-VZVH, 38K-VZVH/19H-VZVH combination, as well as controls of Darzalex®, anti-CD20, WT IgG1 Tafasitimab, and human IgG1 isotype control. All were tested at a top concentration of 133 nM, followed by a five-fold dilution series, 7 points total, in addition to no treatment controls. After 15 minutes of incubation at 37 C, 5% CO2, complement was added to treated cells at a final concentration of 25%. Cells were then incubated with complement for an additional 2 hours at 37 C, 5% CO2. After complement incubation, cells were washed and resuspended with 5 ug/mL of a viability dye, propidium iodide (P.I.), and acquired via high throughput flow cytometry.

Figure 22A:
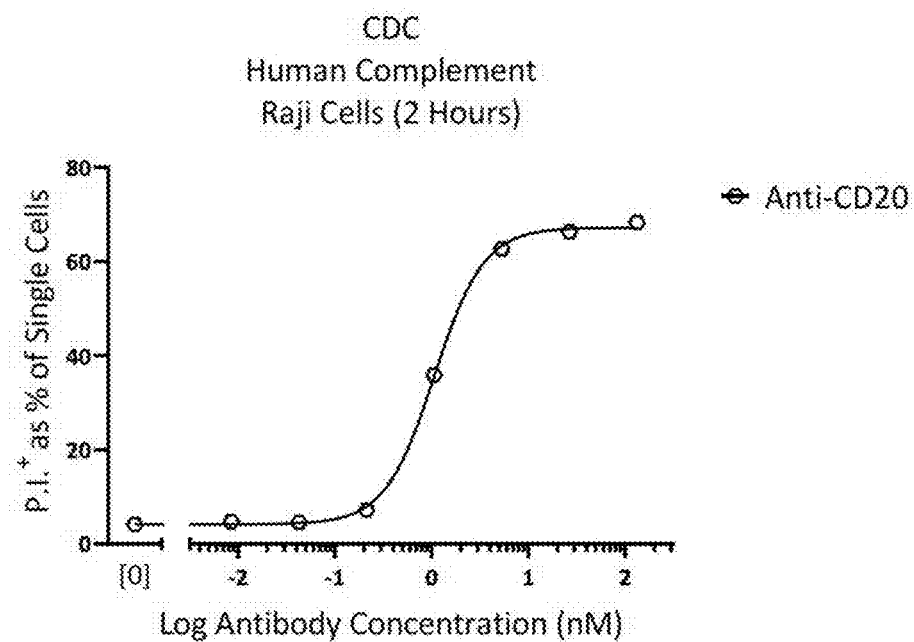
FIG. 22A to 22B shows CDC profiles across test articles.
Figure 22B:
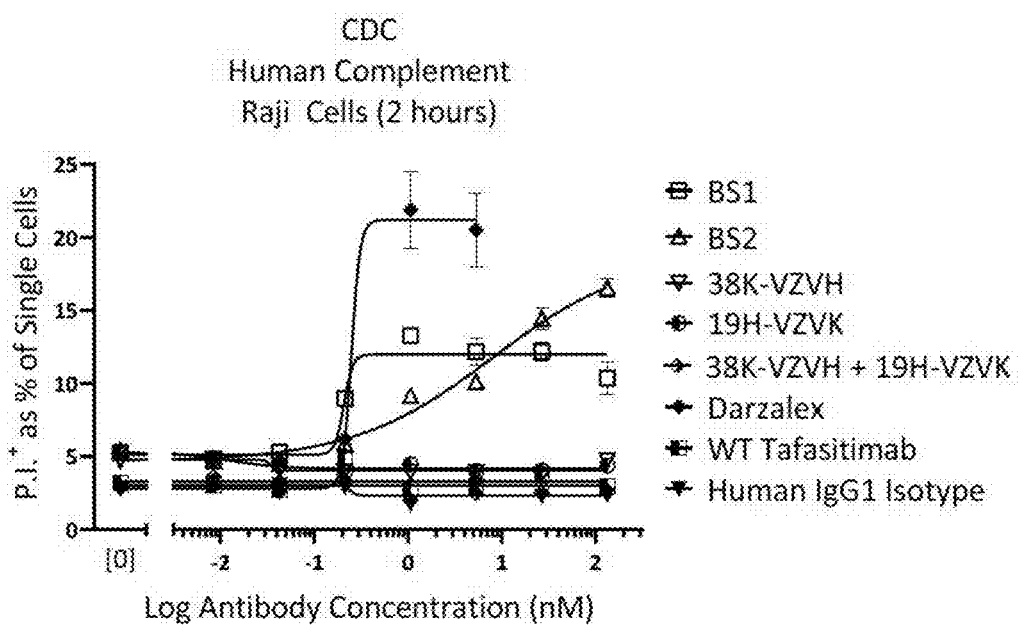

FIGS. 22A and 22B show results of complement-dependent cytotoxicity (CDC) assays. The positive technical control, anti-CD20, induced robust, dose-dependent CDC activity. 38K-VZVH and 19H-VZVH (either alone or in combination), anti-CD19 tafasitimab (wt IgG1), and human IgG1 isotype control did not induce any CDC activity. Darzalex®, BS1, and BS2 all showed CDC activity (though not to the same magnitude as anti-CD20, which is expected from the literature). The maximum cytotoxicity of Darzalex® was higher than that of both BS1 and BS2.

Antibody-dependent cellular phagocytosis (ADCP) was further assayed by pHrodo™ Green AM (pHG) labeled Raji cells treated with a dose response of test articles and incubated for 15 minutes at 37 C, 5% CO2. pHG is a pH sensitive dye, only weakly fluorescent at neutral pH, but highly fluorescent at low pH in the mature phagosomes of macrophages. pHG labeled Raji target cells with anti-CD20 antibody and IgG1 isotype control were used as a positive control and negative control, with a top concentration of 133 nM, 7-point five-fold dilution series, and 0 nM control. Pre-treated target cells were co-cultured with human macrophages (in vitro differentiated from monocytes) from n=3 donors (E:T 1:2). Macrophages were labeled with Cell Trace™ Violet (CTV). Samples were incubated for 4 hours at 37 C, 5% CO2 prior to flow cytometry analysis for phagocytosis. The percentage of pHGhi/CTV+ cells was analyzed as a measure of target cell phagocytosis. Percentages were plotted on an XY chart against the log of the test article concentration, and the data fit to a four-parameter non-linear regression curve from which the EC50 was calculated.

Figure 23:
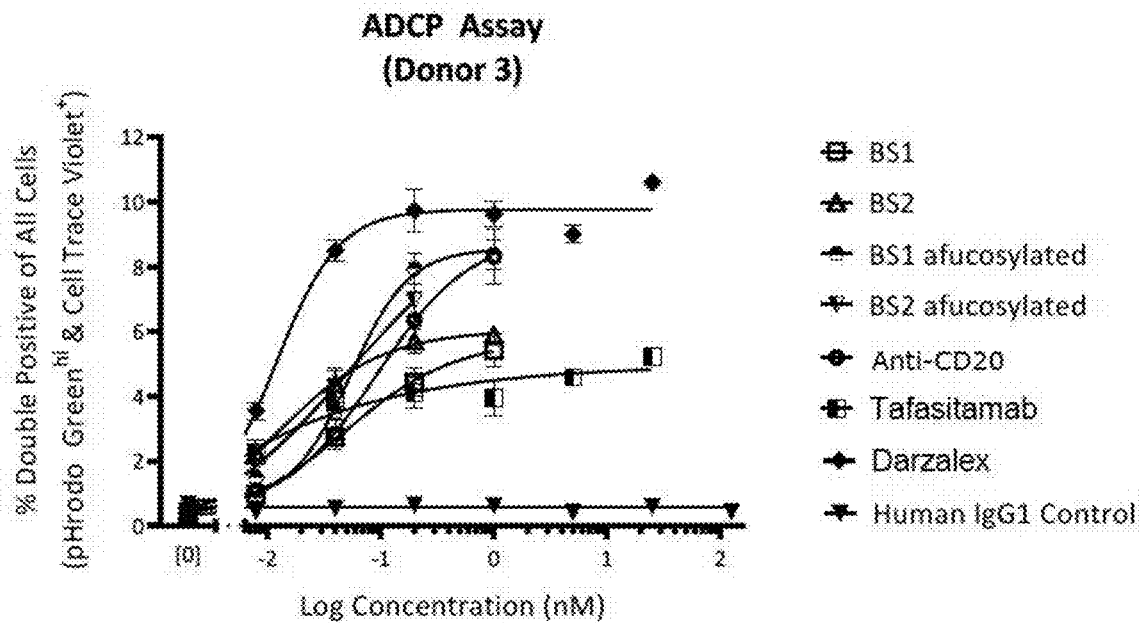
FIG. 23 shows ADCP data across antibody test articles.

FIG. 23 shows results of antibody-dependent cellular phagocytosis (ADCP) assays using Raji cells as target and donor macrophages. The positive control, anti-CD20, demonstrated dose-dependent phagocytosis for all three of the donors after 4 hours (between 5-10% max phagocytosis). The negative control, IgG1 isotype control, demonstrated no dose-dependent phagocytosis for all three of the donors after 4 hours. Darzalex® demonstrated dose-dependent phagocytosis for all three of the donors after 4 hours (between 4-10% max phagocytosis). BS-1, BS-2, afucosylated BS-1, and afucosylated BS-2 showed slight dose-dependent phagocytosis, with afucosylated formats resulting in an increase in ADCP.

Example 6: Interactions with RBCs

A flow-cytometry based Red Blood Cell (RBC) binding study was performed to evaluate binding of test articles to red blood cells from n=3 cynomolgus monkey and n=3 human donors. Whole blood was washed with 1×PBS and then diluted 20-fold with PBS, prior to treatment with test articles. Bispecifics (BS1, BS2), parental monoclonals (851A, 851D) and controls (anti-CD38 Darzalex®, recombinant anti-CD19 tafasitamab, IgG1 isotype control, anti-CD47 conjugated to Alexa Fluor™ 647) were tested at a top final concentration of 133 nM followed by a five-fold serial dilution of seven points total, in addition to 0 nM control, in triplicate. Single-arm controls (38K-VZVH, 19H-VZVK) were tested in combination, with both at a top concentration of 133 nM and the same dose response.

After incubation with primary antibodies for 30 minutes on ice, cells were washed and stained with 5 ug/mL of a secondary antibody (goat anti-human Fcγ F(ab')2 labeled with Alexa Fluor™ 647) to detect test article binding on red blood cells. Secondary was not used for anti-CD47-A647 stained cells. After incubation with secondary for an additional 30 minutes on ice, stained cells were washed, diluted, and acquired by high-throughput flow cytometry. The Alexa Fluor™ 647 GeoMean Fluorescence Intensity (MFI) of the single cell population was calculated. MFI of AF647 was plotted on an XY chart, graphing MFI against the log of the concentration, and the data fit to a non-linear regression curve from which the EC50 was calculated.

Figure 24:
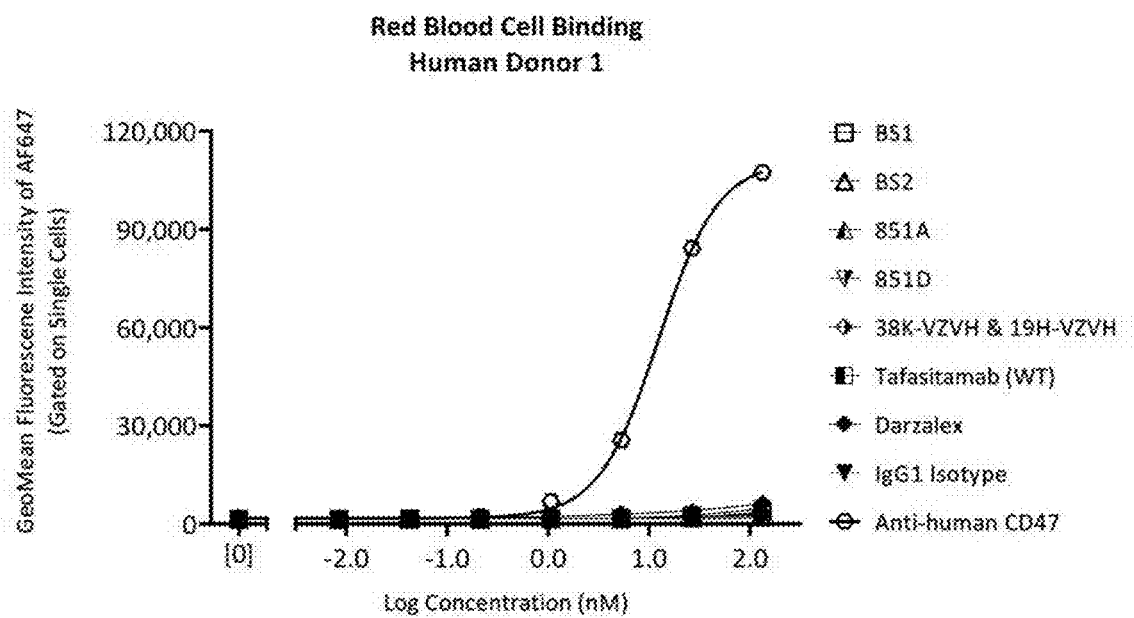
FIG. 24 shows RBC binding data across antibody test articles.

FIG. 24 shows that AF647-conjugated anti-CD47 showed a dose-response binding curve with all three human donors of red blood cells. Darzalex® also showed a dose-dependent increase in binding with all three donors, although the maximum MFI was an order of magnitude less than anti-CD47. Anti-CD38 851D showed the next highest maximum MFI, after Darzalex®, followed by BS1, BS2, 38K-VZVH & 19H-VZVK together, and anti-CD19 tafasitamab. Finally, anti-CD19 851A and IgG1 isotype showed only a slight increase in MFI at the highest concentration only.

An in vitro hemagglutination assay was performed on red blood cells from a total of three healthy (n=3) cynomolgus monkey (Cyno) donors and three healthy (n=3) human donors. Whole blood was acquired the day of the study and inspected for coagulation. Blood was then washed with PBS and diluted 1:50 to obtain the "whole blood substrate". Whole blood substrate was plated in 96-well round bottom plates and treated with test articles (BS1, BS2, 38K-VZVH+ 19H-VZVK, 851A, and 851D), controls (tafasitamab with wild-type IgG1), Darzalex®, and human IgG1 isotype control), or a positive technical control (IGM-55.5), in PBS at a top final concentration of 133 nM followed by a five-fold serial dilution of six points, in addition to 0 nM control, in triplicate. After 1 hour of incubation at 37 C, 5% CO2, the plate(s) were photographed to ascertain the level of hemagglutination. Each well was scored on a specific hemagglutination scale from 0-5, using the photographs as a reference. The specific manifestation of each score is somewhat relative to the individual donor.

Figure 25A:
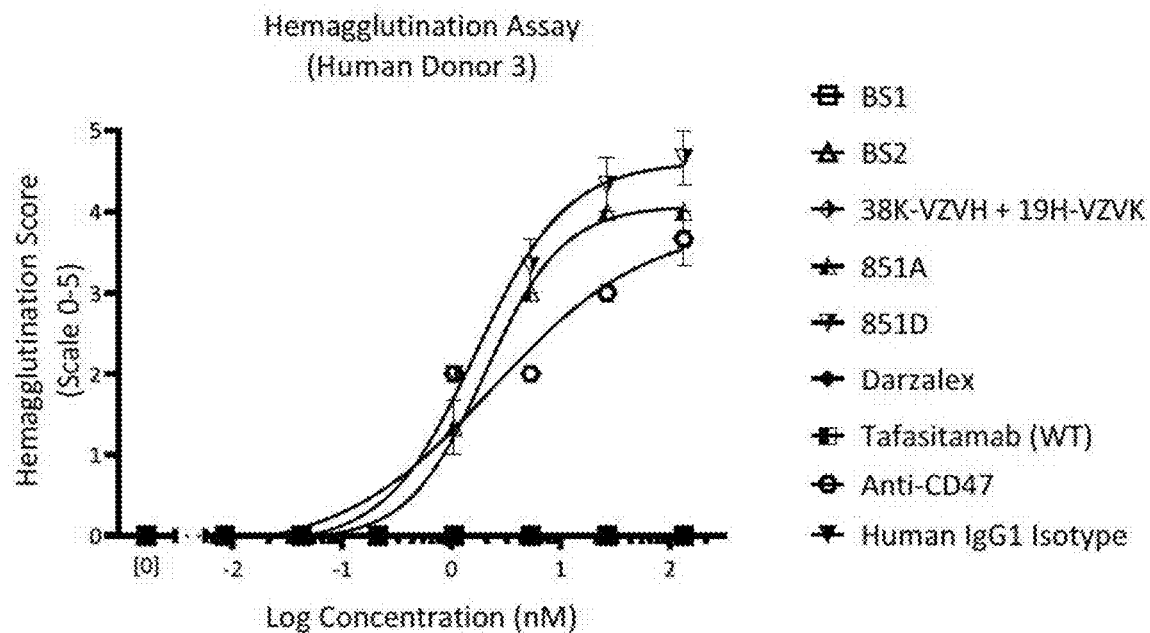
FIG. 25A to 25B shows hemagglutination profiles for antibody test articles.

FIG. 25A shows results of the hemagglutination assay for human donor 3. The positive control, anti-CD47, induced hemagglutination for all three human donors, starting between 0.04 and 1.1 nM. BS1, BS2, 38K-VZVH+19H-VZVK, Darzalex®, tafasitamab, and human IgG1 isotype control all showed no induction of hemagglutination at any concentration for all three donors. Monoclonal antibodies 851A (anti-CD19) and 851D (anti-CD38) both induced hemagglutination for all three donors, starting at 0.2 or 1.1 nM for each, with a response similar in magnitude to the technical control (anti-CD47). In contrast to the parent monoclonal antibodies, BS1 and BS2 did not show any induction of hemagglutination at any concentration.

Figure 25B:
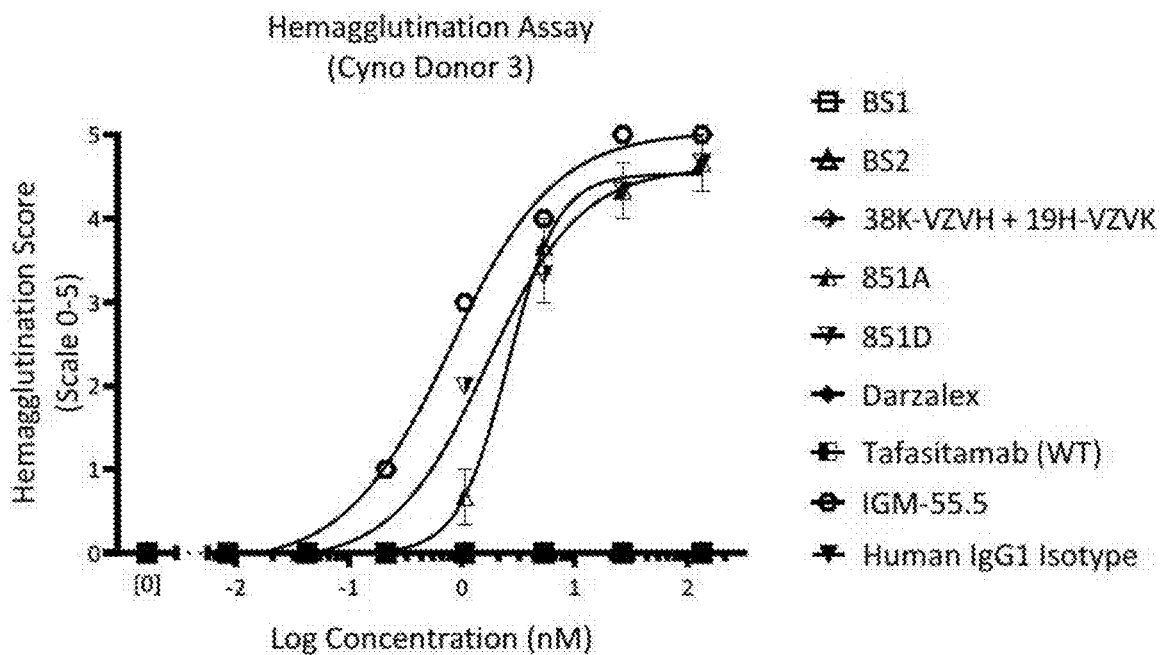

FIG. 25B shows results of the hemagglutination assay for cynomolgus donor 3. The positive control, IGM-55.5 (anti-little i antigen IgM antibody) induced hemagglutination for all three cyno donors starting at 0.04 or 0.2 nM. BS1, BS2, 38K-VZVH+19H-VZVK, Darzalex®, tafasitamab, and human IgG1 isotype control all showed no induction of hemagglutination at any concentration for all three donors. Monoclonal antibodies 851A (anti-CD19) and 851D (anti-CD38) both induced hemagglutination for all three donors, starting at 1.1 nM for each. In contrast to the parent monoclonal antibodies, BS1 and BS2 did not show any no induction of hemagglutination at any concentration.

An in vitro hemolysis assay was also performed on red blood cells from three (n=3) healthy cynomolgus monkey (cyno) and three (n=3) healthy human donors. Whole blood was acquired the day of the study and inspected for coagulation. Blood was washed with PBS and diluted 1:10 to obtain the "whole blood substrate". The whole blood substrate was treated with test articles and controls in PBS. Bispecifics (BS1, BS2), parental monoclonals (851A, 851D) and controls (anti-CD38 Darzalex®, recombinant anti-CD19 Tafasitamab, IgG1 isotype control) were tested at a top final concentration of 133 nM followed by a five-fold serial dilution of seven points total, in addition to 0 nM control, in triplicate. Single-arm controls (38K-VZVH, 19H-VZVK) were tested in combination, with both at a top concentration of 133 nM and the same dose response. Saponin was tested at a top concentration of 0.1% with a three-fold serial dilution of seven points total. After 1 hour of incubation at 37 C, 5% CO2, plates were centrifuged, and supernatant was collected. Supernatant was analyzed via plate reader for optical density (OD) at 540 nm. The positive control, Saponin, induced dose-dependent hemolysis starting at 0.001% thru 0.10%, for all species and donors. No test articles induced any hemolysis at any concentration tested.

Figure 26:
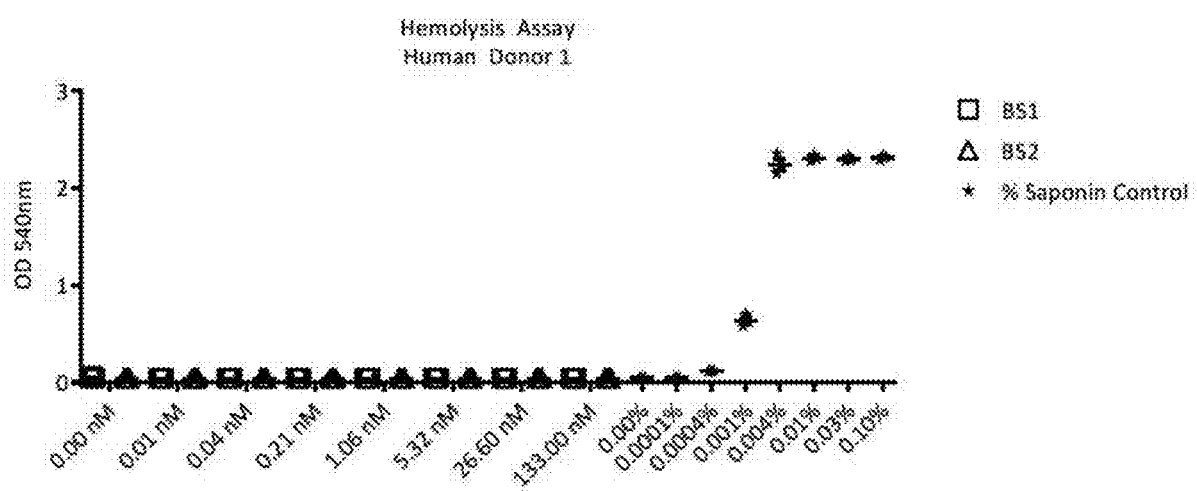
FIG. 26 shows hemolysis data across antibody test articles.

FIG. 26 shows that none of the test articles induced any hemolysis at any concentration tested. The positive control, Saponin, induced dose-dependent hemolysis starting at 0.001% thru 0.10%, for all species and donors.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCES

| # | SEQUENCE | ANNOTATION |
|---|----------|------------|
| 1 | QVQLVQSGAEVKKPGSSVKVSCKASGGTFSSY TINWVRQAPGQGLEWMGGIIPIFGIPNYAQKFQ GRVTITADESTNTAYMELSSLRAEDTAVYYCA RASGGSADYSYGMDVWGQGTAVTVSS | Anti-CD19_VH |

| # | SEQUENCE | ANNOTATION |
|---|---|---|
| 2 | DIQMTQSPSSLSASVGDRVTITCRASQGISSWL AWYQQKPEKAPKSLIYAASSLQSGVPSRFSGSG SGTDFTLTISSLQPEDFATYYCQQYKRYPYTFG QGTKLEIK | Anti-CD19_VL |
| 3 | QVQLVQSGAEVKKPGSSVKVSCKASGGTFSSY AFSWVRQAPGQGLEWMGRVIPFLGIANSAQKF QGRVTITADKSTSTAYMDLSSLRSEDTAVYYC ARDDIAALGPFDYWGQGTLVTVSS | Anti-CD38_VH |
| 4 | DIQMTQSPSSLSASVGDRVTITCRASQGISSWL AWYQQKPEKAPKSLIYAASSLQSGVPSRFSGSG SGTDFTLTISSLQPEDFATYYCQQYNSYPRTFG QGTKVEIK | Anti-CD38_VL |
| 5 | QVQLVQSGAEVKKPGSSVKVSCKASGGTF SSYAFSWVRQAPGQGLEWMGRVIPFLGIA NSAQKFQGRVTITADKSTSTAYMELSSLRS EDTAVYYCARDDIAALGPFDYWGQGTLVT VSS | Anti-CD38_VH ver 2 |
| 6 | QVQLVQSGAEVKKPGSSVKVSCKASGGTF SSYTINWVRQAPGQGLEWMGGIIPIFGIPNY AQKFQGRVTITADESTNTAYMELSSLRSED TAVYYCARASGGSADYSYGMDVWGQGTL VTVSS | Anti-CD 19_Ver2 |
| 7 | QVQLVQSGAEVKKPGSSVKVSCKASGGTF SSYTINWVRQAPGQGLEWMGGIIPIFGIPNY AQKFQGRVTITADESTNTAYMELSSLRSED TAVYYCARASGGSADYSYGMDVWGGGTL VTVSS | Anti-CD 19_Ver 3 |
| 11 | GGTFSSYT | Anti-CD19_VH_CDR1_IMGT |
| 12 | SYTIN | Anti-CD19_VH_CDR1_Kabat |
| 13 | GGTFSSY | Anti-CD19_VH_CDR1_Chothia |
| 14 | SSYTIN | Anti-CD19_VH_CDR1_Contact |
| 15 | GGTFSSYTIN | Anti-CD19_VH_CDR1_AbM |
| 21 | IIPIFGIP | Anti-CD19_VH_CDR2_IMGT |
| 22 | GIIPIFGIPNYAQKFQG | Anti-CD19_VH_CDR2_Kabat |
| 23 | PIFG | Anti-CD19_VH_CDR2_Chothia |
| 24 | WMGGIIPIFGIPN | Anti-CD19_VH_CDR2_Contact |
| 25 | GIIPIFGIPN | Anti-CD19_VH_CDR2_AbM |
| 31 | ARASGGSADYSYGMDV | Anti-CD19_VH_CDR3_IMGT |
| 32 | ASGGSADYSYGMDV | Anti-CD19_VH_CDR3_Kabat |
| 33 | SGGSADYSYGMD | Anti-CD19_VH_CDR3_Chothia |
| 34 | ARASGGSADYSYGMD | Anti-CD19_VH_CDR3_Contact |
| 35 | ASGGSADYSYGMDV | Anti-CD19_VH_CDR3_AbM |
| 41 | QGISSWLA | Anti-CD19_VL_CDR1_IMGT |
| 42 | RASQGISSWLA | Anti-CD19_VL_CDR1_Kabat |
| 43 | SQGISSW | Anti-CD19_VL_CDR1_Chothia |
| 44 | SSWLAWY | Anti-CD19_VL_CDR1_Contact |
| 45 | RASQGISSWLA | Anti-CD19_VL_CDR1_AbM |
| 51 | AAS | Anti-CD19_VL_CDR2_IMGT |

-continued

| # | SEQUENCE | ANNOTATION |
|---|---|---|
| 51 | AASSLQS | Anti-CD19_VL_CDR2_Kabat |
| 53 | AAS | Anti-CD19_VL_CDR2_Chothia |
| 54 | SLIYAASSLQ | Anti-CD19_VL_CDR2_Contact |
| 55 | AASSLQS | Anti-CD19_VL_CDR2_AbM |
| 61 | QQYKRYPYT | Anti-CD19_VL_CDR3_IMGT |
| 62 | QQYKRYPYT | Anti-CD19_VL_CDR3_Kabat |
| 63 | YKRYPY | Anti-CD19_VL_CDR3_Chothia |
| 64 | QQYKRYPY | Anti-CD19_VL_CDR3_Contact |
| 65 | QQYKRYPYT | Anti-CD19_VL_CDR3_AbM |
| 71 | GGTFSSYA | Anti-CD38_VH_CDR1_MGT |
| 72 | SYAFS | Anti-CD38_VH_CDR1_Kabat |
| 73 | GGTFSSY | Anti-CD38_VH_CDR1_Chothia |
| 74 | SSYAFS | Anti-CD38_VH_CDR1_Contact |
| 75 | GGTFSSYAFS | Anti-CD38_VH_CDR1_AbM |
| 81 | VIPFLGIA | Anti-CD38_VH_CDR2_IMGT |
| 82 | RVIPFLGIANSAQKFQG | Anti-CD38_VH_CDR2_Kabat |
| 83 | PFLG | Anti-CD38_VH_CDR2_Chothia |
| 84 | WMGRVIPFLGIAN | Anti-CD38_VH_CDR2_Contact |
| 85 | RVIPFLGIAN | Anti-CD38_VH_CDR2_AbM |
| 91 | ARDDIAALGPFDY | Anti-CD38_VH_CDR3_IMGT |
| 92 | DDIAALGPFDY | Anti-CD38_VH_CDR3_Kabat |
| 93 | DIAALGPFD | Anti-CD38_VH_CDR3_Chothia |
| 94 | ARDDIAALGPFD | Anti-CD38_VH_CDR3_Contact |
| 95 | DDIAALGPFDY | Anti-CD38_VH_CDR3_AbM |
| 101 | QGISSWLA | Anti-CD38_VL_CDR1_IMGT |
| 102 | RASQGISSWLA | Anti-CD38_VL_CDR1_Kabat |
| 103 | SQGISSW | Anti-CD38_VL_CDR1_Chothia |
| 104 | SSWLAWY | Anti-CD38_VL_CDR1_Contact |
| 105 | RASQGISSWLA | Anti-CD38_VL_CDR1_AbM |
| 111 | AAS | Anti-CD38_VL_CDR2_IMGT |
| 112 | AASSLQS | Anti-CD38_VL_CDR2_Kabat |
| 113 | AAS | Anti-CD38_VL_CDR2_Chothia |
| 114 | SLIYAASSLQ | Anti-CD38_VL_CDR2_Contact |
| 115 | AASSLQS | Anti-CD38_VL_CDR2_AbM |
| 121 | QQYNSYPRT | Anti-CD38_VL_CDR3_IMGT |
| 122 | QQYNSYPRT | Anti-CD38_VL_CDR3_Kabat |
| 123 | YNSYPR | Anti-CD38_VH_CDR3_Chothia |
| 124 | QQYNSYPR | Anti-CD38_VH_CDR3_Contact |

| # | SEQUENCE | ANNOTATION |
|---|---|---|
| 125 | QQYNSYPRT | Anti-CD38_VH_CDR3_AbM |
| 150 | P-X1-L-G-X2-A; wherein X1 and X2 is any amino acid | Anti-CD38_VH_CDR2 |
| 151 | PFLGTA | Anti-CD38_VH_CDR2 |
| 152 | PHLGIA | Anti-CD38_VH_CDR2 |
| 153 | PHLGTA | Anti-CD38_VH_CDR2 |
| 154 | PQLGIA | Anti-CD38_VH_CDR2 |
| 155 | PQLGTA | Anti-CD38_VH_CDR2 |
| 201 | QVQLVQSGAEVKKPGSSVKVSCKASGGTFSSYTINWVRQAPGQGLEWMGGIIPIFGIPNYAQKFQGRVTITADESTNTAYMELSSLRAEDTAVYYCARASGGSADYSYGMDVWGQGTAVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | BS1-19H |
| 202 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLWCLVKGFYPSDIAVEWESNGQPENNYKTTPPVLDSDGSFFLYSKLTVD KSRWQQGNVFSCSVMHEALHNHYTQKSLSLSPGK | BS1-38K |
| 203 | QVQLVQSGAEVKKPGSSVKVSCKASGGTFSSYTINWVRQAPGQGLEWMGGIIPIFGIPNYAQKFQGRVTITADESTNTAYMELSSLRAEDTAVYYCARASGGSADYSYGMDVWGQGTAVTVSSGGGGSGGGGSGGGGSDIQMTQSPSSLSASVGDRVTITCRASQGISSWLAWYQQKPEKAPKSLIYAASSLQSGVPSRFSGSGSGTDFTLTISSLQPEDFATYYCQQYKRYPYTFGQGTKLEIKAAEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | BS2-19H1 |
| 204 | QVQLVQSGAEVKKPGSSVKVSCKASGGTFSSYTINWVRQAPGQGLEWMGGIIPIFGIPNYAQKFQGRVTITADESTNTAYMELSSLRAEDTAVYYCARASGGSADYSYGMDVWGQGTAVTVSSGGGGSGGGGSGGGGSDIQMTQSPSSLSASVGDRVTITCRASQGISSWLAWYQQKPEKAPKSLIYAASSLQSGVPSRFSGSGSGTDFTLTISSLQPEDFATYYCQQYKRYPYTFGQGTKLEIKGGGGDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELT | BS2-19H2 |

| # | SEQUENCE | ANNOTATION |
|---|---|---|
| | KNQVSLSCAVKGFYPSDIAVEWESNGQPENNY<br>KTTPPVLDSDGSFFLVSKLTVDKSRWQQGNVF<br>SCSVMHEALHNHYTQKSLSLSPGK | |
| 205 | QVQLVQSGAEVKKPGSSVKVSCKASGGTFSSY<br>AFSWVRQAPGQGLEWMGRVIPFLGIANSAQKF<br>QGRVTITADKSTSTAYMDLSSLRSEDTAVYYC<br>ARDDIAALGPFDYWGQGTLVTVSSGGGGSGG<br>GGSGGGGSDIQMTQSPSSLSASVGDRVTITCRA<br>SQGISSWLAWYQQKPEKAPKSLIYAASSLQSG<br>VPSRFSGSGSGTDFTLTISSLQPEDFATYYCQQY<br>NSYPRTFGQGTKVEIKAAEPKSSDKTHTCPPCP<br>APELLGGPSVFLFPPKPKDTLMISRTPEVTCVV<br>VDVSHEDPEVKFNWYVDGVEVHNAKTKPREE<br>QYNSTYRVVSVLTVLHQDWLNGKEYKCKVSN<br>KALPAPIEKTISKAKGQPREPQVYTLPPSRDELT<br>KNQVSLWCLVKGFYPSDIAVEWESNGQPENN<br>YKTTPPVLDSDGSFFLYSKLTVDKSRWQQGNV<br>FSCSVMHEALHNHYTQKSLSLSPGK | BS2X-19H1 |
| 206 | QVQLVQSGAEVKKPGSSVKVSCKASGGTFSSY<br>AFSWVRQAPGQGLEWMGRVIPFLGIANSAQKF<br>QGRVTITADKSTSTAYMDLSSLRSEDTAVYYC<br>ARDDIAALGPFDYWGQGTLVTVSSGGGGSGG<br>GGSGGGGSDIQMTQSPSSLSASVGDRVTITCRA<br>SQGISSWLAWYQQKPEKAPKSLIYAASSLQSG<br>VPSRFSGSGSGTDFTLTISSLQPEDFATYYCQQY<br>NSYPRTFGQGTKVEIKGGGGDKTHTCPPCPAP<br>ELLGGPSVFLFPPKPKDTLMISRTPEVTCVVVD<br>VSHEDPEVKFNWYVDGVEVHNAKTKPREEQY<br>NSTYRVVSVLTVLHQDWLNGKEYKCKVSNKA<br>LPAPIEKTISKAKGQPREPQVYTLPPSRDELTKN<br>QVSLWCLVKGFYPSDIAVEWESNGQPENNYKT<br>TPPVLDSDGSFFLYSKLTVDKSRWQQGNVFSC<br>SVMHEALHNHYTQKSLSLSPGK | BS2X-19H2 |
| 207 | QVQLVQSGAEVKKPGSSVKVSCKASGGTFSSY<br>TINWVRQAPGQGLEWMGGIIPIFGIPNYAQKFQ<br>GRVTITADESTNTAYMELSSLRAEDTAVYYCA<br>RASGGSADYSYGMDVWGQGTAVTVSSASTKG<br>PSVFPLAPSSKSTSGGTAALGCLVKDYFPEPVT<br>VSWNSGALTSGVHTFPAVLQSSGLYSLSSVVT<br>VPSSSLGTQTYICNVNHKPSNTKVDKKVEPKSC<br>DKTHTCPPCPAPELLGGPSVFLFPPKPKDTLMIS<br>RTPEVTCVVVDVSHEDPEVKFNWYVDGVEVH<br>NAKTKPREEQYNSTYRVVSVLTVLHQDWLNG<br>KEYKCKVSNKALPAPIEKTISKAKGQPREPQVY<br>TLPPSRDELTKNQVSLWCLVKGFYPSDIAVEW<br>ESNGQPENNYKTTPPVLDSDGSFFLYSKLTVDK<br>SRWQQGNVFSCSVMHEALHNHYTQKSLSLSP<br>GGGGSGGGSQVQLVQSGAEVKKPGSSVKVSC<br>KASGGTFSSYAFSWVRQAPGQGLEWMGRVIPF<br>LGIANSAQKFQGRVTITADKSTSTAYMDLSSLR<br>SEDTAVYYCARDDIAALGPFDYWGQGTLVTVS<br>SASTKGPSVFPLAPSSKSTSGGTAALGCLVKDY<br>FPEPVTVSWNSGALTSGVHTFPAVLQSSGLYSL<br>SSVVTVPSSSLGTQTYICNVNHKPSNTKVDKK<br>VEPKSCDKTH | BS3-19H38 |
| 208 | DKTHTCPPCPAPELLGGPSVFLFPPKPKDTLMIS<br>RTPEVTCVVVDVSHEDPEVKFNWYVDGVEVH<br>NAKTKPREEQYNSTYRVVSVLTVLHQDWLNG<br>KEYKCKVSNKALPAPIEKTISKAKGQPREPQVY<br>TLPPSRDELTKNQVSLWCLVKGFYPSDIAVEWE<br>SNGQPENNYKTTPPVLDSDGSFFLVSKLTVDKS<br>RWQQGNVFSCSVMHEALHNHYTQKSLSLSPG<br>K | BS3-Fc |
| 209 | QVQLVQSGAEVKKPGSSVKVSCKASGGTFSSY<br>AFSWVRQAPGQGLEWMGRVIPFLGIANSAQKF<br>QGRVTITADKSTSTAYMDLSSLRSEDTAVYYC<br>ARDDIAALGPFDYWGQGTLVTVSSASTKGPSV<br>FPLAPSSKSTSGGTAALGCLVKDYFPEPVTVSW<br>NSGALTSGVHTFPAVLQSSGLYSLSSVVTVPSS<br>SLGTQTYICNVNHKPSNTKVDKKVEPKSCDKT | BS4-38K19 |

| # | SEQUENCE | ANNOTATION |
|---|---|---|
| | HTCPPCPAPELLGGPSVFLFPPKPKDTLMISRTP<br>EVTCVVVDVSHEDPEVKFNWYVDGVEVHNAK<br>TKPREEQYNSTYRVVSVLTVLHQDWLNGKEY<br>KCKVSNKALPAPIEKTISKAKGQPREPQVYTLP<br>PSRDELTKNQVSLWCLVKGFYPSDIAVEWESN<br>GQPENNYKTTPPVLDSDGSFFLYSKLTVDKSR<br>WQQGNVFSCSVMHEALHNHYTQKSLSLSPGG<br>GGSGGGSQVQLVQSGAEVKKPGSSVKVSCKA<br>SGGTFSSYTINWVRQAPGQGLEWMGGIIPIFGIP<br>NYAQKFQGRVTITADESTNTAYMELSSLRAED<br>TAVYYCARASGGSADYSYGMDVWGQGTAVT<br>VSSGGGGSGGGGSGGGGSDIQMTQSPSSLSAS<br>VGDRVTITCRASQGISSWLAWYQQKPEKAPKS<br>LIYAASSLQSGVPSRFSGSGSGTDFTLTISSLQPE<br>DFATYYCQQYKRYPYTFGQGTKLEIK | |
| 210 | DIQMTQSPSSLSASVGDRVTITCRASQGISSWL<br>AWYQQKPEKAPKSLIYAASSLQSGVPSRFSGSG<br>SGTDFTLTISSLQPEDFATYYCQQYKRYPYTFG<br>QGTKLEIKRTVAAPSVFIFPPSDEQLKSGTASVV<br>CLLNNFYPREAKVQWKVDNALQSGNSQESVT<br>EQDSKDSTYSLSSTLTLSKADYEKHKVYACEV<br>THQGLSSPVTKSFNRGEC | 19VL-CL |
| 211 | DIQMTQSPSSLSASVGDRVTITCRASQGISSWL<br>AWYQQKPEKAPKSLIYAASSLQSGVPSRFSGSG<br>SGTDFTLTISSLQPEDFATYYCQQYNSYPRTFG<br>QGTKVEIKRTVAAPSVFIFPPSDEQLKSGTASV<br>VCLLNNFYPREAKVQWKVDNALQSGNSQESV<br>TEQDSKDSTYSLSSTLTLSKADYEKHKVYACE<br>VTHQGLSSPVTKSFNRGEC | 38VL-CL |
| 212 | QVQLVQSGAEVKKPGSSVKVSCKASGGTF<br>SSYTINWVRQAPGQGLEWMGGIIPIFGIPNY<br>AQKFQGRVTITADESTNTAYMELSSLRAED<br>TAVYYCARASGGSADYSYGMDVWGQGT<br>AVTVSSGGGGSGGGGSGGGGSDIQMTQSP<br>SSLSASVGDRVTITCRASQGISSWLAWYQQ<br>KPEKAPKSLIYAASSLQSGVPSRFSGSGSGT<br>DFTLTISSLQPEDFATYYCQQYKRYPYTFG<br>QGTKLEIKGGGGGQVQLVQSGAEVKKPGS<br>SVKVSCKASGGTFSSYTINWVRQAPGQGL<br>EWMGGIIPIFGIPNYAQKFQGRVTITADEST<br>NTAYMELSSLRAEDTAVYYCARASGGSAD<br>YSYGMDVWGQGTAVTVSSASTKGPSVFPL<br>APSSKSTSGGTAALGCLVKDYFPEPVTVSW<br>NSGALTSGVHTFPAVLQSSGLYSLSSVVTV<br>PSSSLGTQTYICNVNHKPSNTKVDKKVEPK<br>SCDKTHTCPPCPAPELLGGPSVFLFPPKPKD<br>TLMISRTPEVTCVVVDVSHEDPEVKFNWY<br>VDGVEVHNAKTKPREEQYNSTYRVVSVLT<br>VLHQDWLNGKEYKCKVSNKALPAPIEKTI<br>SKAKGQPREPQVYTLPPSRDELTKNQVSL<br>WCLVKGFYPSDIAVEWESNGQPENNYKTT<br>PPVLDSDGSFFLYSKLTVDKSRWQQGNVF<br>SCSVMHEALHNHYTQKSLSLSPGK | 3C10 scFv-003Fab-Fc Knob<br>(BS3-19F38) |
| 213 | DIQMTQSPSSLSASVGDRVTITCRASQGISS<br>WLAWYQQKPEKAPKSLIYAASSLQSGVPS<br>RFSGSGSGTDFTLTISSLQPEDFATYYCQQY<br>NSYPRTFGQGTKVEIKRTVAAPSVFIFPPSD<br>EQLKSGTASVVCLLNNFYPREAKVQWKV<br>DNALQSGNSQESVTEQDSKDSTYSLSSTLT<br>LSKADYEKHKVYACEVTHQGLSSPVTKSF<br>NRGEC | 003VL (38VL-CL) |
| 214 | DKTHTCPPCPAPELLGGPSVFLFPPKPKDTL<br>MISRTPEVTCVVVDVSHEDPEVKFNWYVD<br>GVEVHNAKTKPREEQYNSTYRVVSVLTVL<br>HQDWLNGKEYKCKVSNKALPAPIEKTISK<br>AKGQPREPQVYTLPPSRDELTKNQVSLSCA<br>VKGFYPSDIAVEWESNGQPENNYKTTPVL<br>DSDGSFFLVSKLTVDKSRWQ GNVFSCSV<br>MHEALHNHYTQKSLSLSPGK | Fc Hole (BS3-Fc) |

| # | SEQUENCE | ANNOTATION |
|---|---|---|
| 215 | QVQLVQSGAEVKKPGSSVKVSCKASGGTF SSYAFSWVRQAPGQGLEWMGRVIPFLGIA NSAQKFQGRVTITADKSTSTAYMELSSLRS EDTAVYYCARDDIAALGPFDYWGQGTLVT VSSASTKGPSVFPLAPSSKSTSGGTAALGCL VKDYFPEPVTVSWNSGALTSGVHTFPAVL QSSGLYSLSSVVTVPSSSLGTQTYICNVNH KPSNTKVDKKVEPKSCDKTHTCPPCPAPEL LGGPSVFLFPPKPKDTLMISRTPEVTCVVV DVSHEDPEVKFNWYVDGVEVHNAKTKPR EEQYNSTYRVVSVLTVLHQDWLNGKEYK CKVSNKALPAPIEKTISKAKGQPREPQVYT LPPSRDELTKNQVSLWCLVKGFYPSDIAVE WESNGQPENNYKTTPPVLDSDGSFFLYSKL TVDKSRWQQGNVFSCSVMHEALHNHYTQ KSLSLSPGK | BS1-38K ver2 |
| 216 | QVQLVQSGAEVKKPGSSVKVSCKASGGTF SSYTINWVRQAPGQGLEWMGGIIPIFGIPNY AQKFQGRVTITADESTNTAYMELSSLRSED TAVYYCARSGGSADYSYGMDVWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICNV NHKPSNTKVDKKVEPKSCDKTHTCPPCPA PELLGGPSVFLFPPKPKDTLMISRTPEVTCV VVDVSHEDPEVKFNWYVDGVEVHNAKTK PREEQYNSTYRVVSVLTVLHQDWLNGKEY KCKVSNKALPAPIEKTISKAKGQPREPQVY TLPPSRDELTKNQVSLSCAVKGFYPSDIAV EWESNGQPENNYKTTPPVLDSDGSFFLVSK LTVDKSRWQQGNVFSCSVMHEALHNHYT QKSLSLSPGK | BS1-19H ver2 |
| 217 | QVQLVQSGAEVKKPGSSVKVSCKASGGTF SSYTINWVRQAPGQGLEWMGGIIPIFGIPNY AQKFQGRVTITADESTNTAYMELSSLRSED TAVYYCARSGGSADYSYGMDVWGGGTL VTVSSGGGGSGGGGSGGGGSDIQMTQSPS SLSASVGDRVTITCRASQGISSWLAWYQQ KPEKAPKSLIYAASSLQSGVPSRFSGSGSGT DFTLTISSLQPEDFATYYCQQYKRYPYTFG QGTKLEIKAAEPKSSDKTHTCPPCPAPELL GGPSVFLFPPKPKDTLMISRTPEVTCVVVD VSHEDPEVKFNVVYVDGVEVHNAKTKPRE EQYNSTYRVVSVLTVLHQDWLNGKEYKC KVSNKALPAPIEKTISKAKGQPREPQVYTL PPSRDELTKNQVSLSCAVKGFYPSDIAVEW ESNGQPENNYKTTPPVLDSDGSFFLVSKLT VDKSRWQQGNVFSCSVMHEALHNHYTQK SLSLSPGK | BS2-19H ver2 |
| 218 | QVQLVQSGAEVKKPGSSVKVSCKASGGTF SSYAFSWVRQAPGQGLEWMGRVIPFLGTA NSAQKFQGRVTITADKSTSTAYMELSSLRS EDTAVYYCARDDIAALGPFDYWGQGTLVT VSS | BS1M-1 |
| 219 | QVQLVQSGAEVKKPGSSVKVSCKASGGTF SSYAFSWVRQAPGQGLEWMGRVIPHLGIA NSAQKFQGRVTITADKSTSTAYMELSSLRS EDTAVYYCARDDIAALGPFDYWGQGTLVT VSS | BS1M-3 |
| 220 | QVQLVQSGAEVKKPGSSVKVSCKASGGTF SSYAFSWVRQAPGQGLEWMGRVIPHLGTA NSAQKFQGRVTITADKSTSTAYMELSSLRS EDTAVYYCARDDIAALGPFDYWGQGTLVT VSS | BS1M-4 |
| 221 | QVQLVQSGAEVKKPGSSVKVSCKASGGTF SSYAFSWVRQAPGQGLEWMGRVIPQLGIA NSAQKFQGRVTITADKSTSTAYMELSSLRS EDTAVYYCARDDIAALGPFDYWGQGTLVT VSS | BS1M-6 |

| # | SEQUENCE | ANNOTATION |
|---|----------|------------|
| 222 | QVQLVQSGAEVKKPGSSVKVSCKASGGTF SSYAFSWVRQAPGQGLEWMGRVIPQLGTA NSAQKFQGRVTITADKSTSTAYMELSSLRS EDTAVYYCARDDIAALGPFDYWGQGTLVT VSS | BS1M-7 |
| 223 | DIQMTQSPSSLSASVGDRVTITCRASQGISS HLAWYQQKPEKAPKSLIYAASSLQSGVPSR FSGSGSGTDFTLTISSLQPEDFATYYCQQYN SYPRTFGQGTKVEIK | BSM-10 |

The invention claimed is:

1. A common light chain bispecific antibody wherein the common light chain bispecific antibody comprises an anti-human-CD38 immunoglobulin heavy chain variable region paired with a common immunoglobulin light chain variable region and an anti-human-CD19 immunoglobulin heavy chain variable region paired with the common immunoglobulin light chain variable region, wherein the anti-human-CD38 immunoglobulin heavy chain variable region comprises:
   (a) a heavy chain complementarity determining region 1 (HCDR1) comprising an amino acid sequence set forth in SEQ ID NO: 72;
   (b) a heavy chain complementarity determining region 2 (HCDR2) comprising an amino acid sequence set forth in SEQ ID NO: 154; and
   (c) a heavy chain complementarity determining region 3 (HCDR3) comprising an amino acid sequence set forth in SEQ ID NO: 93;
wherein the anti-human-CD19 immunoglobulin heavy chain variable region comprises:
   (d) a heavy chain complementarity determining region 1 (HCDR1) comprising an amino acid sequence set forth in SEQ ID NO: 12;
   (e) a heavy chain complementarity determining region 2 (HCDR2) comprising an amino acid sequence set forth in SEQ ID NO: 23; and
   (f) a heavy chain complementarity determining region 3 (HCDR3) comprising an amino acid sequence set forth in SEQ ID NO: 33;
wherein the common immunoglobulin light chain variable region comprises:
   (g) a light chain complementarity determining region 1 (LCDR1) comprising an amino acid sequence set forth in SEQ ID NO: 103;
   (h) a light chain complementarity determining region 2 (LCDR2) comprising an amino acid sequence set forth in SEQ ID NO: 113; and
   (i) a light chain complementarity determining region 3 (LCDR3) comprising an amino acid sequence set forth in SEQ ID NO: 123.

2. The common light chain bispecific antibody of claim 1, wherein the anti-human-CD38 immunoglobulin heavy chain variable region comprises an amino acid sequence having at least 90% identity to SEQ ID NO: 3 or 5, wherein the anti-human-CD38 immunoglobulin heavy chain variable region comprises (a), (b), and (c) of claim 1.

3. The common light chain bispecific antibody of claim 2, wherein the anti-human-CD38 immunoglobulin heavy chain variable region comprises an amino acid sequence identical to SEQ ID NO: 3 or 5, wherein the phenylalanine at position 54 of SEQ ID NO: 3 or at position 54 of SEQ ID NO: 5 is substituted with glutamine.

4. The common light chain bispecific antibody of claim 1, wherein the anti-human-CD19 immunoglobulin heavy chain variable region comprises an amino acid sequence having at least 90% identity to SEQ ID NO: 1 or 6, wherein the anti-human-CD19 immunoglobulin heavy chain variable region comprises (d), (e), and (f) of claim 1.

5. The common light chain bispecific antibody of claim 4, wherein the anti-human-CD19 immunoglobulin heavy chain variable region comprises an amino acid sequence identical to SEQ ID NO: 1 or 6.

6. The common light chain bispecific antibody of claim 1, wherein the common light chain bispecific antibody comprises an anti-human-CD38 immunoglobulin heavy chain constant region, comprising one or more amino acid substitutions that inhibit homodimerization of the anti-human-CD38 immunoglobulin heavy chain constant region and promote heterodimerization of the anti-human-CD38 immunoglobulin heavy chain constant region with a non-anti-human-CD38 immunoglobulin heavy chain constant region.

7. The common light chain bispecific antibody of claim 6, wherein the anti-human-CD38 immunoglobulin heavy chain constant region comprises a T366W substitution according to EU numbering or T366S/L368A/Y407V substitution according to EU numbering.

8. The common light chain bispecific antibody of claim 1, wherein the common light chain bispecific antibody comprises an anti-human CD19 immunoglobulin heavy chain constant region comprising one or more amino acid substitutions that inhibit homodimerization of the anti-human-CD19 immunoglobulin heavy chain constant region and promote heterodimerization of the anti-human-CD19 immunoglobulin heavy chain constant region with a non-anti-human CD19 immunoglobulin heavy chain constant region.

9. The common light chain bispecific antibody of claim 8, wherein the anti-human-CD19 immunoglobulin heavy chain constant region comprises a T366W substitution according to EU numbering or a T366S/L368A/Y407V substitution according to EU numbering.

10. The common light chain bispecific antibody of claim 1, wherein the common immunoglobulin light chain variable region further comprises an immunoglobulin light chain constant region.

11. The common light chain bispecific antibody of claim 1, comprising an anti-human-CD19 immunoglobulin heavy chain comprising the amino acid sequence set forth in SEQ ID NO: 201, a common immunoglobulin light chain comprising the amino acid sequence set forth in SEQ ID NO: 213, and an anti-human-CD38 immunoglobulin heavy chain comprising the amino acid sequence set forth in SEQ ID NO: 202 or 215 wherein the phenylalanine at position 54 of SEQ ID NO: 202 or SEQ ID NO: 215 is substituted with glutamine.

12. The common light chain bispecific antibody of claim 1, wherein the anti-human-CD19 immunoglobulin heavy chain variable region comprises an A84S or an A108L substitution according to Kabat numbering.

13. The common light chain bispecific antibody of claim 1, wherein the common immunoglobulin light chain variable region comprises a W32H substitution according to Kabat numbering.

14. The common light chain bispecific antibody of claim 1, wherein the common immunoglobulin light chain variable region comprises an amino acid sequence having at least 90% identity to SEQ ID NO: 4, wherein the common immunoglobulin light chain variable region comprises (g), (h), and (i) of claim 1.

15. The common light chain bispecific antibody of claim 1, wherein the common immunoglobulin light chain variable region comprises the amino acid sequence of SEQ ID NO: 4.

16. A composition comprising the common light chain bispecific antibody of claim 1 and a pharmaceutically acceptable diluent, carrier, or excipient.

17. A nucleic acid or plurality of nucleic acids comprising a polynucleotide sequence encoding the common light chain bispecific antibody of claim 1.

* * * * *